(12) United States Patent
Minskoff

(10) Patent No.: US 10,737,042 B2
(45) Date of Patent: Aug. 11, 2020

(54) THERMAL MODULATION OF AN INHALABLE MEDICAMENT

(71) Applicant: Michael Edward Breede, Ridgefield, CT (US)

(72) Inventor: Noah Mark Minskoff, Palo Alto, CA (US)

(73) Assignee: Michael Edward Breede, Ridgefield, CT (US)

(*) Notice: Subject to any disclaimer, the term of this patent is extended or adjusted under 35 U.S.C. 154(b) by 0 days.

(21) Appl. No.: 16/424,459

(22) Filed: May 28, 2019

(65) Prior Publication Data

US 2019/0314586 A1  Oct. 17, 2019

Related U.S. Application Data

(63) Continuation-in-part of application No. 14/835,595, filed on Aug. 25, 2015, now Pat. No. 10,300,228.

(Continued)

(51) Int. Cl.
*A61M 15/00* (2006.01)
*A61M 11/04* (2006.01)
(Continued)

(52) U.S. Cl.
CPC ........ *A61M 15/0036* (2014.02); *A61M 11/02* (2013.01); *A61M 11/041* (2013.01); *A61M 15/009* (2013.01); *A61M 39/00* (2013.01); *A61M 2039/0036* (2013.01); *A61M 2205/123* (2013.01)

(58) Field of Classification Search
CPC ............ A61M 11/042; A61M 15/0005; A61M 15/0033; A61M 15/0035; A61M 15/009; A61M 15/02; A61M 16/04; A61M 16/1075; A61M 2016/0039; A61M 2205/3368; A61M 2205/3375; A61M 2205/36; A61M 2205/502; A61M 2205/505; A61M 2205/52; A61M 2205/8206; A61M 2205/8225; A61M 2230/50

See application file for complete search history.

(56) References Cited

U.S. PATENT DOCUMENTS

| | | | |
|---|---|---|---|
| 3,761,285 | A | 9/1973 | Nagasawa et al. |
| 5,662,271 | A | 9/1997 | Weston et al. |

(Continued)

FOREIGN PATENT DOCUMENTS

| | | |
|---|---|---|
| WO | 1996028205 A1 | 9/1996 |
| WO | 2008040841 A1 | 4/2008 |

OTHER PUBLICATIONS

European Patent Office, "Extended European Search Report," European Application No. 15835153.6, dated Mar. 26, 2018.

(Continued)

*Primary Examiner* — Joshua Lee
(74) *Attorney, Agent, or Firm* — Durham Jones & Pinegar, P.C., Intellectual Property Law Group

(57) ABSTRACT

A thermally modulating inhalable medicament delivery device may deliver an inhalable medicament as an aerosol, vapor, or partial aerosol and partial vapor mixture. The inhalable medicament may be delivered to a target in a subject. Described herein are devices, systems, and methods for delivering an inhalable medicament to a subject.

20 Claims, 33 Drawing Sheets

Related U.S. Application Data

(60) Provisional application No. 62/187,289, filed on Jul. 1, 2015, provisional application No. 62/061,956, filed on Oct. 9, 2014, provisional application No. 62/061,669, filed on Oct. 8, 2014, provisional application No. 62/042,224, filed on Aug. 26, 2014.

(51) Int. Cl.
*A61M 39/00* (2006.01)
*A61M 11/02* (2006.01)

(56) References Cited

U.S. PATENT DOCUMENTS

| | | | |
|---|---|---|---|
| 5,957,124 A | 9/1999 | Lloyd et al. | |
| 6,054,082 A | 4/2000 | Heide et al. | |
| 6,948,496 B2 | 9/2005 | Eason et al. | |
| 7,021,559 B2 | 4/2006 | Fraser-Easton | |
| 8,434,477 B2 | 5/2013 | De Vos | |
| 8,523,843 B2 | 9/2013 | Kavanagh et al. | |
| 8,584,673 B2 | 11/2013 | Thoemmes et al. | |
| 10,300,228 B2 | 5/2019 | Minskoff | |
| 2003/0230303 A1 | 12/2003 | Nichols et al. | |
| 2004/0118396 A1 | 6/2004 | Hughes et al. | |
| 2004/0163645 A1* | 8/2004 | Connelly | A61M 15/0028 128/203.15 |
| 2007/0151560 A1* | 7/2007 | Price | A61M 15/0028 128/203.12 |
| 2007/0221216 A1* | 9/2007 | Ganem | A61M 15/0028 128/203.12 |
| 2007/0250007 A1* | 10/2007 | Shekalim | A61M 5/14244 604/131 |
| 2008/0135047 A1 | 6/2008 | Johnson et al. | |
| 2009/0240196 A1 | 9/2009 | Truax | |
| 2010/0059049 A1 | 3/2010 | Genosar | |
| 2010/0108062 A1* | 5/2010 | Ganem | A61M 15/0028 128/203.21 |
| 2011/0290243 A1* | 12/2011 | Bach | A61M 15/0065 128/200.21 |
| 2012/0103326 A1* | 5/2012 | Karle | A61D 7/04 128/200.21 |
| 2012/0132204 A1 | 5/2012 | Lucking et al. | |
| 2013/0239964 A1* | 9/2013 | Young | A61M 15/0028 128/203.21 |
| 2013/0317477 A1 | 11/2013 | Edwards et al. | |
| 2014/0118396 A1 | 5/2014 | Sugita et al. | |
| 2015/0320936 A1* | 11/2015 | Dunne | A61M 5/2033 604/199 |
| 2016/0030181 A1* | 2/2016 | Forsell | A61B 17/1666 623/18.11 |

OTHER PUBLICATIONS

USPTO as International Searching Authority, "International Search Report and Written Opinion," International Application No. PCT/US2015/047037, dated Feb. 1, 2016.

Japanese Patent Office, "Office Action," Japanese Application No. 2017-530964, dated May 22, 2019.

Fernandez T.A., et al., "Deposition of Inhaled Particles in the Lungs," Arch Bronconeumol. 48(7):240-246 (2012).

Zarogouldis, P., et al., "Vectors for Inhaled Gene Therapy in Lung Cancer Application for Nano Oncology and Safety of Bio Nanotechnology," Int. J. Mol. Sci. 13:10828-10862 (2012).

China National Intellectual Property Administration, "Office Action," Chinese Application No. 201580057946.4, dated Aug. 1, 2019.

Japanese Patent Office, "Second Office Action," Japanese Application No. 2017-530964, dated Mar. 3, 2020.

* cited by examiner

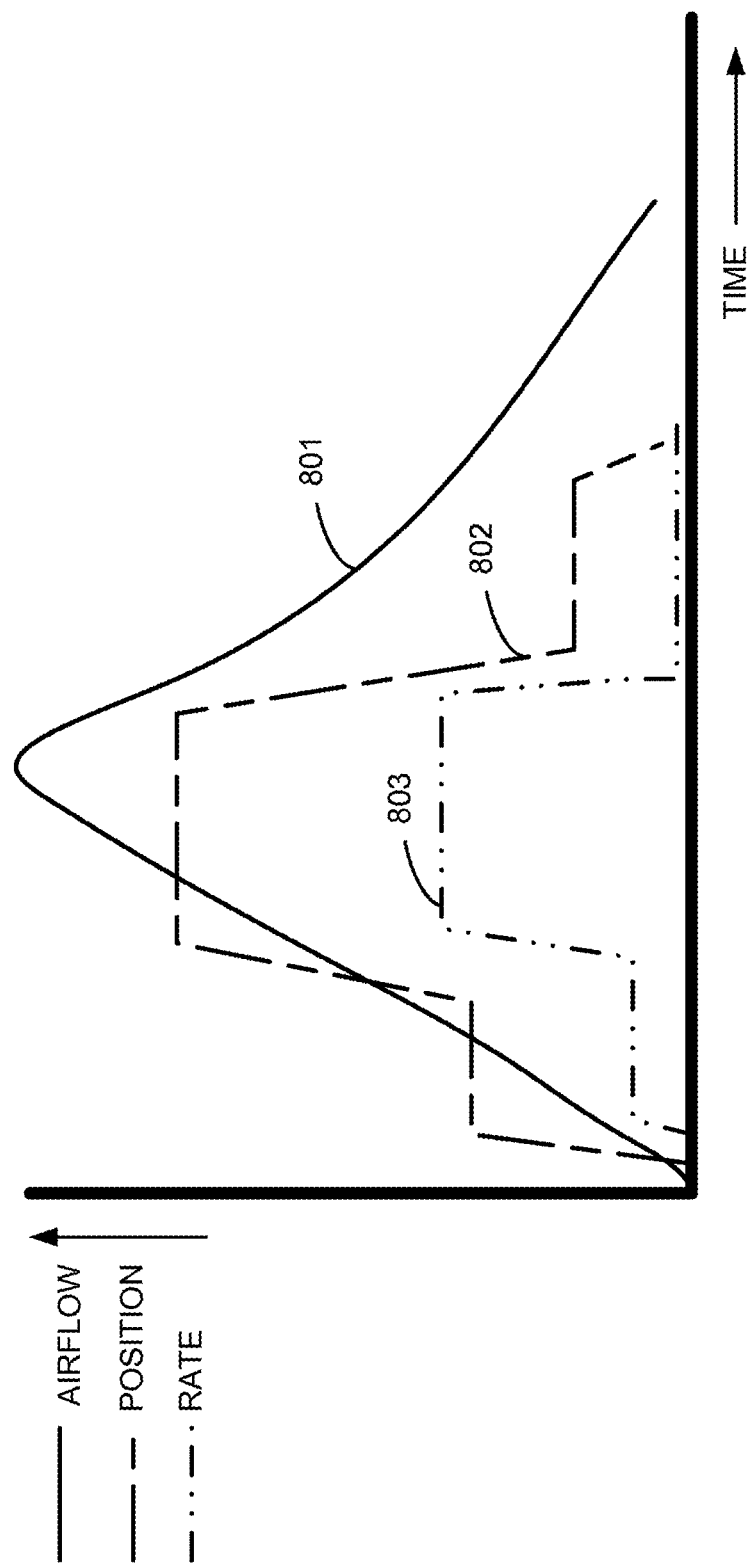

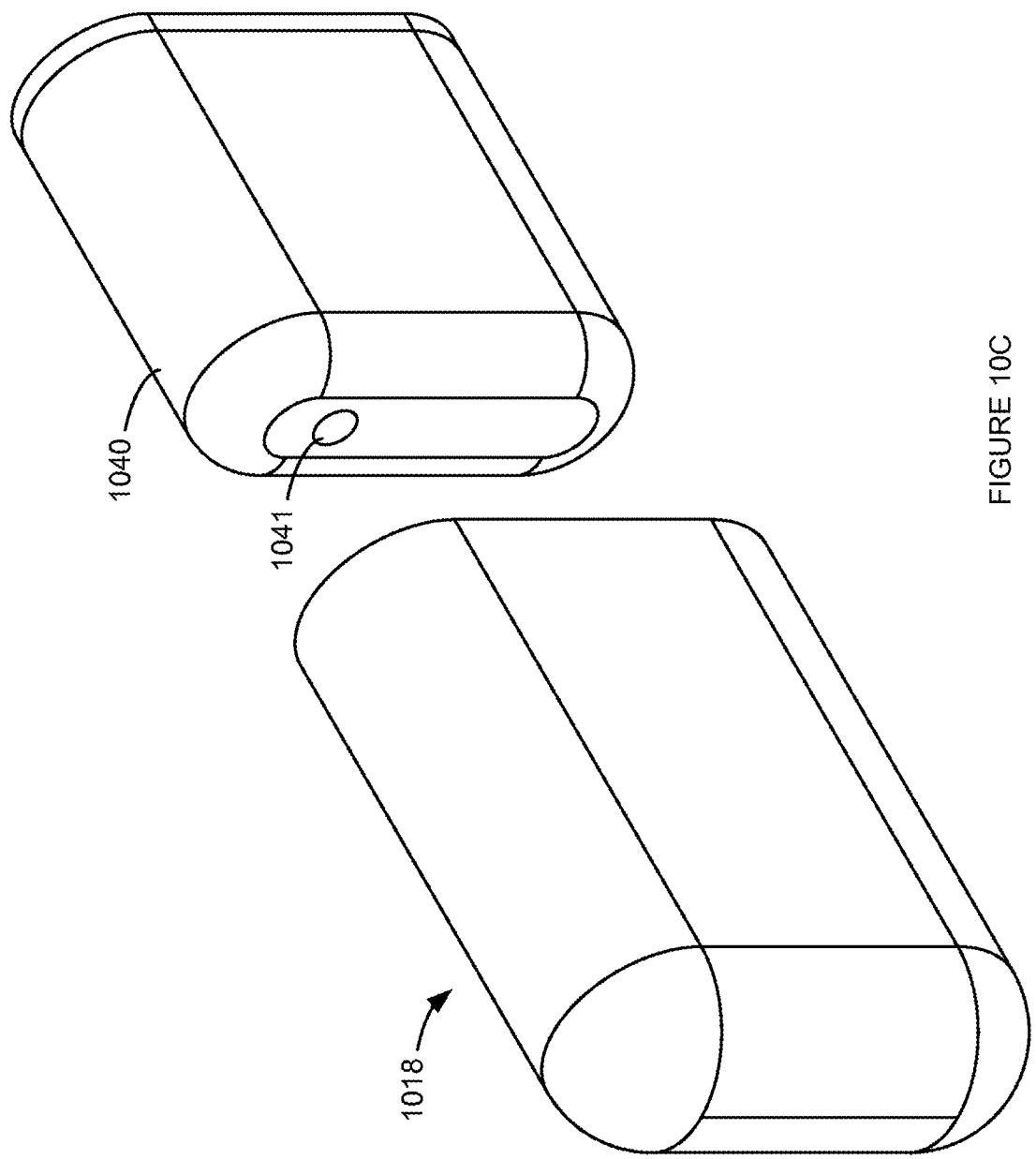

THERMAL MODULATION OF AN INHALABLE MEDICAMENT

CROSS-REFERENCE TO RELATED APPLICATIONS

This application is a continuation-in-part of U.S. application Ser. No. 14/835,595, filed on Aug. 25, 2015 and titled THERMAL MODULATION OF AN INHALABLE MEDICAMENT, which issued as U.S. Pat. No. 10,300,228 on May 28, 2019 ("the '595 Application"). The '595 Application included claims for the benefit of priority pursuant to 35 U.S.C. § 119(e) to the Jul. 1, 2015 filing date of U.S. Provisional Patent Application No. 62/187,289, titled THERMAL MODULATION OF AN INHALABLE MEDICAMENT, the Aug. 26, 2014 filing date of U.S. Provisional Patent Application No. 62/042,224, titled INHALABLE DRUG DELIVERY DEVICE—RELATED SYSTEMS, METHODS, FORMULATIONS, AND APPARATUS, the Oct. 18, 2014 filing date of U.S. Provisional Patent Application No. 62/061,669, titled THERMAL MODULATING INHALABLE MEDICAMENT DELIVERY SYSTEM, and the Oct. 9, 2014 filing date of U.S. Provisional Patent Application No. 62/061,956, titled THERMAL MODULATING INHALABLE MEDICAMENT DELIVERY SYSTEM. The entire disclosures of all of the foregoing are hereby incorporated herein for all purposes.

RELATED ART

Medicaments may be delivered in an inhalable formulation to treat a variety of medical conditions and symptoms. Such inhalable medicament formulations may be delivered directly to the lungs. Additionally, an inhalable medicament may be delivered systemically via delivery of the inhalable medicament to the pulmonary vascular system.

A handheld device that can controllably and effectively deliver an inhalable medicament to a target tissue in a subject would be advantageous in, for example, treating a variety of medical conditions and symptoms, and for delivery of a medicament systemically.

SUMMARY

Described herein are systems, devices, and methods for delivering an inhalable medicament to a targeted location within the respiratory system of a subject. The handheld inhalable medicament delivery devices described herein are configured to thermally modulate an inhalable medicament that is contained therein. Thermal modulation optimizes the droplet size of the inhalable medicament, wherein, typically, the higher the temperature (up to a threshold), the smaller the average drop size of an inhalable medicament. Also typically, the smaller the average drop size of an inhalable medicament, the further the inhalable medicament will travel through the respiratory tract. Therefore, making the drop sizes of an inhalable medicament smaller, for example, by heating them within the device, will cause the inhalable medicament to travel further along the respiratory tract of a subject than if the average droplet size was larger. The relationship of heating, to change in droplet size, to distance travelled within the respiratory tract, may be quantified so that the relationship is a predictable one. In this way, by controlling the droplet size of an inhalable medicament through thermal modulation, the devices and methods described herein determine the location in the respiratory tract where the inhalable medicament is primarily delivered.

In an embodiment of the medicament delivery device described herein, an inhaled medicament delivery device comprises a housing to receive a cartridge holding a liquid medicament in a reservoir. The cartridge includes a penetrable seal that retains the medicament inside the reservoir.

The housing may contain a hollow slideable reservoir tap within it, where the reservoir tap is configured to controllably advance forward to penetrate the seal of an attached cartridge.

The cartridge may be pressurized and further contain a compressed propellant gas. Once the penetrable seal is penetrated by the reservoir tap, the pressure difference between the pressurized cartridge and the hollow interior of the penetrating reservoir tap causes the propellant to expand and thereby eject the inhalable medicament into the reservoir tap, forming an aerosol.

The reservoir tap may be controllably retracted to stop the flow of the inhalable medicament out of the reservoir via the reservoir tap.

The seal of the device may comprise a self-sealing material.

The reservoir tap may comprise one or more ports that create a communication from the hollow interior of the reservoir tap to outside of the reservoir tap. The one or more ports are positioned on the reservoir tap so that one or more of the ports may enter the cartridge when the reservoir tap penetrates the cartridge seal. One or more ports may alternatively or additionally be positioned so that the ports are covered by the cartridge seal, either when the reservoir tap is drawn back after entering the cartridge or when the reservoir tap penetrates the cartridge.

When a port enters the cartridge, medicament is propelled through the port into the hollow interior of the reservoir tap. When the reservoir tap is drawn back from the interior of the cartridge, the seal may cover or block the port so that medicament is not able to enter the port, and thus is not able to further enter into the hollow portion of the reservoir tap.

The reservoir tap may include a first port and a second port that have different sizes. The different sizes of said first port and said second port can be configured to determine a dosing of said medicament. For example, in an embodiment where the smaller port is positioned closer to the tip of the reservoir tap than the larger port, the larger port may be covered by the seal when the reservoir tap penetrates a certain distance into the cartridge, thereby releasing a first dose into the hollow interior of the reservoir tap. The larger port may be located within the interior of the cartridge when the reservoir tap penetrates further into the cartridge, thereby releasing a second dose into the hollow interior of the reservoir tap, wherein the second dose is larger than the first dose.

Whether the medicament is to flow out of the reservoir via both the first port and the second port determines a flow rate for said medicament out of said reservoir.

In an embodiment, a device for delivering an inhalable medicament may further comprise an air flow amplifier that increases the flow of the inhalable medicament and/or air in the medicament mixture.

Also described herein is a cartridge for use with a device for delivering an inhalable medicament. A cartridge containing a liquid medicament may comprise a reservoir that retains the liquid medicament in a fixed position within the cartridge. The cartridge may further comprise a penetrable seal and a compressed propellant. The reservoir maintains the position of the liquid medicament between the compressed propellant and the seal, so that the compressed propellant is always behind the liquid medicament relative to the seal no matter the position of the cartridge.

The cartridge is configured to couple with a housing of a delivery device. The cartridge couples with the delivery device in such a way that the seal is positioned to be penetrated by an extendable reservoir tap of the medicament delivery device. The extendable reservoir tap is configured to penetrate the cartridge seal in order to allow the medicament to flow out of the cartridge when reservoir tap is extended.

In another embodiment, the delivery device described herein comprises or couples with a cartridge containing a reservoir. In an embodiment, a reservoir may comprise a bladder that contains a liquid medicament, and wherein the bladder may be compressed by the propellant to force the medicament out of the reservoir when the pressure inside the cartridge drops due to, for example, penetration of the cartridge seal.

In another embodiment, a reservoir may comprise a hydrophobic porous reservoir. The reservoir holds the medicament within its pores similar to a sponge. When the propellant forcefully expands due to a change in pressure, the propellant passes into the pores of the porous reservoir thereby displacing the medicament out of the reservoir. A propellant may displace the medicament out of the porous reservoir so that the medicament is aerosolized.

In an embodiment, the propellant may be dissolved in the medicament.

The propellant may comprise carbon dioxide dissolved in a medicament that includes miscible glycerol. The propellant may comprise carbon dioxide dissolved in a medicament that includes glycol.

In an embodiment, an inhaled medicament delivery device may further comprise an encapsulated neutralizing agent.

In another embodiment, an inhaled medicament delivery device may further comprise an absorbent material to render at least one active ingredient in the medicament unusable if said reservoir is breached via a part of said cartridge that is not said seal.

Also described herein is a method of delivering an inhaled medicament, comprising controllably extending a reservoir tap to penetrate a seal retaining a liquid medicament in a reservoir thereby allowing the medicament to flow out of the reservoir via a port in the reservoir tap. The method also includes controllably retracting the reservoir tap to stop the flow out of the reservoir via the reservoir tap by causing the port to become occluded by the cartridge seal.

In an embodiment, the method may further comprise controllably extending the reservoir tap a further amount into the container to allow the medicament to flow into a second port that was previously covered by a cartridge seal.

Controllably extending a reservoir tap may be initiated in response to, for example, the start of an inhalation cycle.

Controllably extending reservoir tap may allow a gas to flow into the second port while the medicament flows into the first port.

Also described herein is a method of providing a medicament to an inhaled medicament delivery device. The method comprises attaching a cartridge having a reservoir, a seal holding the medicament in said reservoir, and a propellant, wherein the medicament is held in said reservoir by said seal. The method also includes activating the inhaled medicament delivery device to penetrate the seal with a reservoir tap, and thereby allow the medicament to be propelled out of the reservoir by the propellant into the hollow interior of the reservoir tap.

The reservoir may comprise a bladder holding the medicament, the bladder being compressed by the propellant to force the medicament out of the reservoir. The reservoir may comprise a hydrophobic porous reservoir holding the medicament, where the propellant is to pass into pores of the porous reservoir, thereby displacing the medicament out of the reservoir and into the reservoir tap. A propellant that displaces the medicament out of the porous reservoir may cause the medicament to aerosolize.

Also described herein is a method for delivering an inhalable medicament to a subject, which comprises puncturing a seal on a cartridge, wherein the cartridge comprises a cartridge interior containing the inhalable medicament in liquid form. The method also includes forming an aerosol comprising the inhalable medicament by releasing the inhalable medicament into a conduit having an interior pressure that is lower than a pressure within the cartridge interior.

The method may further comprise heating the aerosol within the conduit and delivering the inhalable medicament to a subject through the conduit.

The puncturing or breaking of the seal creates a break in the seal that may be reversible and/or re-sealable.

The inhalable medicament may comprise an excipient.

The temperature of an aerosol may be modulated within the conduit into which the aerosol is delivered from the cartridge.

An aerosol may comprise particles having a Mass Median Aerodynamic Diameter (MMAD) of between 0.1 µm and 15 µm. An aerosol may comprise particles having a MMAD of 0.1 and 2 µm. As described herein, an inhalable medicament may be delivered into the respiratory or circulatory system of a subject. The average droplet size of an inhalable medicament comprising an aerosol typically will determine how far it will travel, or whether it will be expelled.

Described herein is a method of delivering an inhalable medicament to a target site of a subject, comprising forming an aerosol, which comprises a plurality of droplets of the inhalable medicament. The method also includes modulating a selectable temperature of the aerosol, wherein the temperature is selected to modify a size of at least one droplet of the plurality of droplets of the inhalable medicament. The method also includes delivering the temperature modulated aerosol to a subject. Wherein the size of at least one droplet of the plurality of droplets may be modified to be smaller than a size that will deposit in a target site. The size of at least one droplet of the plurality of droplets of the inhalable medicament may be modified to a size that causes pharyngeal or tracheal stimulation. The size of the at least one droplet of the plurality of droplets of the inhalable medicament may cause the at least one droplet of the plurality of droplets to be deposited in a mouth of a subject. The size of the at least one droplet of the plurality of droplets of the inhalable medicament may cause the at least one droplet of the plurality of droplets to be deposited in a trachea of a subject. The size of the at least one droplet of the plurality of droplets of the inhalable medicament causes the at least one droplet of the plurality of droplets to be deposited in an oropharynx of a subject. The size of the at least one droplet of the plurality of droplets of the inhalable medicament causes the at least one droplet of the plurality of droplets to be deposited in a lung of a subject. The size of the at least one droplet of the plurality of droplets of the inhalable medicament causes the at least one droplet of the plurality of droplets to be delivered to one or more lung lobes of a subject. The size of the at least one droplet of the plurality of droplets of the inhalable medicament causes the at least one droplet of the plurality of droplets to be delivered to a middle lung lobe of a subject. The size of the at least one droplet of the plurality of droplets of the inhalable medicament causes the at least one droplet of the plurality of droplets to be delivered to an inferior lung lobe of a subject.

The delivered aerosol may be flavored.

The aerosol may be delivered by way of a handheld device. The device may be configured to be integrated with a ventilator. As the device is orientation-independent it allows for downstream integration of the device regardless of patients orientation (elevated, supine, sitting, etc.).

Also described herein is an inhaled medicament delivery device, comprising a housing to receive a cartridge holding a liquid medicament in a reservoir, the cartridge including a seal that retains said medicament in said reservoir, and an extendable reservoir tap, the reservoir tap to controllably extend to penetrate the seal and allow the medicament to flow out of the reservoir via the reservoir tap and to controllably retract to stop said flow out of the reservoir via the reservoir tap.

In an embodiment, said seal is comprised of a self-sealing material. In an embodiment, said reservoir tap includes at least one port that is not occluded by the seal when the reservoir tap is extended to allow the medicament to flow out of the reservoir via the reservoir tap. In an embodiment, said at least one port is occluded by the seal when the reservoir tap is retracted to stop said flow out of the reservoir via the reservoir tap. In an embodiment, said reservoir tap includes a first port and a second port that have different sizes, a controllable extension of the reservoir tap determining whether the medicament is to flow out of the reservoir via the first port and not the second port and whether the medicament is to flow out of the reservoir via both the first port and the second port. In an embodiment, the different sizes of said first port and said second port determine a dosing of said medicament. In an embodiment, whether the medicament is to flow out of the reservoir via both the first port and the second port determines a flow rate for said medicament out of said reservoir. In an embodiment, the device further comprises an air flow amplifier to receive a first flow of said propellant to produce a second flow of air and propellant that is greater than said first flow.

Described herein is a method of delivering an inhaled medicament, comprising controllably extending a reservoir tap to penetrate a seal retaining a liquid medicament in a reservoir, thereby allowing the medicament to flow out of the reservoir via the reservoir tap, and controllably retracting the reservoir tap to stop the flow out of the reservoir via the reservoir tap. In an embodiment, the reservoir tap includes a first port and a second port and the reservoir tap is extended an amount that allows the medicament to flow into the first port and not to flow into the second port. In an embodiment, the method further comprises controllably extending the reservoir tap a further amount to allow the medicament to flow into the second port. In an embodiment, said controllably extending is initiated in response to a beginning of an inhaled cycle. In an embodiment, the method further comprises controllably extending the reservoir tap to allow a gas to flow into the second port while the medicament flows into the first port.

Described herein is an inhaled medicament delivery device, comprising an interface to releasably attach to a canister holding a liquid medicament in a reservoir, the canister including a seal that retains said medicament in said reservoir, and a hollow member to be activated to extend to a first extension within said canister, pierce the seal, and receive a flow of the medicament, the hollow member also to be deactivated to retract and stop the flow. In an embodiment, the hollow member is activated by electromagnetic force. In an embodiment, the hollow member is deactivated by a return spring. In an embodiment, when said hollow member is activated to a second extension within said canister, the hollow member receives a flow of a propellant. In an embodiment, said canister comprises the reservoir and a propellant cavity. In an embodiment, when said hollow member is activated to the first extension within said canister, a first port in the hollow member receives a flow of a propellant from the propellant cavity and a second port in the hollow member receives the flow of medicament from the reservoir. In an embodiment, when said hollow member is activated to a second extension within said canister, a first port in the hollow member receives a flow of a propellant from the propellant cavity and a second port in the hollow member is occluded to prevent the flow of medicament into the hollow member.

Described herein is a cartridge holding a liquid medicament, comprising a reservoir holding the liquid medicament, a housing configured to attach to a medicament delivery device, and a seal to retain the medicament in the reservoir, the housing holding the seal, the seal positioned to be penetrated by an extendable reservoir tap of the medicament delivery device, the extendable reservoir tap to allow the medicament to flow out of the reservoir when extended, and the seal to prevent the medicament from flowing out of the reservoir when the extendable reservoir tap is retracted. In an embodiment, the seal is comprised of a self-sealing material. In an embodiment, the extendable reservoir tap includes a first port and a second port to receive liquids, the seal to occlude the second port when the extendable reservoir tap is extended so that the second port does not pass a flow of the medicament. In an embodiment, the first port and the second port have different sizes, and a dimension of the seal is to determine whether the medicament is to flow out of the reservoir via the first port and not the second port or whether the medicament is to flow out of the reservoir via both the first port and the second port. In an embodiment, the different sizes of the first port and the second port are to determine a dosing of the medicament. In an embodiment, the occlusion of the second port is to determine a dosing of the medicament. In an embodiment, whether the second port is occluded by said seal is to determine a flow rate of said medicament out of said reservoir.

Described herein is a method of delivering an inhaled medicament, comprising receiving a controllably extended reservoir tap that penetrates a cartridge seal retaining a liquid medicament in a cartridge reservoir thereby allowing the medicament to flow out of the reservoir via the reservoir tap, and in response to a controlled retraction of the reservoir tap, stopping the flow out of the reservoir via the reservoir tap. In an embodiment, the reservoir tap includes a first port and a second port and the reservoir tap is extended an amount that allows the medicament to flow into the first port and not into the second port. In an embodiment, the method further comprises: receiving the reservoir tap when extended to a further amount that allows the medicament to flow into the second port. In an embodiment, the reservoir tap is controllably extended in response to a beginning of an inhalation cycle. In an embodiment, the cartridge is configured to allow a gas to flow into the second port while the medicament flows into the first port. In an embodiment, the method further comprises receiving a further extension of the reservoir tap that allows the medicament to flow into the first port while the gas flows into the second port.

Described herein is a cartridge for an inhaled medicament delivery device, comprising a canister holding a liquid medicament in a reservoir, the canister including a seal that retains said medicament in said reservoir, and an interface to releasably attach to the inhaled medicament delivery device, the interface configured to receive a hollow member from the inhaled medicament delivery device when the hollow member is activated to extend to a first extension within said canister, pierce the seal, and receive a flow of the medicament, the interface also configured to stop the flow of the medicament when the hollow member is retracted for deactivation. In an embodiment, the hollow member is activated by electromagnetic force. In an embodiment, the canister includes a return spring to deactivate the hollow member. In an embodiment, the interface can receive the hollow member when activated to a second extension within said canister, and when the hollow member is activated to the second extension, the canister provides the hollow member with a flow of a propellant. In an embodiment, said canister comprises the reservoir and a propellant cavity. In an embodiment, when said hollow member is activated to the first extension within said canister, a first port in the hollow member receives a flow of a propellant from the propellant cavity, and a second port in the hollow member receives the flow of medicament from the reservoir. In an embodiment, when said hollow member is activated to a second extension within said canister, a first port in the hollow member receives a flow of a propellant from the propellant cavity, and a second port in the hollow member is occluded by the cartridge to prevent the flow of medicament into the hollow member.

Described herein is an inhaled medicament delivery device, comprising a housing to receive a cartridge holding a liquid medicament in a reservoir, the cartridge including a seal and a propellant, and a reservoir tap, the reservoir tap to penetrate the seal and allow the medicament to be propelled out of the reservoir by the propellant and via the reservoir tap. In an embodiment, the reservoir comprises a bladder holding the medicament, the bladder compressed by the propellant to force the medicament out of the reservoir. In an embodiment, the reservoir comprises a hydrophobic porous reservoir holding the medicament, the propellant to pass into pores of the porous reservoir, thereby displacing the medicament out of the reservoir. In an embodiment, as the propellant displaces the medicament out of the porous reservoir, the medicament is aerosolized. In an embodiment, the propellant is dissolved in the medicament. In an embodiment, the propellant includes carbon dioxide dissolved in a medicament that includes miscible glycerol. In an embodiment, the propellant includes carbon dioxide dissolved in a medicament that includes glycol. In an embodiment, the device further comprises an encapsulated neutralizing agent. In an embodiment, the device further comprises an absorbent material to render at least one active ingredient in the medicament unusable if said reservoir is breached via a part of said cartridge that is not said seal.

Described herein is a method of providing a medicament to an inhaled medicament delivery device, comprising attaching a cartridge having a reservoir, a seal holding the medicament in said reservoir, and a propellant, the medicament held in said reservoir by said seal, and activating the inhaled medicament delivery device to penetrate the seal with a reservoir tap and allow the medicament to be propelled out of the reservoir by the propellant and via the reservoir tap. In an embodiment, the reservoir comprises a bladder holding the medicament, the bladder compressed by the propellant to force the medicament out of the reservoir. In an embodiment, the reservoir comprises a hydrophobic porous reservoir holding the medicament, and the propellant is to pass into pores of the porous reservoir, thereby displacing the medicament out of the reservoir and into the reservoir tap. In an embodiment, as the propellant displaces the medicament out of the porous reservoir the medicament is aerosolized. In an embodiment, the propellant is dissolved in the medicament. In an embodiment, the propellant includes carbon dioxide dissolved in a medicament that includes miscible glycerol.

Described herein is an inhalable medicament delivery device, comprising an interface to releasably attach to a cartridge holding a liquid medicament in a first reservoir and a propellant in a second reservoir, and a hollow member to be activated to extend to a first extension, thereby penetrating a seal and allowing the medicament to be propelled, via the hollow member, out of the first reservoir by a pressure provided by the propellant. In an embodiment, the hollow member is to be activated to extend to a second extension thereby allowing the propellant out of the second reservoir via the hollow member. In an embodiment, the first reservoir separates a neutralizing agent from said liquid medicament. In an embodiment, the hollow member penetrates the seal without releasing the neutralizing agent. In an embodiment, the first reservoir comprises a bladder holding the liquid medicament, the bladder compressed by the propellant in the second reservoir to force the medicament out of the first reservoir.

Described herein is a cartridge holding a liquid medicament, comprising: a cartridge housing to attach the cartridge to an inhaled medicament delivery device; a reservoir holding a liquid medicament; a propellant; and a seal holding the liquid medicament in the reservoir against a pressure provided by the propellant, the seal to be controllably penetrated by a reservoir tap of the inhaled medicament delivery device to allow the medicament to be propelled out of the reservoir by the propellant and via the reservoir tap. In an embodiment, the reservoir comprises a bladder holding the medicament, the bladder compressed by the propellant to force the medicament out of the reservoir. In an embodiment, the reservoir comprises a hydrophobic porous reservoir holding the medicament, the propellant to pass into pores of the porous reservoir thereby displacing the medicament out of the reservoir. In an embodiment, as the propellant displaces the medicament out of the porous reservoir, the medicament is aerosolized. In an embodiment, the propellant is dissolved in the medicament. In an embodiment, the propellant includes carbon dioxide dissolved in a medicament that includes miscible glycerol. In an embodiment, the propellant includes carbon dioxide dissolved in a medicament that includes glycol. In an embodiment, the cartridge further comprises an encapsulated neutralizing agent. In an embodiment, the cartridge further comprises an absorbent material to render at least one active ingredient in the medicament unusable if said reservoir is breached via a part of said cartridge that is not said seal.

Described herein is a method of providing a medicament to an inhaled medicament delivery device, comprising attaching a cartridge having a reservoir, a seal holding the medicament in said reservoir, and a propellant, the medicament held in said reservoir by said seal, and receiving a reservoir tap that penetrates the seal to allow the medicament to be propelled out of the reservoir by the propellant and via the reservoir tap. In an embodiment, the reservoir comprises a bladder holding the medicament, the bladder compressed by the propellant to force the medicament out of the reservoir. In an embodiment, the reservoir, comprising a hydrophobic porous reservoir holding the medicament and the propellant, is to pass into pores of the porous reservoir, thereby displacing the medicament out of the reservoir and into the reservoir tap. In an embodiment, as the propellant displaces the medicament out of the porous reservoir the medicament is aerosolized. In an embodiment, the propellant is dissolved in the medicament. In an embodiment, the propellant includes carbon dioxide dissolved in a medicament that includes miscible glycerol.

Described herein is a cartridge for an inhalable medicament delivery device, comprising: a first reservoir holding a liquid medicament, a second reservoir holding the propellant, and an interface to releasably attach to the inhalable medicament delivery device, the interface configured to receive a hollow member from the inhalable medicament delivery device, the hollow member to be activated to extend to a first extension thereby penetrating a seal of the cartridge and allowing the medicament to be propelled, via the hollow member, out of the first reservoir by a pressure provided by the propellant. In an embodiment, the interface is configured to allow the hollow member to be activated to a second extension, thereby allowing the propellant out of the second reservoir via the hollow member. In an embodiment, the first reservoir separates a neutralizing agent from said liquid medicament. In an embodiment, the hollow member penetrates the seal without releasing the neutralizing agent. In an embodiment, the first reservoir comprises a bladder holding the liquid medicament, the bladder compressed by the propellant in the second reservoir to force the medicament out of the first reservoir.

Described herein is a method for delivering an inhalable medicament to a subject, said method comprising: opening a seal on a cartridge, said cartridge comprising a cartridge interior, said cartridge interior containing said inhalable medicament in liquid form; forming an aerosol comprising said inhalable medicament by releasing said inhalable medicament into a conduit having an interior pressure that is lower than a pressure within said cartridge interior; heating said aerosol within said conduit; and delivering said inhalable medicament to said subject through said conduit. In an embodiment, said inhalable medicament comprises an excipient. In an embodiment, said opening the seal forms a passage in the seal that is re-sealable. In an embodiment, said opening the seal forms a puncture in the seal that is reversible. In an embodiment, a temperature of said aerosol is modulated within said conduit. In an embodiment, said aerosol comprises particles having a Mass Median Aerodynamic Diameter (MMAD) of between 0.5 µm and 5 µm. In an embodiment, said aerosol comprises particles having a MMAD of 0.1 and 2 µm. In an embodiment, said inhalable medicament is delivered to a lung of said subject. In an embodiment, said inhalable medicament is delivered into the circulatory system of said subject.

Described herein is an inhalable medicament delivery device, comprising: a seal opening member, the seal opening member comprising a first conduit that is to come into fluid communication with a reservoir interior that contains the inhalable medicament in liquid form; a nozzle in fluid communication with the first conduit, the nozzle forming an aerosol by releasing the inhalable medicament into a second conduit having an interior pressure that is lower than a pressure within the reservoir interior; a heater to heat the aerosol within the second conduit; and a mouthpiece to receive heated aerosol and deliver the heated aerosol to a subject. In an embodiment, after the first conduit comes into fluid communication with the reservoir interior, the seal opening member is to also deactivate and cut off fluid communication with the reservoir interior. In an embodiment, a temperature of said aerosol is modulated within said second conduit. In an embodiment, said nozzle produces the aerosol comprising particles having a Mass Median Aerodynamic Diameter (MMAD) of between 0.5 µm and 5 µm. In an embodiment, said nozzle produces the aerosol comprising particles a MMAD of 0.1 and 2 µm. In an embodiment, said aerosol is to be delivered to a lung of said subject. In an embodiment, said inhalable medicament is delivered into the circulatory system of said subject.

Described herein is an inhalable medicament container, comprising: a reservoir having a reservoir interior, the reservoir interior of the medicament container containing the inhalable medicament in liquid form; a seal configured to prevent the release of the medicament prior to an activation of a seal opening member, the seal configured to receive the seal opening member in order to release the medicament, the seal opening member comprising a first conduit that is to come into fluid communication with the reservoir interior; and, when activated, the seal opening member to be in fluid communication with a nozzle, the nozzle forming an aerosol by releasing the inhalable medicament into a second conduit having an interior pressure that is lower than a pressure within the reservoir interior, the aerosol to be heated within the second conduit and delivered to a subject. In an embodiment, after the first conduit comes into fluid communication with the reservoir interior, the seal opening member is to cooperate with the seal to deactivate and cut off fluid communication with the reservoir interior. In an embodiment, the container further comprises a propellant to provide the interior pressure. In an embodiment, the container further comprises a propellant to be mixed with the aerosol.

Described herein is a method of delivering an inhalable medicament to a target site of a subject, said method comprising: forming an aerosol comprising a plurality of droplets of said inhalable medicament; modulating a selectable temperature of said aerosol, wherein said temperature is selected to modify a size of at least one droplet of said plurality of droplets of said inhalable medicament; and delivering said temperature modulated aerosol to a subject. In an embodiment, said size of said at least one droplet of said plurality of droplets is modified to be smaller than a size that will deposit in a target site. In an embodiment, said size of said at least one droplet of said plurality of droplets of said inhalable medicament is modified to a size that causes tracheal stimulation. In an embodiment, said size of said at least one droplet of said plurality of droplets of said inhalable medicament causes said at least one droplet of said plurality of droplets to be deposited in the mouth of the subject. In an embodiment, said size of said at least one droplet of said plurality of droplets of said inhalable medicament causes said at least one droplet of said plurality of droplets to be deposited in the trachea of the subject. In an embodiment, said size of said at least one droplet of said plurality of droplets of said inhalable medicament causes said at least one droplet of said plurality of droplets to be deposited in the oropharynx of the subject. In an embodiment, said size of said at least one droplet of said plurality of droplets of said inhalable medicament causes said at least one droplet of said plurality of droplets to be deposited in a lung of the subject. In an embodiment, said size of said at least one droplet of said plurality of droplets of said inhalable medicament causes said at least one droplet of said plurality of droplets to be delivered to a superior lung lobe of the subject. In an embodiment, said size of said at least one droplet of said plurality of droplets of said inhalable medicament causes said at least one droplet of said plurality of droplets to be delivered to a middle lung lobe of the subject. In an embodiment, said size of said at least one droplet of said plurality of droplets of said inhalable medicament causes said at least one droplet of said plurality of droplets to be delivered to an inferior lung lobe of the subject. In an embodiment, said aerosol is flavored. In an embodiment, said aerosol is delivered through a handheld device.

Described herein is an inhalable medicament delivery device, comprising: an aerosol generator to form a first aerosol mixture comprising a first plurality of droplets of an inhalable medicament, the first plurality of droplets having a first size distribution; a thermal modulator to receive the first plurality of droplets and modify said first aerosol mixture to produce a second aerosol mixture comprising a second plurality of droplets of the inhalable medicament, the second plurality of droplets having a second size distribution; and a delivery passage to provide a subject with said second aerosol mixture. In an embodiment, said first aerosol mixture is modified such that said second size distribution includes droplets that are to be smaller than a size that will deposit in a target site. In an embodiment, said first aerosol mixture is modified such that said second size distribution includes droplets of a size that causes tracheal stimulation. In an embodiment, said first aerosol mixture is modified such that said second size distribution includes droplets of a size that causes droplets to be deposited in a mouth of the subject. In an embodiment, said size of said at least one droplet of said plurality of droplets of said inhalable medicament causes said at least one droplet of said plurality of droplets to be deposited in the trachea of the subject. In an embodiment, said size of said at least one droplet of said plurality of droplets of said inhalable medicament causes said at least one droplet of said plurality of droplets to be deposited in the oropharynx of the subject. In an embodiment, said size of said at least one droplet of said plurality of droplets of said inhalable medicament causes said at least one droplet of said plurality of droplets to be deposited in a target lobe of a lung of the subject.

Described herein is an inhalable medicament aerosol generator, comprising: a detachable reservoir having a reservoir interior and a propellant, the reservoir interior of the medicament container containing the inhalable medicament in liquid form, the propellant to force the liquid medicament out of the reservoir; an interface configured to receive the inhalable medicament from the reservoir for delivery to a subject; an aerosol generator to receive the inhalable medicament and form a first aerosol mixture comprising the propellant and a first plurality of droplets of the inhalable medicament, the first plurality of droplets having a first size distribution; a heated conduit to receive the first plurality of droplets and modify said first aerosol mixture to produce a second aerosol mixture comprising a second plurality of droplets of the inhalable medicament, the second plurality of droplets having a second size distribution; and a delivery passage to provide a subject with the second aerosol mixture. In an embodiment, said first aerosol mixture is modified such that said second size distribution includes droplets that are to be smaller than a size that will deposit in a target site.

Described herein is a method for delivering an inhalable medicament to a subject, said method comprising: receiving a seal opening member to place a first conduit into fluid communication with the contents of a reservoir, the contents of the reservoir including the inhalable medicament in liquid form, and providing the inhalable medicament to an aerosol generator via the first conduit, the aerosol generator forming an aerosol by releasing the inhalable medicament into a second conduit having an interior pressure that is lower than a pressure within the reservoir, the aerosol to be heated in the second conduit to form a heated aerosol, and the heated aerosol to be delivered to a subject. In an embodiment, said inhalable medicament comprises an excipient. In an embodiment, the seal opening member is repositioned to stop the fluid communication of the contents of the reservoir and the first conduit. In an embodiment, the seal opening member forms a puncture in a seal that is reversible. In an embodiment, a temperature of said aerosol is modulated within said second conduit. In an embodiment, said aerosol comprises particles having a Mass Median Aerodynamic Diameter (MMAD) up to 5 µm. In an embodiment, said aerosol comprises particles having a MMAD up to 2 µm. In an embodiment, said inhalable medicament is delivered to a lung of said subject. In an embodiment, said inhalable medicament is delivered into a circulatory system of said subject.

Described herein is an inhalable medicament reservoir, comprising: a reservoir having a reservoir interior holding an inhalable medicament in liquid form, the reservoir to provide the inhalable medicament to an aerosol-generating device, the aerosol-generating device to provide a seal opening member to open a seal of said reservoir and to provide a first conduit of the aerosol-generating device with the inhalable medicament for delivery to a nozzle in fluid communication with the first conduit, the nozzle forming a heated aerosol internal to the aerosol-generating device by releasing the inhalable medicament into a second conduit that is heated and also has an interior pressure that is lower that a pressure within the reservoir interior, and an interface to attach to the aerosol-generating device and to receive the seal opening member, the interface to include a conduit closing member to interface with the seal opening member to close the first conduit, such that the reservoir interior is not in fluid communication with the aerosol-generating device and the production of the heated aerosol is stopped. In an embodiment, after the first conduit is provided with the inhalable medicament for delivery to the nozzle, the seal opening member is to also deactivate and stop the production of the heated aerosol. In an embodiment, a temperature of said heated aerosol is to be modulated within said second conduit. In an embodiment, said nozzle produces the aerosol comprising particles having a Mass Median Aerodynamic Diameter (MMAD) of between 0.5 µm and 5 µm. In an embodiment, said nozzle produces the aerosol comprising particles a MMAD of 0.1 and 2 µm. In an embodiment, said aerosol is to be delivered to a lung of said subject. In an embodiment, said inhalable medicament is delivered into a circulatory system of said subject.

Described herein is an inhalable medicament container, comprising: a reservoir having a reservoir interior, the reservoir interior of the medicament container containing the inhalable medicament in liquid form; a seal configured to prevent the release of the medicament prior to an activation of a seal opening member, the seal configured to receive the seal opening member in order to release the medicament, the seal opening member comprising a first conduit that is to come into fluid communication with the reservoir interior; and, when activated, the seal opening member to be in fluid communication with a nozzle, the nozzle forming an aerosol by releasing the inhalable medicament into a second conduit having an interior pressure that is lower that a pressure within the reservoir interior, the aerosol to be heated within the second conduit and delivered to a subject. In an embodiment, after the first conduit comes into fluid communication with the reservoir interior, the seal opening member is to cooperate with the seal to deactivate and cut off fluid communication with the reservoir interior. In an embodiment, the container further comprises a propellant to provide the interior pressure. In an embodiment, the container further comprises a propellant to be mixed with the aerosol.

Described herein is a method of delivering an inhalable medicament, comprising: interfacing with an aerosol generator having a first conduit; engaging the first conduit to place the first conduit in fluid communication with the contents of a reservoir, the contents of the reservoir including the inhalable medicament in liquid form; and providing the inhalable medicament to the first conduit of the aerosol generator under pressure from a propellant, the pressure from the propellant causing the aerosol generator to form an aerosol comprising a plurality of droplets of said inhalable medicament, the propellant also causing a flow of said plurality of droplets through a selectable temperature conduit that is to modify a size of at least one droplet of said plurality of droplets of said inhalable medicament and is to deliver a temperature modulated aerosol to a subject. In an embodiment, said size of said at least one droplet of said plurality of droplets is modified to be smaller than a size that will deposit in a target site. In an embodiment, said size of said at least one droplet of said plurality of droplets of said inhalable medicament is modified to a size that causes tracheal stimulation. In an embodiment, said size of said at least one droplet of said plurality of droplets of said inhalable medicament causes said at least one droplet of said plurality of droplets to be deposited in the mouth of the subject. In an embodiment, said size of said at least one droplet of said plurality of droplets of said inhalable medicament causes said at least one droplet of said plurality of droplets to be deposited in the trachea of the subject. In an embodiment, said size of said at least one droplet of said plurality of droplets of said inhalable medicament causes said at least one droplet of said plurality of droplets to be deposited in the oropharynx of the subject. In an embodiment, said size of said at least one droplet of said plurality of droplets of said inhalable medicament causes said at least one droplet of said plurality of droplets to be deposited in a lung of the subject. In an embodiment, said aerosol comprises particles having a Mass Median Aerodynamic Diameter (MMAD) up to 5 µm. In an embodiment, said aerosol is flavored.

Described herein is an inhalable medicament reservoir, comprising a propellant and a reservoir having a reservoir interior holding an inhalable medicament in liquid form, the reservoir to provide the inhalable medicament to an aerosol-generating device, the aerosol-generating device to provide a seal opening member to open a seal of said reservoir and to provide a first conduit of the aerosol-generating device with the inhalable medicament for delivery to, under flow provided by the propellant, a nozzle in fluid communication with the first conduit, the nozzle forming a first aerosol mixture comprising a first plurality of droplets of the inhalable medicament, the first plurality of droplets having a first size distribution, the flow provided by the propellant to also move the first plurality of droplets into a thermal modulator where said first aerosol mixture is modified to produce a second aerosol mixture comprising a second plurality of droplets of the inhalable medicament, the second plurality of droplets having a second size distribution, the flow provided by the propellant to also aid in the delivery of the second aerosol mixture to a subject. In an embodiment, said first aerosol mixture is modified such that said second size distribution includes droplets that are to be smaller than a size that will deposit in a target site. In an embodiment, said first aerosol mixture is modified such that said second size distribution includes droplets of a size that causes tracheal stimulation. In an embodiment, said first aerosol mixture is modified such that said second size distribution includes droplets of a size that causes droplets to be deposited in the mouth of the subject. In an embodiment, said size of said at least one droplet of said plurality of droplets of said inhalable medicament causes said at least one droplet of said plurality of droplets to be deposited in the trachea of the subject. In an embodiment, said size of said at least one droplet of said plurality of droplets of said inhalable medicament causes said at least one droplet of said plurality of droplets to be deposited in the oropharynx of the subject. In an embodiment, said size of said at least one droplet of said plurality of droplets of said inhalable medicament causes said at least one droplet of said plurality of droplets to be deposited in a target lobe of a lung of the subject.

Described herein is an inhalable medicament container, comprising: a reservoir having a reservoir interior, the reservoir interior of the medicament container containing the inhalable medicament in liquid form; a propellant to force the liquid medicament out of the reservoir; and, an interface configured to deliver the inhalable medicament from the reservoir to a delivery device for delivery to a subject, the delivery device having an aerosol generator to form a first aerosol mixture comprising the propellant and a first plurality of droplets of the inhalable medicament, the first plurality of droplets having a first size distribution, the delivery device also having a thermal modulator to receive the first plurality of droplets and to modify said first aerosol mixture to produce a second aerosol mixture comprising a second plurality of droplets of the inhalable medicament, the second plurality of droplets having a second size distribution, the delivery device also having a delivery passage to provide a subject with said second aerosol mixture. In an embodiment, said second aerosol mixture is modified into a third aerosol mixture while in the oropharynx region, the third plurality of droplets having a third size distribution. In an embodiment, said second aerosol mixture is modified into a third aerosol mixture while in the lung airways region, the third plurality of droplets having a third size distribution.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 is a chart illustrating medicament flow rate.

FIG. 10C illustrates an isometric exploded view of a cartridge cover and cartridge for an inhalable medicament delivery device.

DETAILED DESCRIPTION

Figure 1A:
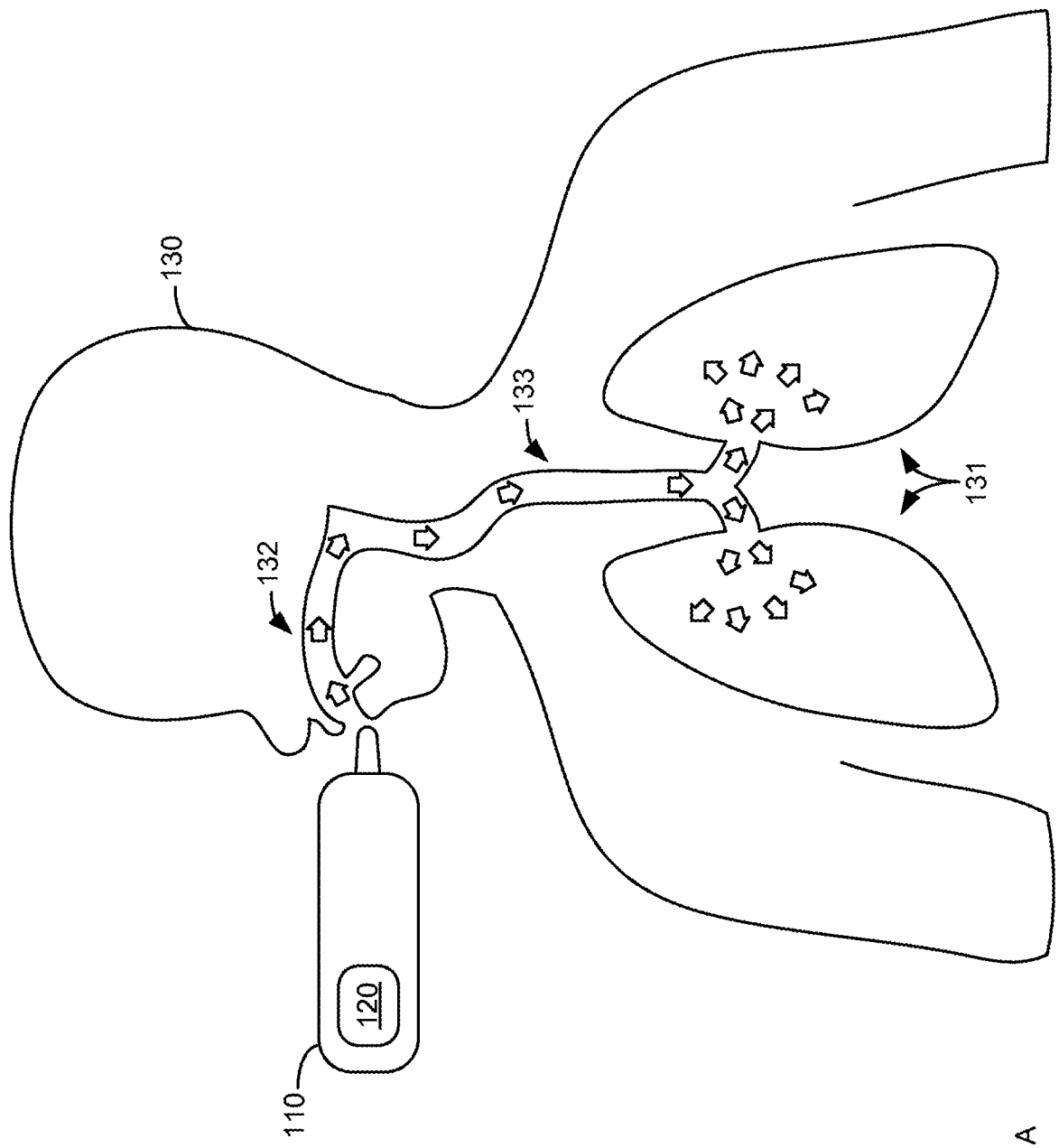
FIG. 1A illustrates the pulmonary delivery of an inhaled medicament.

Before describing the subject matter disclosed herein in detail, it is to be understood that the subject matter is not limited in its application to the details of construction, experiments, exemplary data, and/or the arrangement of the components set forth in the following description or illustrated in the drawings. The subject matter described herein is capable of other variations, and therefore the variations described herein should not be taken to limit the scope of the subject matter of the description in any way. Also, it is to be understood that the phraseology and terminology employed herein is for purpose of description only and should not be regarded as limiting in any way. In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The term "subject" as used herein may refer to a human subject or any animal subject.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Medicament Delivery Device

The devices and methods described herein may be configured to modify a particle size, mass, or distribution of an aerosol of an inhalable medicament in order to deliver the inhalable medicament to a specific target within the respiratory tract of a subject. The respiratory tract comprises upper and lower respiratory tract. The upper respiratory tract generally comprises the nose or nostrils, nasal cavity, mouth, throat (pharynx), and voice box (larynx). The lower respiratory tract generally comprises the trachea (windpipe), bronchial tubes, and lungs. The lungs are further anatomically and functionally divided on the right into an upper, mid, and lower lobes, and upper and lower lobes on the left. The airways continue to branch from the trachea segmentally until the terminal bronchioles and the alveoli, where gas exchange occurs with capillary blood. The modification of an average particle or droplet size of an inhaled medicament allows the medicament to be targeted to, for example, the lower lung. Which is to say that medicament is caused to travel through the mouth (or nose), through the oropharynx, through the trachea, through the bronchi, and into the lung. Medicament may be targeted to any part of the respiratory system by controlling the average size of the aerosol particle or droplet size. Generally, the smaller the aerosol particle or droplet, the farther into the respiratory tract the majority of the quantity of medicament will travel. However, if an aerosol particle is very small, it will simply be inhaled and subsequently exhaled and the medicament will not be delivered to any region of the airway.

Delivery of an inhaled medicament to a specific target within the respiratory tract is advantageous in general, because, for example, it delivers a concentrated dose of a medicament to a target rather than having the dose of medicament disperse throughout the respiratory tract. This is advantageous for treating, for example, a bacterial infection in the lung by directly delivering a dose of an inhalable antibiotic to the infected area. Targeted delivery may be advantageous for treating, for example, a loculated bacterial infection within the lung. In another example, the targeted delivery of a mucolytic in a patient with Cystic Fibrosis to the small airways, namely the bronchioles and bronchi, where the mucous plugging is most prevalent would be advantageous. Likewise, targeted delivery of a chemotherapeutic agent directly to a tumor in the respiratory tract may be achieved. Overall, targeted delivery allows for the delivery of lower drug loads to patients decreasing the risk and effects of drug toxicity, drug allergy, and side effects.

Additionally, the devices and methods described herein may be used to deliver a medicament into the circulatory system. Lung tissue comprises alveoli, which are cells that exchange oxygen and carbon dioxide with the circulatory system. Rich vascular networks surround the alveoli and are relatively permeable to exchange of gasses and particles. The device and method described herein provides a means for delivery of an inhaled medicament directly into the circulatory system. Namely, the devices and methods described herein are configured to selectably deliver an inhaled medicament to the alveoli of the lungs wherein the medicament is passed into the vascular network that surrounds the alveoli. The vascular network delivers the medicament to the heart through the pulmonary veins after which the inhaled medicament enters the systemic circulatory system.

Delivery of an inhaled medicament into the circulatory system is advantageous in general, because, for example, it provides an alternative mode of delivery of a medicament directly into the circulatory system. In contrast, medicaments delivered orally must first be digested before entering the circulatory system, which is a slow and unpredictable process. The digestive process causes a relatively unpredictable loss of dose through differences in gastrointestinal absorption and metabolism in different subjects (first-pass metabolism). Medicaments delivered intravenously require intravenous access, which can be difficult to obtain and predisposes the patient to risk of infection and other potential complications. Effective delivery of medicament into circulation via the respiratory system is advantageous for, for example, providing a rapid delivery of medicament directly into the circulatory system, such as in an emergency situation when an oral dose would take too long and no intravenous access is available. Effective delivery of medicament directly into the circulatory via the respiratory system is also advantageous for, for example, providing a means for a subject to take a medicament that is only formulated for intravenous delivery at home without requiring long term intravenous access or ports such as, for example, certain antibiotics or chemotherapeutic agents.

Described herein is a controllable inhaled medicament delivery device configured to generate inhalable aerosols, vaporized aerosols, and/or vapor-aerosol mixes. An aerosol particle size may be controlled by the device using thermal modulation. Typically, the size of an aerosol droplet decreases as it is heated.

FIG. 1A shows a schematic representation of the targeted delivery of an inhalable medicament with the delivery device described herein. The shown target of the medicament delivery is the mid lung. A hand held inhaled medicament delivery device 110 contains a medicament 120, and is operated by a subject 130. In the following discussions, the orientation of a device (e.g., inhaled medicament delivery device 110) is referred to in relation to the subject 130, such that the proximal end of the inhaled medicament delivery device 110 is closest to the subject 130 during the operation of the inhaled medicament delivery device 110 and the distal end of the inhaled medicament delivery device 110 lies away from the subject 130.

The inhaled medicament delivery device 110 comprises a housing and a mouthpiece. The outer shape of the housing may be formed into any shape including, for example, rectangular, cylindrical, or spheroid. Those having skill in the art will understand that any housing shape is suitable. In a preferred embodiment, the housing is shaped so that it is conveniently held in the hand of a subject 130. For example, in an embodiment, the housing of the inhaled medicament delivery device 110 is an elongate housing, wherein the length of the inhaled medicament delivery device 110 is larger than the width of the inhaled medicament delivery device 110. In an embodiment, the mouthpiece of the inhaled medicament delivery device 110 is continuous with the interior of the housing. In an embodiment, the interior of the mouthpiece is continuous with a hollow conduit that passes through the interior of the housing. A mouthpiece is typically smaller than the housing. For example, the diameter of a cylindrical mouthpiece is typically smaller than the diameter of a cylindrical housing. Likewise, for example, the width of a rectangular mouthpiece is smaller than width of a rectangular housing. It should be understood by those having skill in the art that a mouthpiece may also be of the same dimensions as the housing. In an embodiment, the mouthpiece is removably coupled with the housing of the inhaled medicament delivery device 110.

The housing of the inhaled medicament delivery device 110 may comprise a hard plastic or polymer material. In an embodiment, the housing of the inhaled medicament delivery device 110 comprises a metal or glass. In an embodiment, the housing comprises the same material as the housing. In an embodiment the mouthpiece comprises a material that will not irritate the mouth or convey an unpleasant sensation, such as, for example, a plastic or a thermoelastic polymer.

In an embodiment, the housing of the inhaled medicament delivery device 110 may not connect to a mouthpiece. In an embodiment, the subject 130 holds the housing either near or directly in contact with his or her mouth. In an embodiment, the housing is configured to couple with another conduit such as, for example, a venti mask.

In an embodiment, the housing may be configured to couple with an endotracheal or tracheostomy tube, face tent, breathing mask, or any other respiratory assistance device. The housing may be configured to directly couple with an endotracheal or tracheostomy tube, face tent, or breathing mask, or the housing may couple with adaptors that then couple with an endotracheal or tracheostomy tube, face tent, or breathing mask.

As shown by notional arrows, a medicament 120 is delivered into the airway of a subject 130 by the inhaled medicament delivery device 110. The medicament 120 travels into the subject's 130 mouth, upper airway 132, lower airways 133, and then into the targeted pulmonary parenchyma 131. Medicament 120 may be further delivered through the pulmonary vasculature of a subject 130, and into the systemic vasculature of a subject 130 when the subject 130 uses the inhaled medicament delivery device 110. During this progression, the inhaled formulation/mixture may be deposited (and thereby absorbed) in a region strongly influenced by the particle size and composition of the mixture.

While FIG. 1A shows an embodiment in which a medicament 120 travels into the pulmonary parenchyma 131, in other embodiments, the medicament 120 is delivered to another specific target. For example, the medicament 120 delivery may be targeted to the mouth. For example, the medicament 120 delivery may be targeted to the oropharynx. For example, the medicament 120 delivery may be targeted to the upper or lower airway. For example, the medicament 120 delivery may be targeted to a region of the lung such as the upper, mid, or lower lungs. For example, the medicament 120 delivery may be targeted to the pulmonary vasculature. Delivery of medicament 120 to specific targets is achieved by varying certain properties of the medicament 120 that is delivered to the subject 130 via the inhaled medicament delivery device 110. For example, the inhaled medicament delivery device 110 may heat an aerosolized medicament before it is delivered to a subject 130. Heating the aerosolized medicament 120 before it is delivered affects, for example, the aerosol particle size, wherein heating typically decreases the size of the aerosolized medicament 120 particles. Aerosol particles that are smaller typically travel further into the respiratory tract. For a range of particle sizes, the relationship of the size of the aerosol particle to the distance traveled through the airway is a direct relationship. However, particles that are smaller than a threshold amount will be exhaled relatively quickly. Thus, by controlling the size of an aerosol particle by, for example, applying heat to an aerosol, the distance that an aerosol travels may be controlled.

Similarly, for a range of aerosol temperatures, the amount of heat that is applied has a direct relationship to the amount in which a particle size is decreased. For this range, the greater the heat that is applied to an aerosol, the smaller the resulting particle. Outside of this range, applying more heat tends to increase particle size. That is, over a particular range of temperatures, the amount of heat applied to an aerosol is directly and predictably related to the size of the aerosol particle that is ultimately delivered by the inhaled medicament delivery device 110 into the airway of the subject 130. In this way, controlling the amount of heat applied to an aerosol by the inhaled medicament delivery device 110 determines how far into the respiratory tract that an aerosolized medicament 120 travels.

The aerosol generated by the inhaled medicament delivery device 110 may, for example, be moved to travel by a propellant gas. The aerosol may be caused to travel by a pressure differential, caused by, for example, the subject 130 inhaling the aerosol through an opening in the inhaled medicament delivery device 110, creating a negative pressure differential within the inhaled medicament delivery device 110 and the subject's 130 airway.

Generally, an inhalable medicament 120 generated by the inhaled medicament delivery device 110 may be delivered passively, actively, or a combination of both. In passive delivery, delivery may be caused or aided by the subject 130 inhaling or breathing in the medicament 120 aerosol. In active delivery, delivery of the inhalable medicament 120 may, for example, be delivered, entirely by the inhaled medicament delivery device 110, wherein the subject 130 does not aid delivery by inhaling or breathing in the medicament 120. Alternatively, the medicament 120 may be delivered by the combined action of the inhaled medicament delivery device 110 and the subject 130. For example, the inhaled medicament delivery device 110 may propel the aerosolized medicament 120 and the subject 130 may be instructed or caused to breath in the aerosolized medicament 120.

In an embodiment, the medicament 120 is stored in the inhaled medicament delivery device 110 as a liquid or viscous formulation.

Figure 1B:
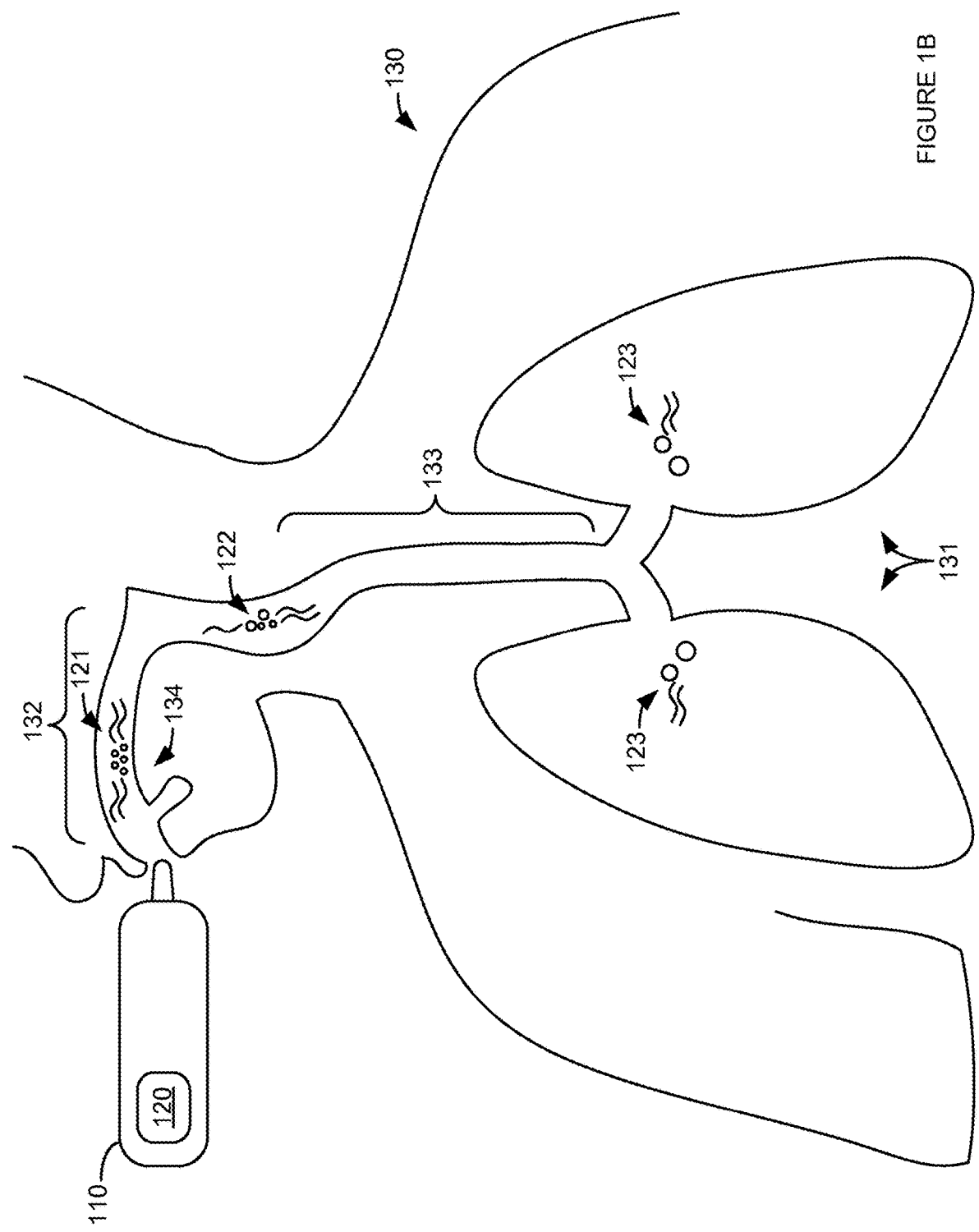
FIG. 1B illustrates an evolution of a vapor-aerosol mix during inhalation.

FIG. 1B shows an evolution of an aerosol during inhalation. In FIG. 1B, a subject 130 inhales, via an inhaled medicament delivery device 110, an aerosol comprising a medicament 120 into their mouth and oropharynx 132. Aerosol typically comprises droplets or particles that have a droplet or particle size of greater than or equal to 0.01 µm.

An aerosolized medicament may be delivered to a subject having a relatively uniform droplet size or as a mixture of different droplet sizes. In FIG. 1B, an aerosolized mixture 121 is comprised of a first amount of vapor (shown as wavy lines in FIG. 1B) and a second amount of aerosol having a second droplet size (shown as small circles in FIG. 1B). Depending upon the application, it should be understood that the aerosolized mixture 121 may include no vapor or no aerosol. However, for the purposes of this discussion, the aerosolized mixture 121 will be considered to include both vapor and aerosol droplets. As inhaled, the aerosolized mixture 121 is illustrated in FIG. 1B in the oropharynx 132. While in the region of the mouth and the oropharynx 132, a small amount of the aerosolized mixture 121 may contact the tongue 134. If the aerosolized mixture 121 contains a flavorant, contact with the tongue 134 or the oropharynx 132 will provide the subject 130 with a taste sensation.

As the aerosolized mixture 121 flows from the oropharynx 132 to the lung airways region 133, the aerosol and/or vapor properties of the aerosolized mixture 121 evolve (i.e., change). The evolution of the aerosolized mixture 121 may be caused (at least in part) by a cooling or heating of the aerosolized mixture 121 while in the respiratory tract. For example, a temperature change inside the airway of the subject 130 may occur as a result of warm or cold ambient air also being inhaled by the subject 130 with the aerosolized mixture 121. For example, the temperature change may occur as a result of interaction of the aerosolized mixture 121 with the body temperature of the subject 130. The evolution may be caused (at least in part) by the interaction of the aerosol droplets with each other over time (e.g., coagulation or the collision of lesser size particles causing the formation of larger particles).

Because the average droplet size of a vapor typically changes with a change in temperature, the evolution of the aerosolized mixture 121 within the airway of the subject 130 is expected to change the composition of particles or droplets within the aerosolized mixture 121. That is, after evolution of the aerosolized mixture 121 in oropharynx 132, the aerosolized mixture 121 may change to a mixture 122 as it travels in the region 133. The new mixture 122 in the region 133 is comprised of an aerosol having a third droplet size.

As mixture 121 evolves while traveling to become mixture 123 in the lungs 131, it should be understood to have a composition that may differ from the composition of mixtures 121 or 122.

Generally speaking, because the airways and lungs are moist, an average size of an aerosol particle, whether in a mixture of aerosol droplets or a homogenous aerosol, is expected to increase as the medicament 120 travels through airway. The amount of increase in aerosol particle size is further affected by physiologic factors such as, for example, body temperature or airway length. The amount of increase in aerosol particle size is further affected by, for example, the velocity of travel of the medicament 120 aerosol through the airway.

Figure 2A:
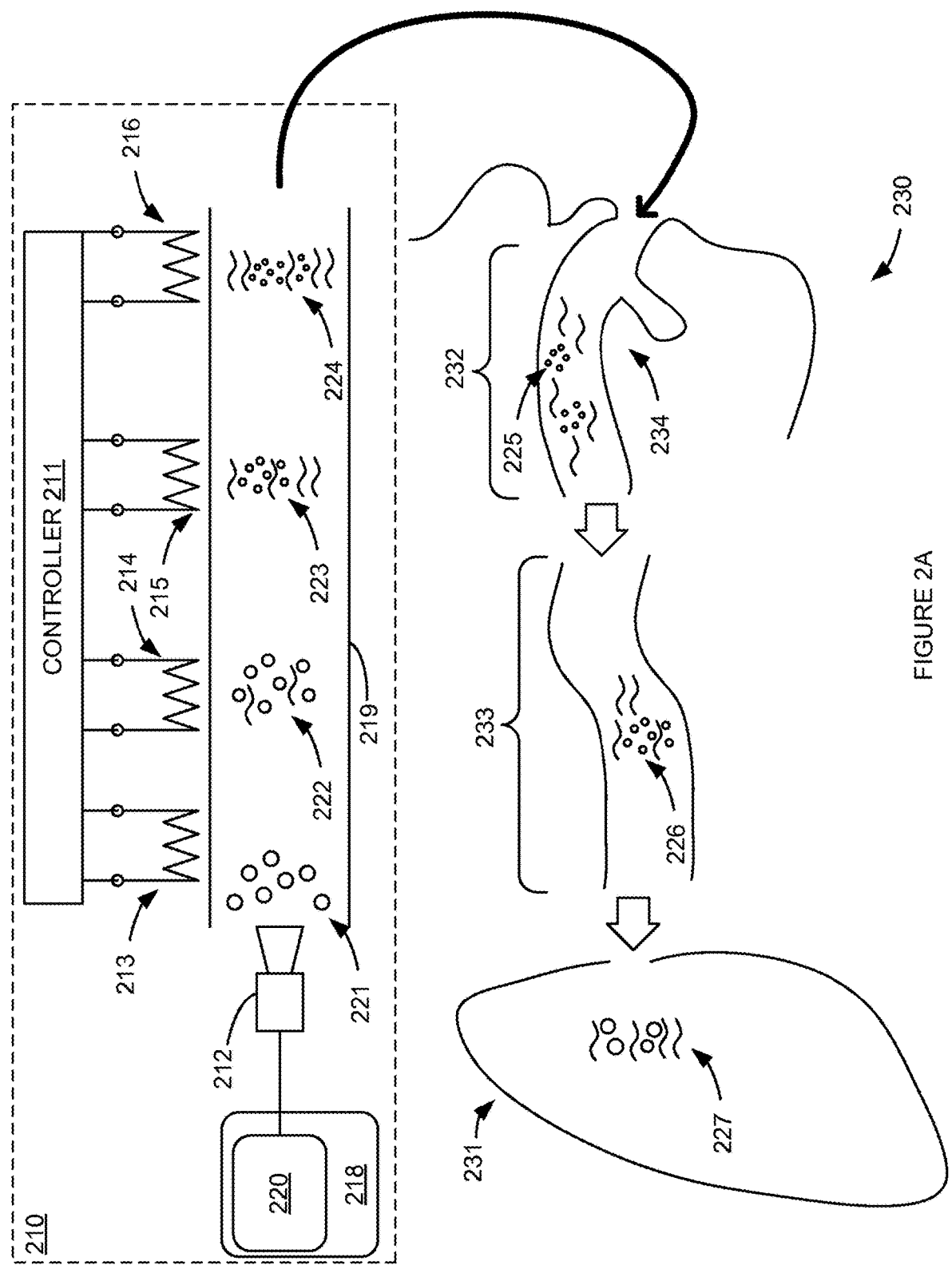
FIG. 2A is an illustration of thermal modulation and aerosol-vapor evolution during inhalation of a vapor-aerosol mix.

FIG. 2A shows a schematic view of both thermal modulation within an inhaled medicament delivery device 210 and aerosol evolution during inhalation of an aerosol mixture as it travels through the inhaled medicament delivery device 210 and through the airway. In the embodiment shown in FIG. 2A, the interior of the inhaled medicament delivery device 210 contains four heaters 213-216, but it should be understood that any number of heaters, or one single heater, or a heater or a plurality heaters thermally coupled with the aerosol nozzle, are suitable for use with the devices and methods described herein.

The inhaled medicament delivery device 210 may comprise an aspiration tube 219 through which the aerosol travels before passing through the mouth (or nose) of a subject 230. The inhaled medicament delivery device 210 may comprise a nozzle 212 that directs an aerosol into the aspiration tube 219. The inhaled medicament delivery device 210 may comprise or be coupled to a cartridge 218 that contains a liquid or viscous medicament within a reservoir 220.

The heaters 213-216 may be positioned in various positions relative to other components within the inhaled medicament delivery device 210. For example, the heaters 213-216 may be positioned near or surrounding the aspiration tube 219. For example, the heaters 213-216 may positioned near or surrounding the nozzle 212.

In an embodiment, zero, one, or more heaters are positioned near the aspiration tube 219, and zero, one, or more heaters are positioned near the nozzle 212. In an embodiment, the heaters 213-216 are positioned so that they apply heat to the entire circumference of a cylindrical conduit or the entire outer dimensions of a polygonal conduit, such as for example, the aspiration tube 219. In an embodiment, the heating element is positioned to apply heat to only one portion of the surface of a conduit.

In an embodiment, the heaters 213-216 comprise a heating element. A heating element may be made out of any suitable thermal conducting material. For example, a heating element may comprise a conductive metal or metal alloy such as titanium and titanium alloys, nickel or chromium, or nickel and chromium alloys. For example, a heating element may comprise ceramic. It should be understood that numerous thermal conducting materials are suitable for use with the devices and methods described herein and the examples provided are not to be taken as limiting in any way.

In an embodiment, a heating element is activated by an electric current that is passed through the element. The inherent resistance of the material creates heat when an electric current passes through the element. The temperature of the heating elements directly relates to the heat emitted by the heating elements and thus the heat emitted by the heaters 213-216. In addition, the electric current that is passed through the element may generate heat in the form of infrared radiation and function as an infrared emitter.

The temperature of the individual heaters 213-216 may be modulated by the inhaled medicament delivery device 210 through the controller 211. The heaters 213-216 may uniformly heat the entire length of a conduit such as, for example, the aspiration tube 219. The heaters 213-216 may be modulated so that they heat the aspiration tube 219 or the nozzle 212 segmentally, meaning that only a certain segment or certain segments of the aspiration tube 219 or the nozzle 212 may be heated by the individual heaters 213-216. For example, the aspiration tube 219 or the nozzle 212 may be heated over separate zones, each zone may, for example, be heated to a different temperature, and the temperature in each separate zone may be further modulated.

In an embodiment, temperature modulation control is achieved by a subject or healthcare provider via a user interface that is in communication with a controller 211. A user interface may be, for example, a digital user interface such as a touchscreen or, for example, a manual interface, or, for example, a combination of digital and manual elements. In an embodiment, a user interface may be directly attached to the housing of the inhaled medicament delivery device 210. In another embodiment, a user interface wirelessly communicates with the controller 211 on the inhaled medicament delivery device 210.

In another embodiment, temperature modulation is programmed into the controller 211 ahead of use by a subject 230. The temperature modulation programming may comprise an algorithm for modulating a temperature, and multiple algorithms comprising multiple temperature modulation variations may be stored on the controller 211 on a microprocessor memory. In an embodiment, the controller 211 is configured to activate different temperature modulations, and matches the optimal temperature modulation to the medicament being delivered via the inhaled medicament delivery device 210. For example, a particular temperature modulation may be optimal for a particular medicament, and the optimal temperature modulation is activated by the controller 211 when the particular medicament is used. When a different medicament having a different optimal temperature modulation associated with it is used, the controller 211 provides the proper temperature modulation that is associated with that medicament.

Temperature modulation of the heat applied by heaters 213-216 may also provide, for example, compensation for variability in environmental conditions. For example, if the ambient temperature is cold or warm, the temperature applied by the heaters 213-216 may be modulated to compensate for or balance against the effect of the cold or warm ambient temperature on the device and the inhalable medicament. Similarly, temperature modulation may, for example, compensate for a change in humidity by, for example, increasing or decreasing the degree of vapor of the inhalable medicament as described herein. Similarly, temperature modulation may, for example, compensate for a pressure induced temperature reduction within the nozzle 212 during aerosol generation.

A liquid medicament is held within a cartridge 218 within a reservoir 220. When either a reservoir tap or a penetrating nozzle 212 penetrates the cartridge 218, a compressed propellant within the cartridge 218 ejects the medicament from the reservoir 220 forming an aerosol. When either a reservoir tap or a penetrating nozzle 212 penetrates the cartridge 218, a compressed propellant within the cartridge 218 ejects the medicament from the reservoir 220, forming an aerosol. The formed aerosol 221 travels through the penetrating nozzle 212 and then into the aspiration tube 219. While the aerosol 221 travels through the aspiration tube 219, the aerosol 221 is heated or otherwise thermally modulated by heaters 213-216. When, the aerosol 221 is heated or otherwise thermally modulated by one or more of the heaters 213-216, one or more droplets within the aerosol 221 change size so that the overall composition of the aerosol 221 changes as it is heated. As the aerosol 221 travels along the aspiration tube 219, its composition changes in response to the application of heat or infrared radiation that is emitted by the heaters 213-216, and transforms into aerosol mixtures 222, then 223, and then 224. It should be understood that the schematic of FIG. 2A is exemplary only, and the aerosol 221 need not necessarily change in composition three times as it travels along the aspiration tube 219, and may in fact change in composition zero times or more as it travels along the aspiration tube 219. Additionally, the composition of the aerosol 221 may change in a homogenous or heterogeneous fashion.

Mixtures 221-224 may comprise both vapor and aerosol. Different droplet sizes are illustrated by small circles and wavy lines in the aerosol compositions shown in FIGS. 2A-2C. The vapor components in mixtures 221-227 may be illustrated by wavy lines in FIGS. 2A-2C. The differing number of wavy lines and small circles shown in mixtures 221-227 illustrate the varying amounts of vapor and aerosol present in the respective mixtures 221-227. The controller 211 controls heaters 213-216

After being thermally modulated in the aspiration tube 219 by the activation of one or more of heaters 213-216 by the controller 211, a mixture 225 is inhaled into the oropharynx 232 region by the subject 230. While in the oropharynx 232, the mixture 225 may contact the tongue 234 to provide the subject 230 with a taste sensation. In an embodiment, the medicament is mixed with a flavorant to provide, for example, a sweet taste to a subject 230 when the medicament comes into contact with the tongue 234 and oropharynx 232.

FIG. 2A shows the aerosol mixture 225 inhaled into the oropharynx 232 region by the subject 230. While in the oropharynx 232 region, the mixture 225 may contact the tongue 234 to provide the subject 230 with a taste sensation if the mixture 225 contains a flavorant. As the mixture 225 travels through the lower airway region 233, the aerosol and/or vapor properties of the mixture 225 evolve. The mixture 225 then flows to a distal airway region 231.

The evolution of the mixture 225 may be caused (at least in part) by a temperature change of the mixture 225. This temperature change may occur as a result of the mixture 225 with ambient air also being inhaled by the subject 230. This temperature change may occur as a result of interaction with the body temperature of the subject 230. The evolution may be caused (at least in part) by the interaction of the aerosol droplets with each other over time (e.g., collision of lesser size particles causing the formation of larger particles or the agglomeration of particles).

The mixture 225 in the oropharynx 232 evolves into the mixture 226 in the lower airway region 233. The mixture 226 is illustrated in the lower airway region 233 as having an amount of vapor and an amount of aerosol with a droplet size that is different from the mixture 225. The mixture 226 should be understood to be the mixture 225 after evolution that takes place while flowing from the oropharynx 232 and through the lower airway region 233.

The mixture 226 in the lower airway region 233 evolves into a mixture 227 in the distal airway region 231. The mixture 227 is illustrated in the distal airway region 231 as having an amount of vapor and an amount of aerosol with a droplet size that is different from the mixture 226. The mixture 227 should be understood to be the mixture 226 after evolution that takes place while flowing from the lower airway region 233 to the distal airway region 231.

As the mixture 225 flows from the oropharynx 232 to a lung distal airway region 231, the aerosol and/or vapor properties of the mixture 225 evolve. The mixture 225 flows to the lower airway region 233 and then to a more distal airway region 231 (shown by notional arrows in FIG. 2A).

The evolution of the mixture 225 may be caused (at least in part) by a temperature change of the mixture 225. This temperature change may occur as a result of the mixture 225 with ambient air also being inhaled by the subject 230. This temperature change may occur as a result of interaction with the body temperature of the subject 230. The evolution may be caused (at least in part) by the interaction of the aerosol droplets with each other over time (e.g., collision of lesser size particles causing the formation of larger particles, or the agglomeration of particles).

The mixture 225 in the oropharynx 232 evolves into the mixture 226 in the lower airway region 233. The mixture 226 is illustrated in lower airway region 233 as having an amount of vapor and an amount of aerosol with a droplet size that is different from the mixture 225. The mixture 226 should be understood to be the mixture 225 after evolution that takes place while flowing from the oropharynx 232 and through the lower airway region 233.

The mixture 226 in the lower airway region 233 evolves into the mixture 227 in a distal airway region 231. The mixture 227 is illustrated in a distal airway region 231 as having an amount of vapor and an amount of aerosol having a droplet size that is different from the mixture 226. The mixture 227 should be understood to be the mixture 226 after evolution that takes place while flowing from the lower airway region 233 to a distal airway region 231.

Figure 2B:
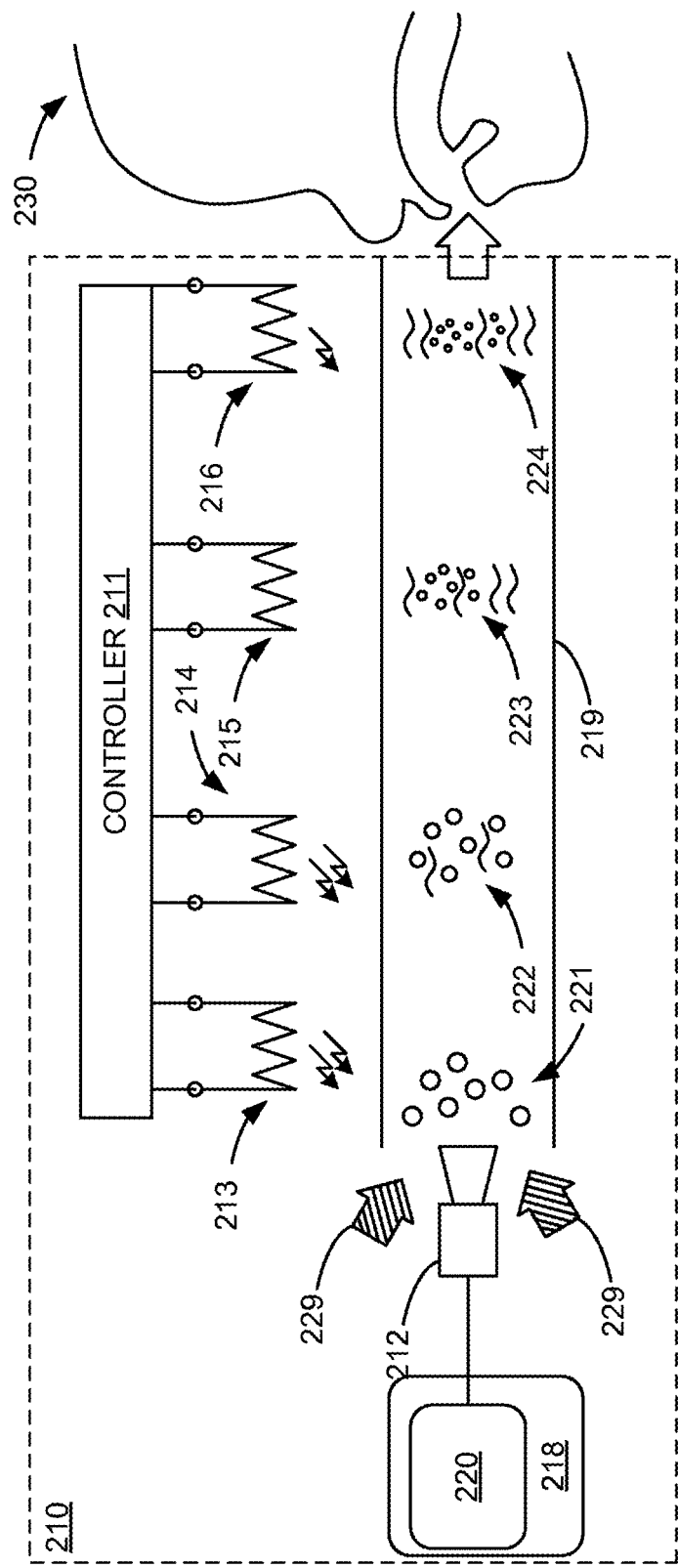
FIG. 2B is an illustration of air-mixture and thermal modulation.
Figure 2C:
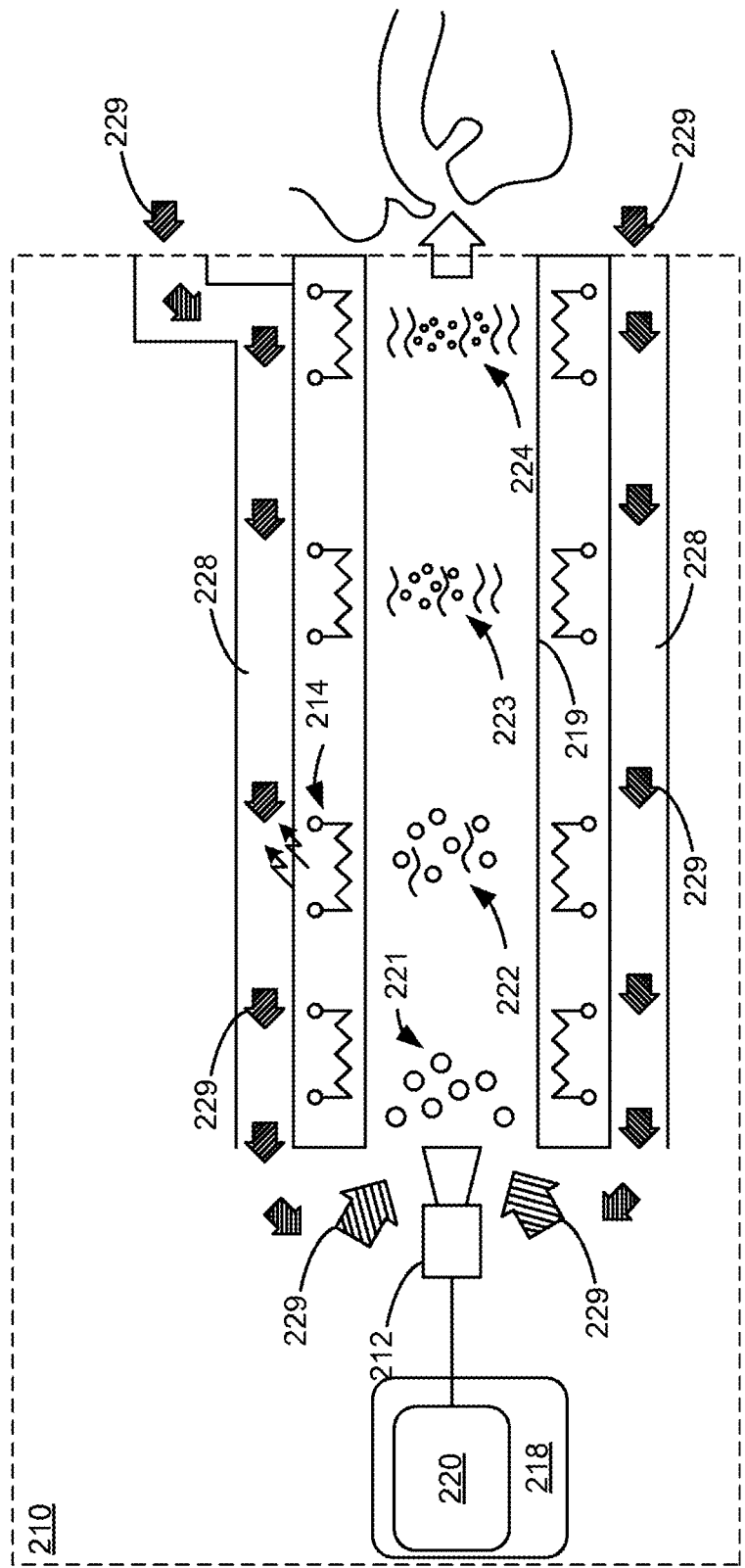
FIG. 2C is an illustration of a preheated air-mixture and thermal modulation.

FIG. 2B is an illustration of air-mixture and thermal modulation. In FIG. 2B, an inhaled medicament delivery device 210 comprises a reservoir 218, a medicament 220, a nozzle 212, a controller 211, heaters 213, 214, 215, 216, and an aspiration tube 219. The reservoir 218 holds the medicament 220. The reservoir 218 is operatively coupled to the nozzle 212 to provide the medicament 220 to the nozzle 212. The heaters 213-216 are operatively coupled to the controller 211. The nozzle 212 injects an aerosol mixture 221 into the aspiration tube 219. The injection of the aerosol mixture 221, or the inhalation of the subject 230 draws air 229 into the aspiration tube 219 to be mixed with the aerosol mixture 221. The injection of the aerosol mixture 221 may draw air 229 into aspiration tube 219 using an air flow amplifier configuration. Such an air flow amplifier configuration may utilize the Coanda effect to direct the flow of air 229, and/or the aerosol mixture 221, and/or propellant (not shown in FIG. 2B) in order to amplify the flow of air 229 and the mixtures 221-224 through the aspiration tube 219.

The aerosol mixture 221 is heated, or otherwise thermally modulated, by one or more of the heaters 213-216 to produce the mixtures 222-224. The mixtures 221-224 are comprised of vapor and aerosol. The vapor components in the mixtures 221-227 are illustrated by wavy lines in FIGS. 2A-2C. The aerosol components in the mixtures 221-227 are illustrated as small circles in FIGS. 2A-2C. The differing number of wavy lines and small circles shown in mixtures 221-227 illustrate the varying amounts of vapor and aerosol present in the respective mixtures 221-227. The controller 211 controls the heaters 213-216.

The inhaled medicament delivery device 210 may generate a partial or complete vapor from the aerosolized medicament 220. A partial vapor may, for example, be mixed with an aerosol. The particle size of the medicament 220 is smaller in the vapor than in the aerosol. The variation in the particle size of the medicament 220 can be controlled by, for example, controlling the degree of vaporization. For example, a complete vapor will deliver a smaller particle size medicament 220 than the medicament 220 particle delivered by an aerosol.

The degree of vaporization of the aerosolized medicament 220 increases with an increase in the amount of heat applied. Thus, the hotter the aerosolized medicament 220 becomes, the greater the quantity and speed of vapor generation inside the inhaled medicament delivery device 210.

Variations of the inhaled medicament delivery device 210 with respect to partial and complete vapor generation from the aerosolized medicament 220 are described herein.

FIG. 2B shows a schematic view of the actions of the heaters 213-216. Activated heaters 213-216, that are actively emitting heat, are illustrated in FIG. 2B by one or more small 'thermal radiation' (i.e., 'z' shaped) arrows in proximity to a respective heater 213-216. The selective presence or absence of such arrows in the schematic representation of the heaters 213-216 is meant to illustrate controllable thermal modulation of heating along the aspiration tube 219. That is, as shown, the controller 211 may, for example, cause the heaters 213, 214, and 216, to emit heat along the aspiration tube 219, while the heater 215 is not activated by the controller 211. It should be understood that through the controller 211, the heaters 213-216 may be sequentially controlled in any number of ways including but not limited to control over individual heater activation, control over individual heater activation timing, and control over individual heater activation duration.

The mixture 222 is illustrated in FIG. 2B as having, for example, more vapor and a smaller droplet size relative to the mixture 221. The mixture 222 is thermally modulated into the mixture 223. The mixture 223 is illustrated in FIG. 2B as having, for example, more vapor and a smaller droplet size relative to the mixture 222. The mixture 223 is thermally modulated into the mixture 224. The mixture 224 is illustrated in FIG. 2B as having, for example, more vapor and a smaller droplet size relative to the mixture 223. Mixture 224 is inhaled by the subject 230. It should be understood that any of the mixtures 221-224 may comprise vapor mixed with aerosol or a mixture of different sized aerosol drops.

Thermal modulation may also be used in order to convey a warm aerosol or vapor to the subject 230 to replicate a sensory cue or sensation of inhaling smoke. Furthermore, a warm aerosol or vapor that is of the same or similar to the physiologic temperature of the airway may be used in order to convey a more pleasant aerosol or vapor for inhalation, reducing patient resistance to inhalation of the aerosol and concurrently improving the delivery of the medicament 220.

FIG. 2C is an illustration of preheated air-mixture and thermal modulation. In FIG. 2C, an inhaled medicament delivery device 210 comprises a reservoir 218, a medicament 220, a nozzle 212, a heater 214, and an aspiration tube 219. The reservoir 218 holds the medicament 220. The reservoir 220 is operatively coupled to the nozzle 212 to provide the medicament 220 to the nozzle 212. The heaters 213-216 are operatively coupled to the controller 211. The nozzle 212 injects an aerosol mixture 221 into the aspiration tube 219. The injection of the aerosol mixture 221, or the inhalation of the subject 230, draws air 229 along a passageway 228 and then into the aspiration tube 219 to be mixed with the aerosol mixture 221. As the air 229 is drawn along the passageway 228, the air 229 is heated. The air 229 may be heated by a heater 214 or other heaters (not shown in FIG. 2C). The air 229 may be heated by contact or proximity to the aspiration tube 219, which is heated by at least the heater 214. The passageway 228 may be configured such that the air 229 does not contact the heater 214 elements. For example, the passageway 228 may be configured on the outside surface of the aspiration tube 219 such that the aspiration tube 219 (or another barrier) separates the heater 214 from the air 229.

FIG. 3A shows a medicament cartridge 340 and a reservoir tap 312 as they are positioned relative to one another in an embodiment of an inhaled medicament delivery device 310. More specifically, FIG. 3A shows the medicament cartridge 340 and the reservoir tap 312 positioned at the distal end of the inhaled medicament delivery device 310 (only distal end of the inhaled medicament delivery device 310 is shown). The medicament cartridge 340 is coupled to a housing that contains the reservoir tap 312 within it. The reservoir tap 312 is configured to slideably move along a length of the inside of the housing.

The medicament cartridge 340 comprises a porous reservoir material 342, a medicament 320, and a cartridge seal 343. The reservoir tap 312 comprises a tap shaft 353 and a nozzle 352. The tap shaft 353 has a hollow interior and includes ports 355 that allow liquids or gasses to flow from outside the reservoir tap 312 into the tap shaft 353. The hollow interior of the tap shaft 353 is continuous with the nozzle 352 so that liquids or gasses passed into the interior of the tap shaft 355 flow freely into the nozzle 352. The medicament cartridge 340 may be separable and re-attachable from the inhaled medicament delivery device 310.

In an embodiment, the inhaled medicament delivery device 310 comprises two or more couplable hollow bodies. In the shown embodiment, inhaled medicament delivery device 310 comprises two hollow bodies that are coupled so that the interior of the first body is separated from the interior of the second body. The interiors of the two coupled bodies of the inhaled medicament delivery device 310 may be separated by a penetrable seal 343. In an embodiment, the inhaled medicament delivery device 310 comprises a medicament cartridge 340 that contains an inhalable medicament and the body that the medicament cartridge 340 couples with comprises a hollow housing containing the reservoir tap 312.

In an embodiment, the two hollow bodies are reversibly coupled via a coupling mechanism. A coupling mechanism may comprise a screw-in system wherein both bodies have interlocking threaded sections that screw together to secure the two bodies together. A coupling mechanism may comprise a clip-in mechanism where one or more male appendage on a first hollow body lock into one or more female appendages on a second hollow body, so that the male and female appendages lock together. It should be understood that other coupling mechanisms for interlocking two hollow bodies that couple together are suitable for use with the devices and methods described herein and the examples above is not to be understood as limiting in any way.

In an embodiment, a reversibly coupled medicament cartridge 340 may be disconnected from the inhaled medicament delivery device 310. For example, after the medicament 320 is dispensed to a subject, an expended cartridge may be disconnected from the inhaled medicament delivery device 310. A plurality of the medicament cartridges 340 may be interchanged using the coupling mechanism to couple and then de-couple the medicament cartridges 340 of the plurality of medicament cartridges 340. A plurality of the medicament cartridges 340 that may be interchangeably coupled with the inhaled medicament delivery device 310 may contain the same medicament 320. The medicament cartridges 340 that may be interchangeably coupled with the inhaled medicament delivery device 310 may contain different medicaments 320. In an embodiment, the inhaled medicament delivery device 310 self-sterilizes between the exchange of two different reversibly couplable medicament cartridges 340 in order to, for example, prevent cross-contamination of different medicaments 320 or different cartridge loads. Self-sterilization of the inhaled medicament delivery device 310 may occur through activation of one or more heaters to a temperature adequate to sterilize the inhaled medicament delivery device 310. Alternatively or additionally, components that contact the medicament 320 may be exchanged when the medicament cartridge 340 is exchanged for a new cartridge, such as, for example, exchanging the aspiration tube (not shown) or the mouthpiece or the reservoir tap 312 along with exchanging the medicament cartridge 340. In an embodiment, the medicament cartridge 340 may be replaced with one or more cartirdges adapted to clean and sterilize the inhaled medicament delivery device 310. Such a cartridge or cartridges may flush components that contact the medicament with water, solvents, sterilizing agents, drying agents, and/or lubricants to restore optimal device operation and/or prevent cross-contamination, etc.

In an embodiment, the inhaled medicament delivery device 310 comprises a medicament cartridge 340 that is continuous with a housing that contains the reservoir tap 312. That is, the medicament cartridge 340 and the housing are formed as a single unit rather than two components that are coupled together with a mechanical coupling mechanism. In this embodiment, the medicament cartridge 340 is not configured to be decoupled from the inhaled medicament delivery device 310.

In an embodiment, a medicament cartridge 340 is configured to be reversibly coupled with a housing of an inhaled medicament delivery device 310 and is disposable.

In an embodiment, a medicament cartridge 340 is refillable and reusable.

In an embodiment, the entire inhaled medicament delivery device 310, including the medicament cartridge 340 along with the housing, is disposable.

In an embodiment, a reservoir tap 312 comprises a hollow body with a penetrating tip. The penetrating tip may be, for example, sharp, or, for example, blunt. The reservoir tap 312 may be advanced towards the seal 343 or withdrawn away from the seal 343 within the inhaled medicament delivery device 310 housing. For example, movement of the reservoir tap 312 may occur on an axis that is parallel to the long axis of the inhaled medicament delivery device 310 housing or a conduit within the housing that contains the reservoir tap 312.

In an embodiment, a first hollow body of the inhaled medicament delivery device 310, comprising the cartridge 340, couples with a second hollow body of the inhaled medicament delivery device 310 that contains the reservoir tap 312 within it, so that the penetrating tip of the reservoir tap 312 faces the surface of the penetrable seal 343.

In an embodiment, the reservoir tap 312 includes one or more ports 355. In an embodiment, the reservoir tap 312 is configured to be advanced so that the penetrating body of the reservoir tap 312 penetrates a penetrable seal 343. The reservoir tap 312 is advanced so that when the seal 343 is penetrated, one or more ports 355 is positioned either within the medicament cartridge 340 or positioned within the penetrated seal 343, so that the port 355 within the seal 343 is covered by the seal 343. In the inactivated position, the seal 343 is not penetrated a by tap shaft 353 (or at least not penetrated or configured such that medicament 320 is allowed to flow into reservoir tap 312).

In an embodiment, the ports 355 are covered while the reservoir tap 312 is entirely within the housing and are uncovered once the reservoir tap 312 penetrates the seal 343. For example, in an embodiment, the reservoir tap 312 comprises two rotating portions each with ports 355 that are configured to align, and wherein one rotating portion is within the other. When both rotating portions of the reservoir tap 312 rotate to align the ports, the ports 355 are open.

When both rotating portions of the reservoir tap 312 are rotated so that their respective ports 355 are not aligned, the ports 355 are covered. In another example, in an embodiment, the ports 355 are covered by a slideably removable cover that is pulled back when or after the reservoir tap 312 penetrates the seal 343.

In an embodiment, the medicament cartridge 340 contains a porous reservoir 342, which contains a medicament 320, and a propellant gas 341. In the embodiment shown, the porous reservoir 342 comprises a hydrophobic material, such as, for example, a hydrophobic polymer comprising of pores or channels, or for example a hydrophobic porous ceramic. The medicament 320 in liquid form is retained by hydrophobic forces within the pores of the porous reservoir material 342. The entire medicament cartridge 340 is pressurized so that the propellant gas 341 is compressed and is substantially prevented from passing through the pores or channels of the porous reservoir material 342 while the medicament cartridge 340 is pressurized. In an embodiment, the medicament cartridge 340 is enclosed on all but one side by a housing, and the opening in the medicament cartridge 340 is sealed by the penetrable seal 343. The term "cartridge" may refer to the entire distal assembly which includes the medicament cartridge 340, the liquid reservoir, and other components. The term "cartridge" may refer to the part of the inhaled medicament delivery device 310 or cartridge that contains the pressurized gas or just the medicament 320. The medicament cartridge 340 is sealed by a valve assembly and or a septum.

In an embodiment, the porous reservoir material 342 comprises a porous or matrix material that is hydrophobic and is configured to retain a liquid medicament formulation through capillary action or similar means in void spaces in the matrix or pores in the porous reservoir material 342. Materials such as ceramics, glasses, polymers, or plastics may be suitable for use as the porous reservoir material 342. Non-limiting examples of hydrophobic polymer materials include Acrylics, Amides, Carbonates, Dienes, Esters, Ethers, Fluorocarbons, Olefins, Styrenes, Vinyl Acetals, Vinyl Esters, and Vinylpyridine. The porous reservoir material 342 may comprise, for example, a matrix or honeycomb structure. In an embodiment, the porous reservoir material 342 is positioned between the propellant gas 341 and the penetrable seal 343. The propellant gas 341 may pass into the pores of the porous reservoir material 342, while the hydrophobic property of the porous reservoir material 342 holds or traps the fluid within the pores of the porous reservoir material 342. The fluid held within the pores of the porous reservoir material 342 is analogous to water held within a sponge. When the pressure in the medicament cartridge 340 equilibrates with ambient pressure because, for example, the seal 343 was penetrated, the propellant gas 341 forcefully expands into the pores of the porous reservoir material 342. The forceful expansion of the propellant gas 341 ejects the fluid medicament 320 out of the pores of the porous reservoir material 342.

In an embodiment, the porous reservoir material 342 allows for the inhaled medicament delivery device 310 to be operated regardless of orientation. The orientation-independent operation of the inhaled medicament delivery device 310 is achieved because the liquid formulation of the medicament 320 is always maintained in the same position relative to the compressed propellant gas 341. That is, the medicament 320 is always maintained in a proximal position to the port or ports 355 when the reservoir tap 312 penetrates the penetrable seal 343, and the compressed propellant gas 341 is always positioned distal to the reservoir tap 312 relative to the position of the medicament 320. Said yet another way, the propellant gas 341 is always behind the medicament 320, relative to the reservoir tap 312, regardless of how the subject positions the inhaled medicament delivery device 310 relative to their mouth. Because the fluid is held in place by, for example, the porous reservoir material 342, a subject can use the inhaled medicament delivery device 310 while, for example, lying on their back with the medicament cartridge 340, for example, towards the ceiling. Because the device may be used by a subject in the prone or sitting positions, the orientation-independence of the inhaled medicament delivery device 310 is advantageous to, for example, provide an inhalable medicament 320 to a bed-bound patient with poor mobility. It should be understood that there are other variations that can facilitate the holding of the fluid within the medicament cartridge 340 in a fixed position within the medicament cartridge 340, and the examples and embodiments described herein should not be understood to be limiting in any way.

In an embodiment, the penetrable seal 343 comprises rubber. In an embodiment, the penetrable seal 343 comprises a plastic. In an embodiment, the seal 343 comprises a polymer. It should be understood that other materials are suitable for construction of a penetrable seal 343 and the examples above should not be taken to be limiting. In an embodiment, the penetrable seal 343 is self-sealing, so that after being punctured the puncture in the penetrable seal 343 closes by itself due to, for example, the elastic properties of the seal 343 material. The seal 343 functions to create an airtight seal 343 of the medicament cartridge 340 to maintain the pressurization within the medicament cartridge 340. When the seal 343 is punctured by the reservoir tap 312, the pressure within the medicament cartridge 343 equilibrates with ambient pressure. Non-limiting examples of suitable seal 343 materials include Silicone Rubber, Polyacrylate Rubber, Ethylene-acrylate Rubber, Polyester Urethane, Bromo Isobutylene Isoprene, Chloro Isobutylene Isoprene, Chlorosulphonated Polyethylene, Polyether Urethane, Fluoro Silicone, and Vinyl Methyl Silicone. The seal 343 material may, in an embodiment, contain a metal imbedded in the material such as silver or copper to prevent the growth of microorganisms on the seal or another suitable antimicrobial agent imbedded into the seal 343 material. In an embodiment, the seal 343 is comprised of a self-healing material. The seal 343 allows for the tap shaft 353 to slide along the proximal to distal direction (and back). In an embodiment, the second body that contains the reservoir tap 312 is also sealed with a penetrable seal 343.

In an embodiment, the medicament cartridge 340 may contain a propellant gas 341 such as carbon dioxide ($CO_2$). The propellant gas 341 may be compressed within the medicament cartridge 340 when, for example, the medicament cartridge 340 is pressurized. A decrease in pressure inside of the medicament cartridge 340 will, for example, result in an expansion of the propellant gas 341 into the pores of the porous reservoir material 342.

The propellant gas 341 is held in the medicament cartridge 340 under pressure such as to provide a positive pressure that can drive the medicament 320 in the medicament cartridge 340 out of the medicament cartridge 340 and through the nozzle 352 to generate an aerosol. Interior to the medicament cartridge 340 is the porous reservoir material 342 that occupies a proximal area of the medicament cartridge 340. The porous reservoir material 342 serves to hold, retain, or otherwise trap the liquid formulation of the medicament 320. The porous reservoir material 342 serves to hold the medicament 320 such a manner that when the inhaled medicament delivery device 310 is activated, the propellant gas 341 will be forced through the porous reservoir material 342 and as a result, displace the liquid medicament 320 out of the porous reservoir material 342 for delivery to the tap shaft 353 and then to the nozzle 352. The medicament cartridge 340 comprises propellant gas 341, and is the portion that is typically located most distally along the inhaled medicament delivery device 310 from the mouthpiece. The porous reservoir material 342 may be positioned adjacent to the medicament cartridge 340, and the pores of the porous reservoir material 342 may communicate with the interior of the medicament cartridge 340 so that, for example, a propellant gas 341 may pass from the medicament cartridge 340 and into the pores of the porous reservoir material 342.

In an embodiment, the porous reservoir material 342 may be omitted where the liquid formulation of the medicament 320 is brought into a miscible solution with the propellant gas 341.

When the inhaled medicament delivery device 310 is not activated, the ports 355 on the tap shaft 353 can be occluded or otherwise blocked by the seal 343. When the reservoir tap 312 is activated to move in the distal direction far enough that the reservoir tap 312 penetrates the penetrable seal 343, and the ports 355 exit the seal 343 and enter the medicament cartridge 340, the liquid formulation of the medicament 320 enters the ports 355, travels through the tap shaft 353, and exits the nozzle 352.

The movement of the reservoir tap 312 may be driven and controlled in a number of ways, including the following non-limiting examples. The movement of the reservoir tap 312 may be, for example, spring driven. The movement of the reservoir tap 312 may be, for example, driven by electromagnetic forces. The movement of the reservoir tap 312 may be, for example, driven by pressurized air or gas. The movement of the reservoir tap 312 may be, for example, driven by an electromechanical actuator or servo.

Figure 3A:
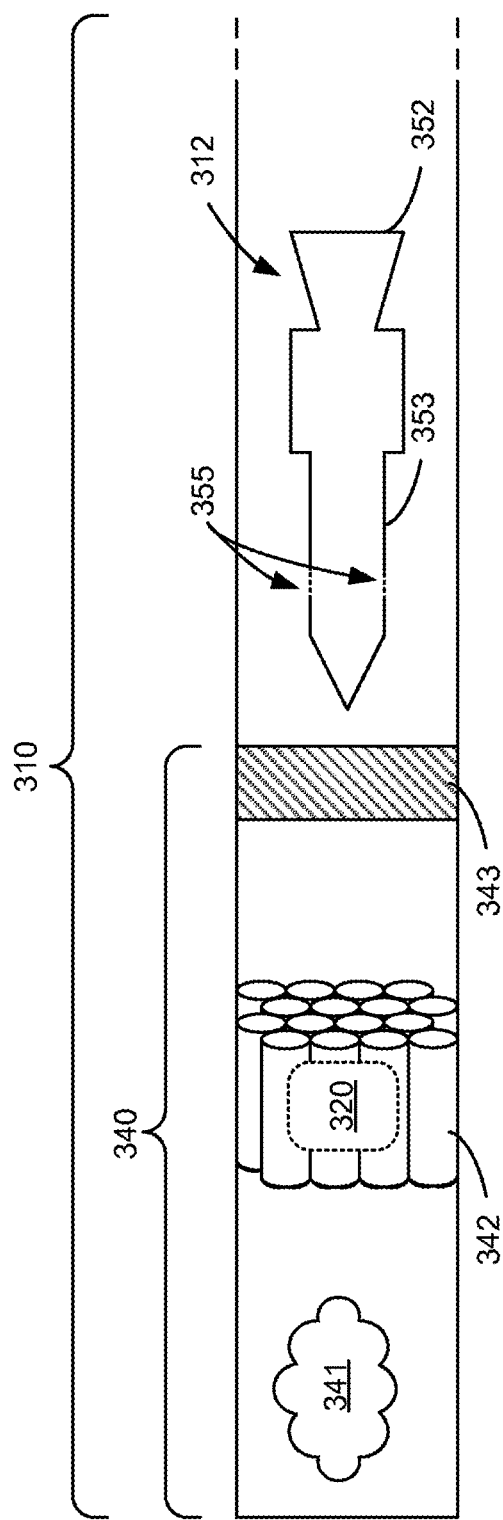
FIG. 3A is an illustration of a medicament cartridge and reservoir tap for an inhaled medicament delivery device.
Figure 3B:
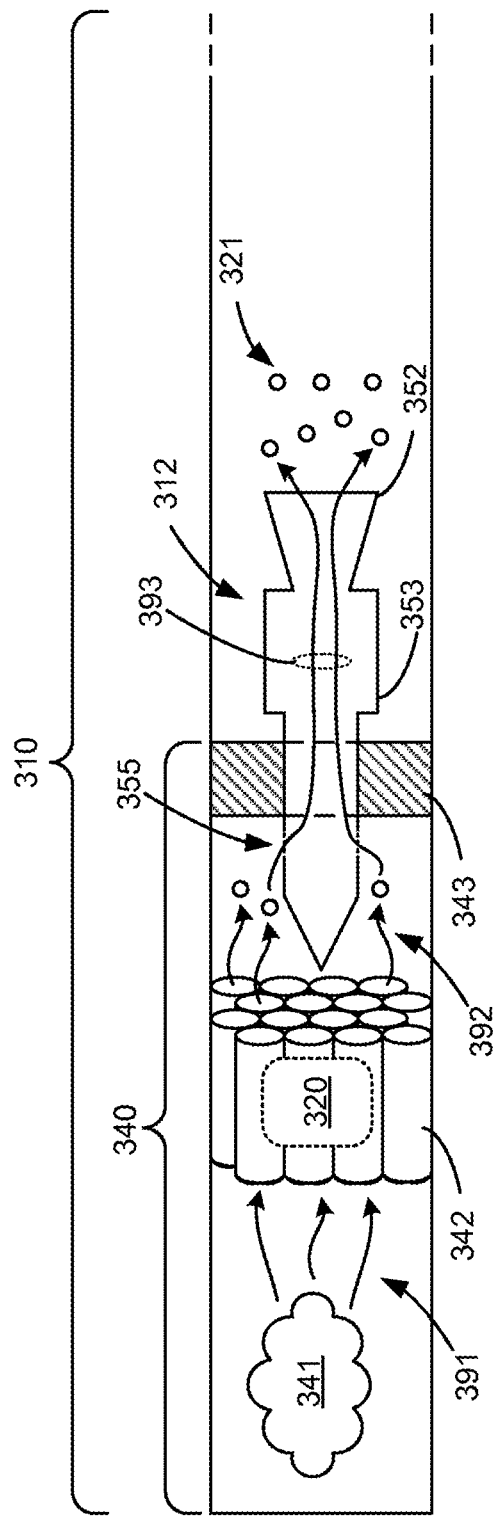
FIG. 3B is an illustration of the functioning of a reservoir tap of an inhaled medicament delivery device.

FIG. 3B is an illustration of the functioning of a reservoir tap 312 of an inhaled medicament delivery device 310. In FIG. 3B, the reservoir tap 312 is positioned such that a tap shaft 353 penetrates a seal 343 to an extent that leaves ports 355 exposed to the interior of a medicament cartridge 340. The ports 355 are exposed to the interior of the medicament cartridge 340 so that a medicament 320 may enter a hollow interior cavity of the tap shaft 353 and flow from the medicament cartridge 340 to a nozzle 352 under the force of a propellant gas 341.

As illustrated in FIG. 3B, when the reservoir tap 312 is in an activated position, the propellant gas 341 enters a porous reservoir material 342 to displace a medicament 320 (shown in FIG. 3B by arrows 391).

As shown by arrows 392, as the medicament 320 is displaced from the porous reservoir material 342, the medicament 320 travels to the ports 355. As shown by arrows 393, the medicament 320 enters the ports 355 and travels down the tap shaft 353 to exit the nozzle 352 as an aerosol mixture 321.

The pressure within the reservoir tap 312 may be lower than the pressure within the medicament cartridge 340. When the reservoir tap 312 penetrates and passes through the seal 343, the pressure inside the medicament cartridge 340 drops to equilibrate with the lower pressure within the reservoir tap 312. In an embodiment, the pressurized gas provides the propellant force to drive the liquid medicament 320 out of the medicament cartridge 340 and into the nozzle 352.

The speed and force with which the propellant gas 341 expands may be determined by factors such as, for example, the pressure differential between the reservoir tap 312 and the medicament cartridge 340 as well as the speed at which the pressure inside the medicament cartridge 340 is dropped. When the reservoir tap 312 penetrates the seal 343, the propellant gas 341 expands out of the medicament cartridge 340 and displaces the liquid medicament 320 in the cartridge 340. When the propellant gas 341 powerfully expands out of the medicament cartridge 340, the propellant gas 341 may eject the medicament 320 liquid out of the medicament cartridge 340 and into the tap shaft 353 through the reservoir tap 312.

The ejected medicament 320 liquid may disperse into smaller droplets of liquid within the reservoir tap 312, thus forming an aerosol. The formed aerosol may be propelled by the force of the propellant gas 341 through the length of the reservoir tap 312, through the tap shaft 353, through the mouth of a subject, through the oropharynx of a subject, and into the lungs of a subject.

In another embodiment, features are added that act as air flow amplifiers that increase the velocity of the medicament 320 and/or volume of air as it travels through the mechanisms and devices described herein. For example, in an embodiment, the Venturi effect is utilized to increase the velocity of the medicament 320 liquid within the inhaled medicament delivery device 310. The Venturi effect describes an increase in the velocity of a fluid traveling through a constriction in a conduit. A constriction in at least a segment of the reservoir tap 312, or the nozzle 352, may create an area of increased fluid velocity through that constricted segment. For example, the ports 355 may comprise narrow channels for the passage of liquid medicament 320 into the reservoir tap 312. The travel of the medicament 320 liquid from the medicament cartridge 340 is accelerated as it passes through narrow channels of the ports 355 into the reservoir tap 312. The greater the velocity of the fluid as it travels into and through the reservoir tap 312, typically the greater the degree of aerosol formation. Also, when the medicament 320 liquid travels with greater velocity through the reservoir tap 312, the inhaled medicament delivery device 310 may deliver a larger volume in a shorter time. For example, in an embodiment, the reservoir tap 312 or the nozzle 352 may comprise a structure that generates a Coanda effect further increasing the velocity of the fluid traveling through the reservoir tap 312 from the medicament cartridge 340.

In another embodiment, the phase change of a liquid excipient to a gas, such as, for example, glycerol, may occur causing an increase in propulsion and thus an increase in the velocity of the medicament 320 liquid traveling through the reservoir tap 312 and the tap shaft 353.

Generally, the embodiments comprising the Venturi effect, the Coanda effect, or a phase change in a liquid excipient to a gas can promote airflow magnification within the inhaled medicament delivery device 310. A benefit of airflow magnification within the inhaled medicament delivery device 310 is that it may provide increased per use volume of the delivered inhalable medicament 320 independent of the size and volume of the medicament cartridge 340. The Coanda effect may be utilized to orient a circumferential (in relation to the jet ports in the nozzle) air envelope. The cylindrical air envelope can serve to focus the aerosol generated by the jet ports (or ultrasonic nozzle) to reduce or mitigate impact of the aerosol onto the interior surface of the aspiration tube and thus reduce the amount of drug loss in the inhaled medicament delivery device 310 or serving to reduce or mitigate the aerosol being exposed to a higher temperature on the surface of the tap shaft 353.

In an embodiment, a nozzle 352 comprises an ultrasonic nozzle 352. The ultrasonic nozzle 352 is connected to a power source and at least one piezoelectric transducer that creates ultrasonic sound waves within the ultrasonic nozzle 352. When a fluid is in contact with an ultrasonic sound wave within an ultrasonic nozzle 352, a capillary wave is formed within the fluid. When the amplitude of the capillary wave reaches a certain height, the fluid separates into droplets creating an aerosol within the ultrasonic nozzle 352.

The pressurized fluid within the medicament cartridge 340 may comprise a medicament 320 that is delivered in an inhalable form to a subject using the inhaled medicament delivery device 310.

The aerosol mixture 321 may be further thermally modulated and/or mixed with additional air by the inhaled medicament delivery device 310. The aerosol mixture 321 may correspond to, or be a precursor to, the mixture 121 and/or the mixture 221, described herein.

Figure 3C:
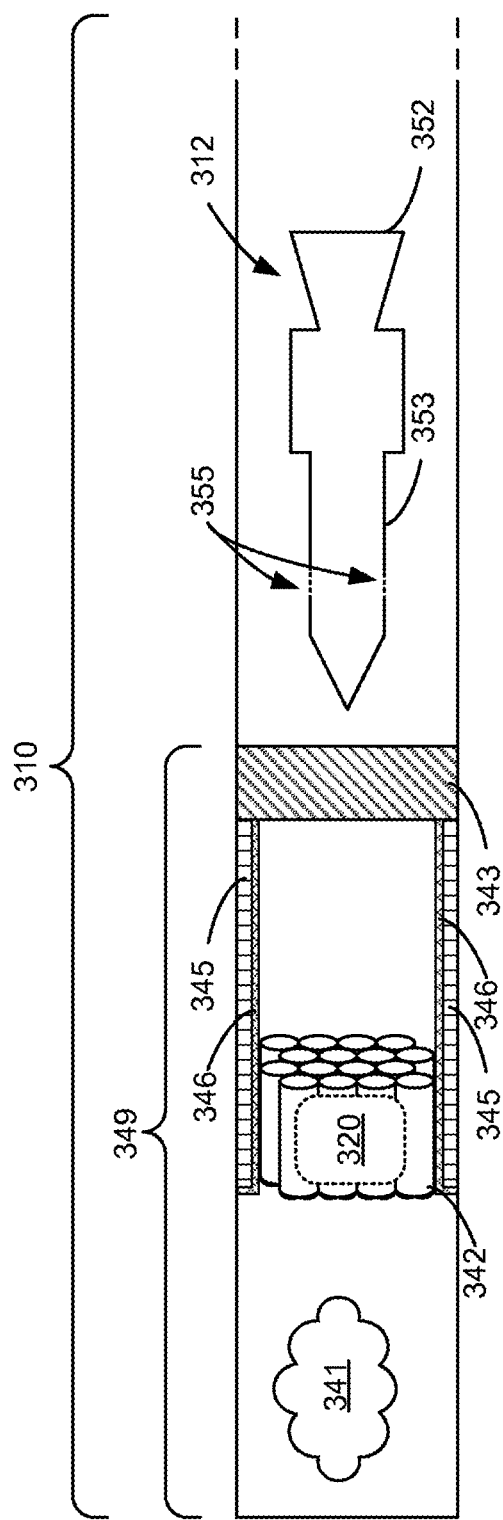
FIG. 3C is an illustration of a tamper-resistant medicament cartridge and a reservoir tap for inhaled medicament delivery device.

FIG. 3C is an illustration of a tamper-resistant medicament cartridge and a reservoir tap 312 for an inhaled medicament delivery device 310. In FIG. 3C, the inhaled medicament delivery device 310 comprises the tamper-resistant cartridge 349, and the reservoir tap 312. The tamper-resistant cartridge 349 includes a porous reservoir material 342, a medicament 320, a cartridge seal 343, a neutralizing agent 345, and an encapsulation 346. The reservoir tap 312 includes a tap shaft 353 and a nozzle 352. The encapsulation 346 separates a neutralizing agent 345 from the medicament 320. The encapsulation 346 encases the neutralizing agent 345 such that, if the encapsulation 346 is penetrated, the neutralizing agent 345 will be allowed to react with the medicament 320, thereby rendering the liquid formulation of the medicament 320 inaccessible or functionally neutralized. The tamper-resistant cartridge 349 may be separable from and re-attachable to the inhaled medicament delivery device 310 without penetrating the encapsulation 346 or otherwise releasing the neutralizing agent 345 to react with the medicament 320. The reservoir tap 312 is configured to penetrate the tamper-resistant cartridge 349 without penetrating the encapsulation 346 or otherwise releasing the neutralizing agent 345 to react with the medicament 320.

Figure 3D:
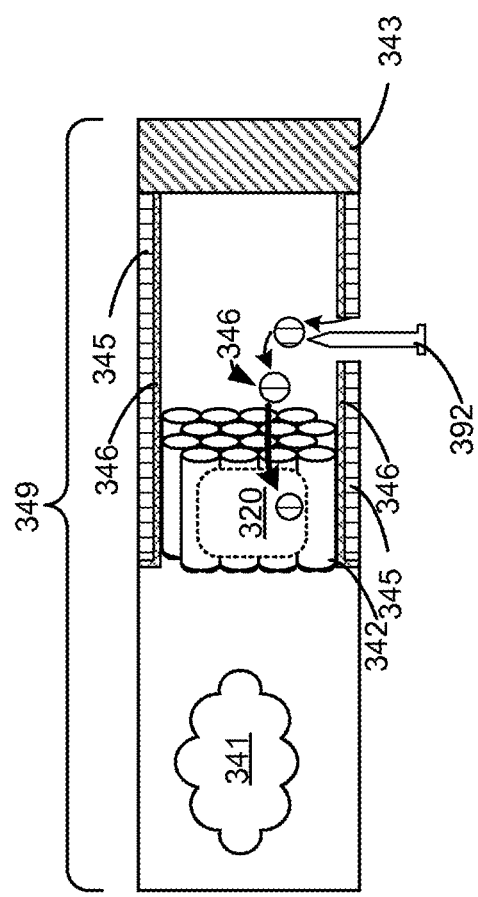
FIG. 3D is an illustration of the neutralization of medicament by a tamper-resistant cartridge.

FIG. 3D is an illustration of the neutralization of a medicament 320 by a tamper-resistant cartridge 349. In FIG. 3D, a penetrating object 392 enters the interior of the tamper-resistant cartridge 349. In order to enter the interior of the tamper-resistant cartridge 349, the penetrating object 392 ruptures or otherwise destroys the integrity of the encapsulation 346. With the integrity of the encapsulation 346 compromised, the neutralizing agent 345 can contact and thereby react with the medicament 320, thereby rendering the liquid formulation of the medicament 320 inaccessible or functionally neutralized. The porous reservoir material 342 may contain encapsulated absorbents or neutralizing agents (not illustrated) such as to prevent intentional or unintentional access or contact with the liquid formulation of the medicament 320. The encapsulated absorbent, such as charcoal, would be encased in a hydrophobic casing such as a plastic, polymer, ceramic, or glass such that if the medicament cartridge 340 was accessed and the porous reservoir material 342 was removed (or penetrated in a manner not corresponding to the activation of the reservoir tap 312), the encapsulation 346 would rupture or otherwise allow the absorbent or neutralizing agent 345 to come into contact with the liquid formulation of the medicament 320 and render the medicament 320 inaccessible or functionally neutralized.

Figure 4A:
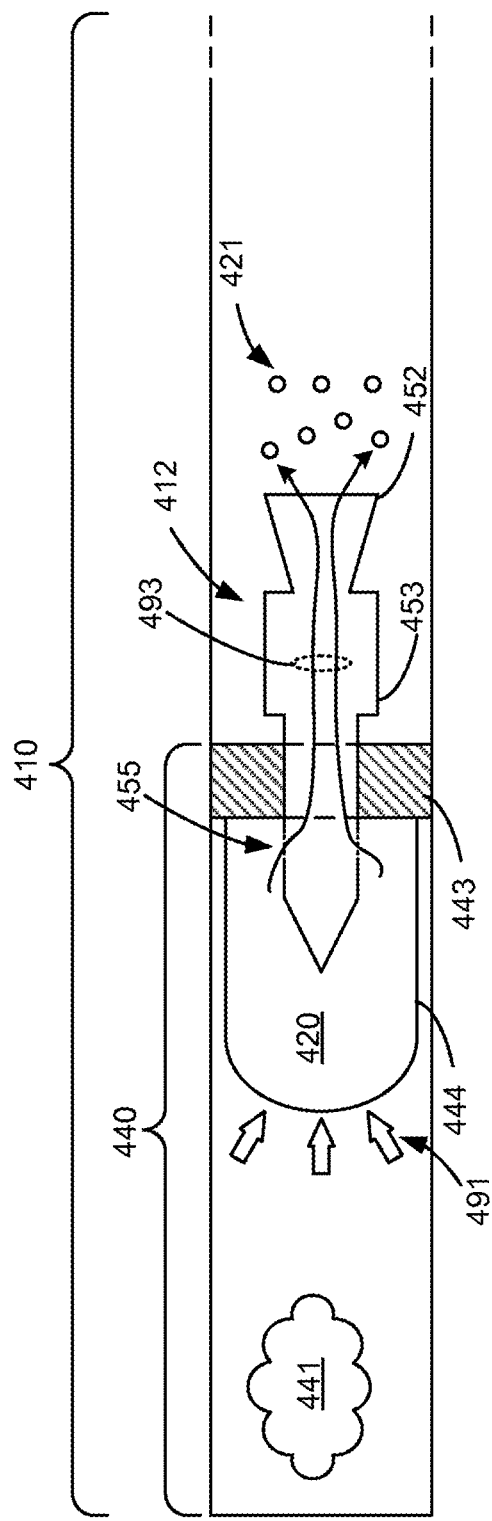
FIG. 4A is an illustration the operation of a medicament cartridge with medicament bladder.

FIG. 4A is an illustration the operation of a medicament cartridge with medicament bladder embodiment. In FIG. 4A, an inhaled medicament delivery device 410 comprises a cartridge 440, and a reservoir tap 412. The cartridge 440 includes a bladder 444, a medicament 420, and a cartridge seal 443. The reservoir tap 412 includes a tap shaft 453, and a nozzle 452. The tap shaft 453 is hollow and includes ports 455 that allow liquids or gasses to flow from outside the reservoir tap 412, into the tap shaft 453, and out the nozzle 452. The bladder 444 holds the medicament 420. The cartridge 440 may be separable and re-attachable from the inhaled medicament delivery device 410. The compressible bladder 444 is preferably positioned proximally to the pressurized gaseous propellant relative to the reservoir tap 412. When the pressure changes within the cartridge 440, the gaseous propellant expands, compressing the liquid containing compressible bladder 444. The forceful compression of the bladder 444 causes an ejection of the medicament 420 liquid within it. It should be understood that the compressible bladder 444 can have alternate variations such as, for example, a compressible bag or balloon. In an embodiment, the bladder 444 may be distensible and exert a pressure on the liquid wholly or partially (in conjunction with the pressurized gas) drive the liquid into the nozzle. Also, the bladder 444 may be comprised of a plurality of layers, such that between the inner bladder 444, which contains the liquid medicament 420, and the outer bladder 444 there is a space that could contain dry neutralizing agent or absorbent material to render the active excipient inactive or to otherwise absorb and capture the active excipient. A liquid neutralizing agent could also be contained in the space between the outer surface of the inner bladder 444 and the inner surface of the outer bladder 444.

The bladder 444 allows for the inhaled medicament delivery device 410 to be activated in a fashion that is independent of the orientation in space of the inhaled medicament delivery device 410. In an embodiment, the bladder 444 is positioned in the cartridge directly adjacent to the cartridge seal 443. In an embodiment, the bladder 444 shares a common wall with the cartridge seal 443. In an embodiment, this position places the bladder 444 along with the liquid medicament 420 inside of it in a position that is more proximal to a subject than a propellant gas. Said another way, in this embodiment, no matter what the orientation of the device, the medicament 420 within the bladder 444 is always positioned between most of the propellant 441 in the cartridge 440 and the cartridge seal 443. In this way, when the cartridge seal 443 is penetrated, the propellant 441 be will behind the liquid medicament 420 and eject the medicament 420 into the reservoir tap 412 independently of the orientation in which the inhalable medicament delivery device 410 is held.

In FIG. 4A, the reservoir tap 412 is illustrated, positioned such that tap shaft 412 penetrates the cartridge seal 443 to an extent that leaves the ports 455 exposed to the interior of the bladder 444. The ports 455 are exposed to the interior of the bladder 444 so that the medicament 420 may enter a hollow interior cavity of the tap shaft 453 and flow from the cartridge 440 to the nozzle 452 under the force that the propellant 441 exerts on the bladder 444.

As also illustrated in FIG. 4A, when the reservoir tap 412 is in an activated position, the propellant 441 exerts a force (illustrated by arrows 491) on the bladder 444 to push the medicament 420 out of the reservoir 342 via the ports 455. The medicament 420 enters the ports 455 and travels down the tap shaft 453 to exit the nozzle 452 as the aerosol mixture 421. The aerosol mixture 421 may be further thermally modulated and/or mixed with additional air by the inhaled medicament delivery device 410. The aerosol mixture 421 may correspond to, or be a precursor to, the mixture 121 and/or the mixture 221, described herein.

In an embodiment, the liquid medicament 420 may be in a distensible bladder 444. In an embodiment, the liquid medicament 420 with the bladder 444 distends the bladder 444 like an overfilled balloon to generate an intrinsic pressure within the walls of the bladder 444. The pressure caused by the distended bladder 444 may provide a force (retains the liquid under a pressure) that may propel the liquid out of the liquid reservoir and into the nozzle 452 when the cartridge seal 443 and cartridge 440 are penetrated. This pressure may be a result of an elastic force (e.g., like a stretched rubber band) provided by the distended bladder 444.

Figure 4B:
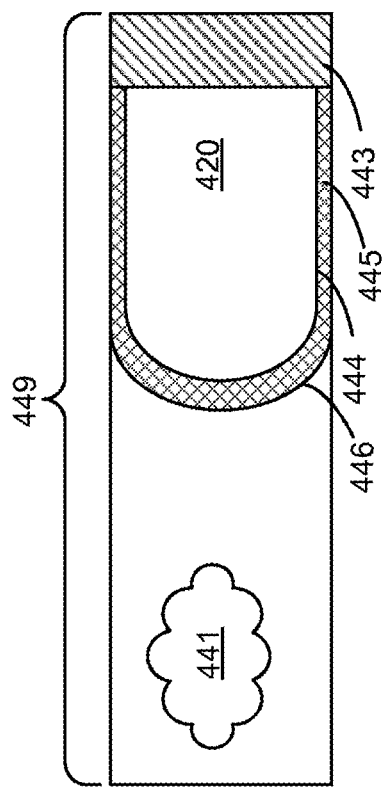
FIG. 4B is an illustration the operation of a tamper-resistant medicament cartridge.

FIG. 4B is an illustration the operation of a tamper-resistant medicament cartridge. In FIG. 4B, the inhaled medicament tamper-resistant cartridge 449 includes a bladder 444, a medicament 420, a cartridge seal 443, a neutralizing agent 445, and a bladder 446. The bladder 444 holds the medicament 420. The bladder 446 holds the neutralizing agent 445. The bladder 446 holds neutralizing agent 445 in a space between an outer wall of the bladder 444 and an inner wall of the bladder 446. Thus, in order to penetrate the bladder 444 from outside of the inhaled medicament tamper-resistant cartridge 449 (except through the seal 443), the penetrating object would need to first penetrate the bladder 446.

The bladder 444 separates the neutralizing agent 445 held by the bladder 446 from the medicament 420. The bladder 346 holds the neutralizing agent 445 around the outer wall of the bladder 444, such that if the bladder 444 is penetrated, the neutralizing agent 445 will be allowed to react with the medicament 420, thereby rendering the liquid formulation of the medicament 420 inaccessible or functionally neutralized. The inhaled medicament tamper-resistant cartridge 449 may be separable and re-attachable from an inhaled medicament delivery device 410 without penetrating the bladders 446, 444, or otherwise releasing the neutralizing agent 445 to react with the medicament 420.

In an embodiment, a cartridge comprises a pressure plate positioned between the medicament and the distal most portion of the cartridge. In an embodiment, a pressure plate is a plate or sliding seal (e.g., like the plunger seal of a syringe) having the same dimensions as the interior of the cartridge. In an embodiment, a pressure plate has a proximal side or surface facing the proximal portion or section of a cartridge, and a distal side or surface facing the distal portion or section of a cartridge. In an embodiment, the pressure plate effectively forms a seal with the cartridge walls so that a medicament within the cartridge is positioned entirely on a proximal side of the pressure plate. In an embodiment, the pressure plate is slideably moveable along the interior of the cartridge. For example, the pressure plate may be configured to move along a track within the cartridge interior. In an embodiment, a change in pressure within the cartridge causes a pressure plate to move forward towards the proximal end of a cartridge. When a pressure plate moves forward within the cartridge towards the proximal portion of the cartridge, the medicament on the proximal side of the pressure plate is pushed or ejected out of the cartridge by the pressure plate. In an embodiment, the portion of the cartridge that is on the proximal side of the pressure plate is pressurized so that a pressure plate is pushed towards the distal section of the cartridge. When the pressure on the proximal side of the pressure plate drops, the pressure plate will be caused to move forward within the cartridge, ejecting a medicament positioned on a proximal side of the pressure plate. In an embodiment, a compressed gaseous propellant is positioned on the distal side of a pressure plate. When a pressure is dropped within a cartridge the gaseous propellant positioned on the distal side of the pressure plate expands, moving the pressure plate forward towards the proximal end of the cartridge, and pushing or ejecting the medicament positioned on the proximal side of the pressure plate out of the cartridge. In an embodiment, the movement of the pressure plate within the cartridge is electronically conveyed such that the volume of the medicament or number of remaining doses is correspondingly determined based on the relative position of the pressure plate. In an embodiment, the relative position of the pressure plate is communicated electronically with the device, such that of there is movement of the pressure plate that does not correspond to an intentional activation as would be the case of tampering, damage, or malfunction, which could render the device inactive.

In an embodiment, the pressure plate may be moved by mechanical (e.g., lead screw) or electrical means to provide doses. In this manner, the distance traveled by the pressure plate may be monitored to determine the remaining volume of the medicament or number of remaining doses. Likewise, the distance traveled by the pressure plate may be monitored to determine the volume of each dose and/or the volume and/or number of doses already expended. The number of turns a lead screw is advanced can provide a highly accurate way to measure and/or provide doses of the medicament.

Figure 5A:
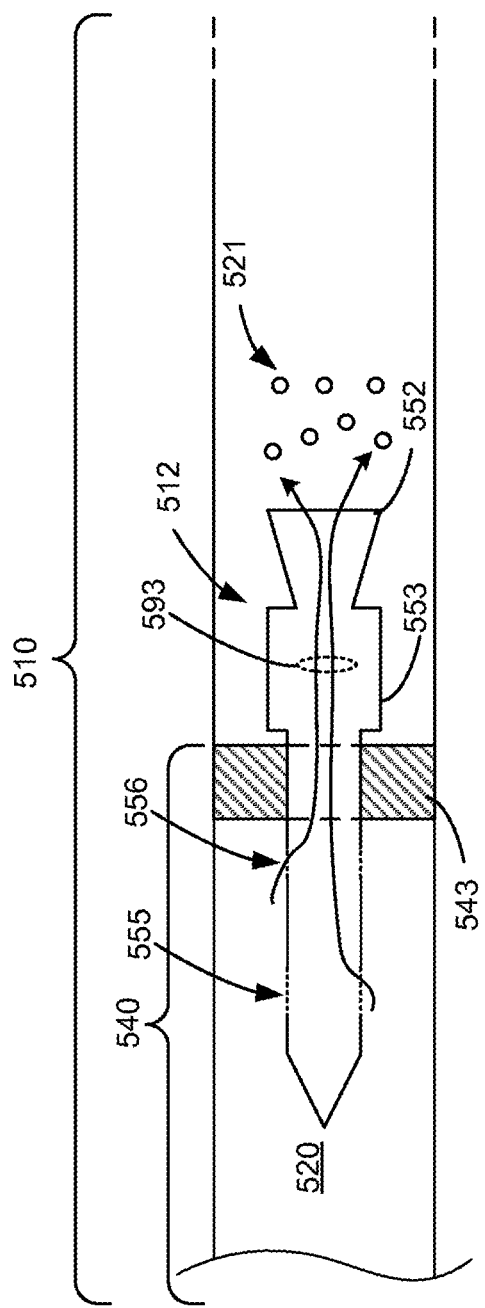
FIG. 5A is an illustration of a reservoir and reservoir tap positioned to provide a first medicament dosing/mixture.

FIG. 5A is an illustration of a reservoir and reservoir tap positioned to provide a first medicament dosing/mixture. In FIG. 5A, an inhaled medicament delivery device 510 comprises a cartridge 540 and a reservoir tap 512. The cartridge 540 includes a medicament 520, and a cartridge seal 543. The reservoir tap 512 includes a tap shaft 553 and a nozzle 552. The tap shaft 553 is hollow and includes first ports 555 and second ports 556 that allow liquids or gasses to flow from outside the reservoir tap 512, into the tap shaft 553, and out the nozzle 552. The cartridge 540 may be separable and re-attachable from the inhaled medicament delivery device 510.

In FIG. 5A, the reservoir tap 512 is illustrated positioned such that the tap shaft 512 penetrates the seal 543 to an extent that leaves both the first ports 555 and the second ports 556 exposed to receive the medicament 520. As shown by arrows 593, the first ports 555 and the second ports 556 are both exposed to such that the medicament 520 may enter a hollow interior cavity of the tap shaft 553 and flow from the cartridge 540 to the nozzle 553 under the force of a propellant. Since the first ports 555 and the second ports 556 both allow the medicament 520 to enter the hollow interior cavity of the tap shaft 553, a greater flow of the medicament 520 is expected than if just one of the first or second ports 555, 556 were to allow the medicament 520 to enter the hollow interior cavity of the tap shaft 553.

As illustrated in FIG. 5A, when the reservoir tap 512 is in a first activated position, the medicament 520 enters the first ports 555 and the second ports 556 and travels down the tap shaft 553 to exit the nozzle 552 as an aerosol mixture 521. The aerosol mixture 521 may be further thermally modulated and/or mixed with additional air by the inhaled medicament delivery device 510. The aerosol mixture 521 may correspond to, or be a precursor to, the mixture 121 and/or the mixture 221, described herein.

Figure 5B:
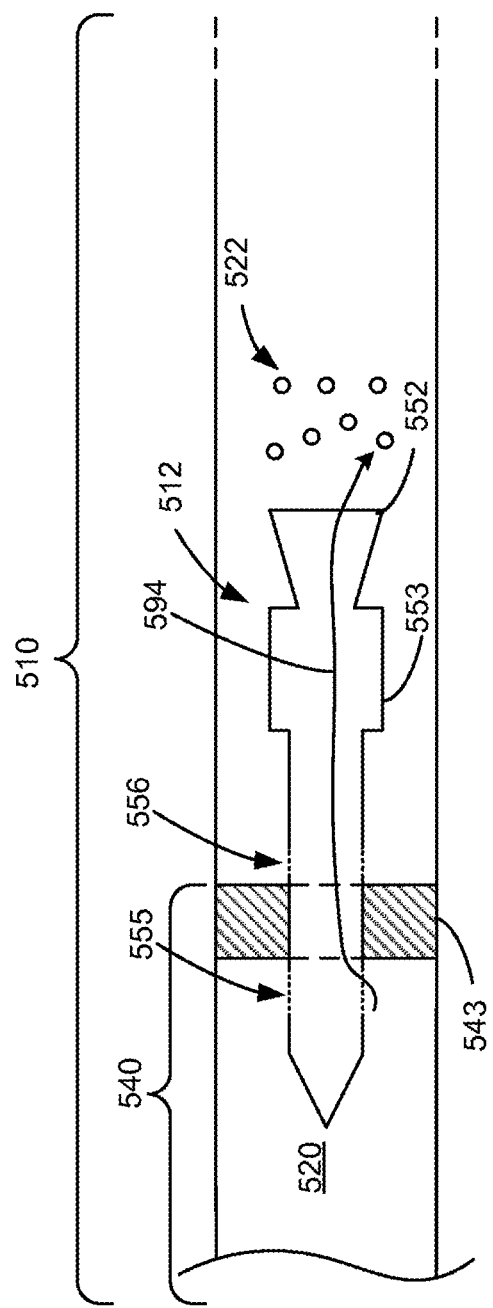
FIG. 5B is an illustration of a reservoir and reservoir tap positioned to provide a second medicament dosing/mixture.

As illustrated in FIG. 5B, when the reservoir tap 512 is in a second activated position, the medicament 520 enters only the first ports 555 and not the second ports 556. The second ports 556 are not exposed to the medicament 520. The second ports 556 may be prevented from being exposed to the medicament 520 because the second ports 556 are occluded by the seal 543. The second ports 556 may be prevented from being exposed to the medicament 520 because, when the reservoir tap 512 is in the second activated position, the ports 556 are still outside of the cartridge 540 or otherwise positioned in order to prevent the flow of the medicament 520 via the second ports 556.

As shown by arrow 594, the medicament 520 enters only the first ports 555 and travels down the tap shaft 553 to exit the nozzle 552 as an aerosol mixture 522. The aerosol mixture 522 may be further thermally modulated and/or mixed with additional air by the inhaled medicament delivery device 510. The aerosol mixture 522 may correspond to, or be a precursor to, the mixture 121 and/or the mixture 221, described herein.

Figure 5C:
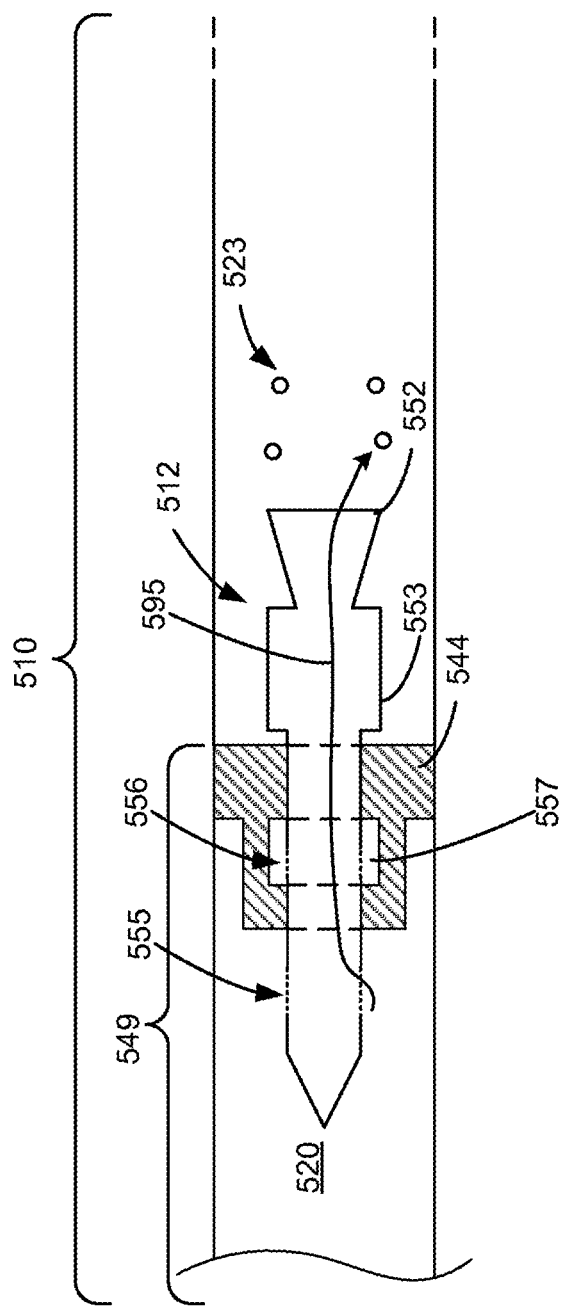
FIG. 5C is an illustration of a cartridge configured to control a medicament dosing/mixture.

FIG. 5C is an illustration of a cartridge configured to control a medicament dosing/mixture. In FIG. 5C, an inhaled medicament delivery device 510 comprises a cartridge 549 and a reservoir tap 512. The cartridge 549 includes a medicament 520 and a cartridge seal 544. The reservoir tap 512 includes a tap shaft 553 and a nozzle 552. The tap shaft 553 is hollow and includes first ports 555 and second ports 556 that, depending on the position of the reservoir tap 512 and the configuration of the cartridge seal 544, can allow liquids or gasses to flow from outside the reservoir tap 512, into the tap shaft 553, and out the nozzle 552. The cartridge 540 may be separable and re-attachable from the inhaled medicament delivery device 510.

In FIG. 5C, the reservoir tap 512 is positioned in the same position as in FIG. 5A. In FIG. 5C, the tap shaft 553 penetrates the cartridge seal 544 to an extent that it leaves the first ports 555 exposed to receive the medicament 520, but due to the configuration of the cartridge seal 544 does not expose the second ports 556 to receive the medicament 520. As shown by arrows 595, the first ports 555 (but not the second ports 556) are exposed to such that the medicament 520 may enter a hollow interior cavity of the tap shaft 553 and flow from the cartridge 540 to the nozzle 553 under the force of a propellant. Since the configuration of the cartridge seal 544 only exposes the first ports 555 to the medicament 520 such that the medicament 520 can enter the hollow interior cavity of the tap shaft 553, a lesser flow of the medicament 520 is expected than if both of the first and second ports 555, 556 were to allow the medicament 520 to enter the hollow interior cavity of the tap shaft 553 (as is illustrated in FIG. 5A for the same position of the reservoir tap 512).

As illustrated in FIG. 5C, even though the reservoir tap 512 is in the first activated position, the configuration of a seal 544 of the cartridge 549 only allows the medicament 520 to enter the ports 555 travel down the tap shaft 553 to exit the nozzle 552 as the aerosol mixture 523. The aerosol mixture 523 may be further thermally modulated and/or mixed with additional air by the inhaled medicament delivery device 510. The aerosol mixture 523 may correspond to, or be a precursor to, the mixture 121 and/or the mixture 221, described herein. Thus, it should be understood that an aerosol mixture output by the nozzle 552 can be controlled or affected by the position of the reservoir tap 512, the configuration of the cartridge 540, and both the position of the reservoir tap 512 and the configuration of the cartridge 540 (and the configuration of the seals 543 and/or the 544, in particular).

In an embodiment, a seal 544 is configured with a cavity 557. The cavity 557 exists such that the second ports 556 are exposed to the cavity 557 when the reservoir tap 512 is in the first activated position. The cavity 557 may be pressurized with propellant, or exposed to outside air in order to help determine the composition of the mixture 523. The cavity 557 may be pressurized with a gas to provide a positive flow of gas before the medicament 520 begins to flow through the reservoir tap 512. This positive flow of gas before the flow of the medicament 520 begins may occur as the ports 555 pass (or stop) through the cavity 557 on the way to being exposed to the medicament 520.

In an embodiment, the reservoir tap 512 comprises one or more the first ports 555 and the second ports 556 that open into the lumen of the reservoir tap 512. In one variation, the first ports 555 and the second ports 556 are in line with each other and are positioned along the length of the reservoir tap 512. The first ports 555 and the second ports 556 may, for example, be identical in size or may, for example, have differing sizes. The first port 555 may, for example, be smaller than the second port 556.

The dose of the medicament 520 delivered into the reservoir tap 512 may be controlled by, for example, controlling the penetration of the nozzle 552 to different depths within the cartridge 540. For example, when the reservoir tap 512 penetrates and passes through the cartridge seal 543 to a certain depth, only the first port 555 is exposed within the interior of the cartridge, while the second port 556 may remain embedded within the interior of the seal 543 so that the seal 543 covers the second port 556, sealing it off. A deeper penetration exposing both the first port 555 and the second port 556 within the cartridge 540 would enable fluid to be ejected through the cartridge 540 at a faster rate. It should be understood, that the number of ports need not be limited to two, but may also comprise, for example, three, four, five, or more ports along the reservoir tap 512. Similarly, it should be understood that the location and position of the ports relative to each other may be varied. For example, multiple ports may be located circumferentially along the reservoir tap 512. For example, the ports need not be in line with each other but can be spaced apart at variable distances from each other. Similarly, various shapes are usable for the ports including, for example, circular, ellipsoidal, and polygonal shapes. Similarly, there are other means known to those having skill in the art for selectively sealing off the ports aside from covering one or more of the ports within the cartridge seal 543. For example, the reservoir tap 512 may move slideably within a housing capable of selectively blocking off ports depending on the distance traveled by the slideable reservoir tap within the housing. In another example a variable rate flow controller valve could be used to selectively control the flow of liquid or gases or medicament 520 from the cartridge 540.

The reservoir tap 512 may be advanced into and through the cartridge seal 544 with, for example, a spring driven mechanism. The reservoir tap 512 may be advanced into and through the seal 543 with, for example, a manually driven mechanism. Any known mechanism that advances the reservoir tap 512 into and though the cartridge seal 543 is suitable.

Figure 6A:
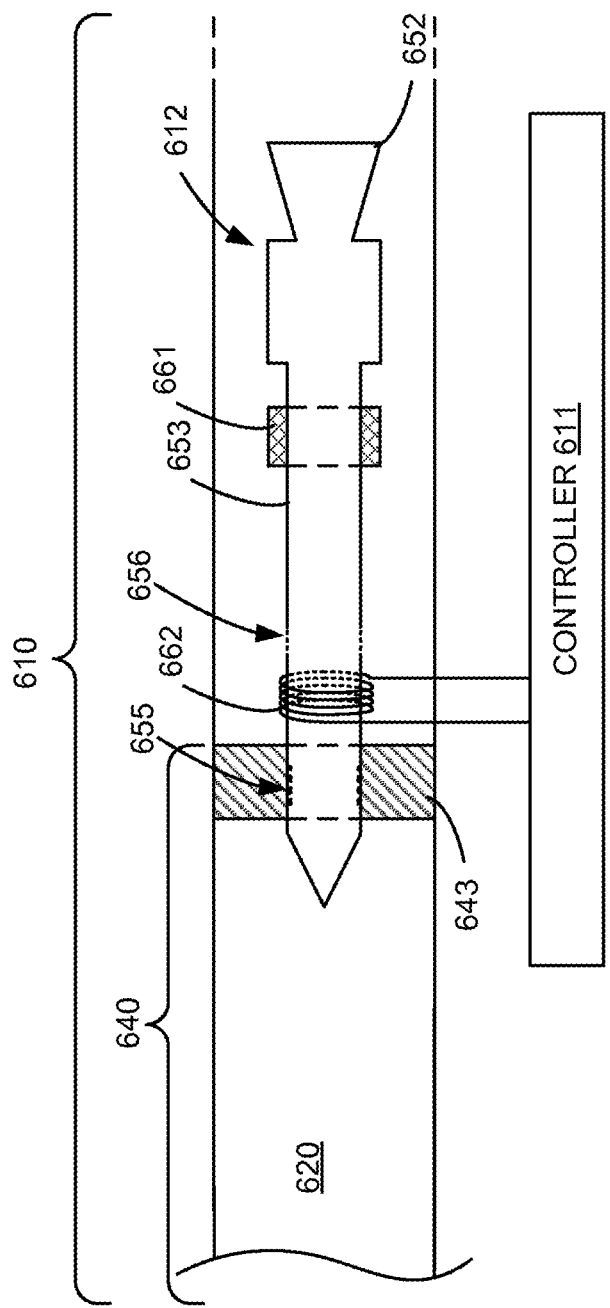
FIGS. 6A-6C illustrate the actuation of a reservoir tap.
Figure 6B:
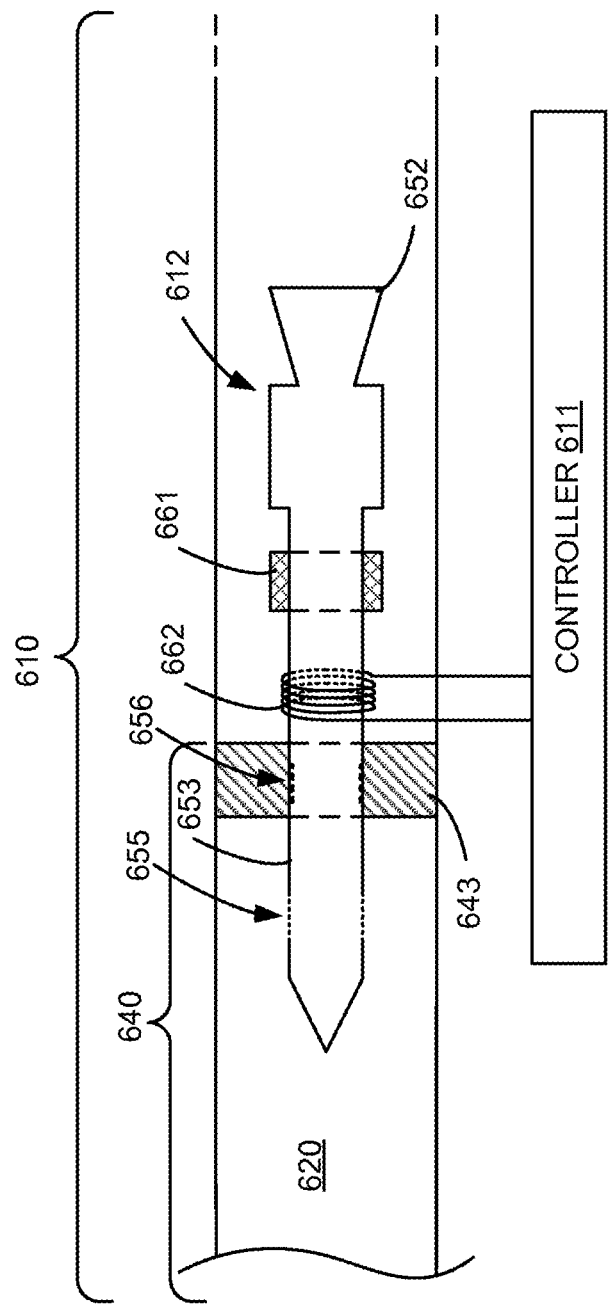
Figure 6C:
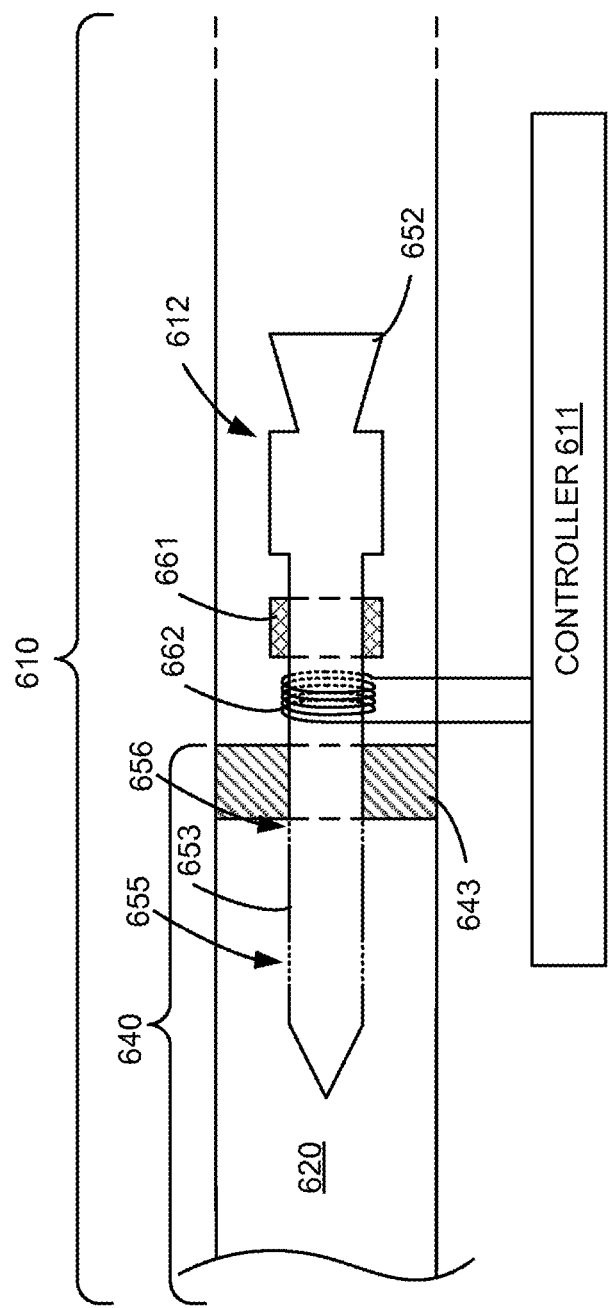

FIGS. 6A-6C show an embodiment in which a reservoir tap 612 is driven by a magnetic actuator under the control of a controller 611. In FIGS. 6A-6C, the inhaled medicament delivery device 610 comprises a cartridge 640, a controller 611, an actuator 662, a magnet 661, and a reservoir tap 612. The cartridge 640 includes a medicament 620, and a cartridge seal 643. The reservoir tap 612 includes a tap shaft 653 and a nozzle 652. The tap shaft 653 is hollow and includes ports 655 and ports 656 that allow liquids or gasses to flow from outside the reservoir tap 612, into the tap shaft 653, and out the nozzle 652. The cartridge 640 may be separable and re-attachable from the inhaled medicament delivery device 610.

The actuator 662 is operatively coupled to the controller 611. The actuator 662 is under the control of the controller 611, which selectively attracts or repels the magnet 661. The magnets 661 are attached to the reservoir tap 612 such that, as the actuator 662 attracts or repels the magnet 661 to apply a force to the magnets 661, the reservoir tap 612 moves with the magnets 661. The actuator 662 is attached to the inhaled medicament delivery device 610, but not the reservoir tap 612, such that the reservoir tap 612 may slideably move proximally and distally with respect to the cartridge 640. The reservoir tap 612 may, under the control of the controller 611, slideably move proximally and distally with respect to the cartridge 640 in order to position the reservoir tap 612 such that the ports 655 and/or 656 may be controllably positioned to receive the medicament 620.

FIG. 6A illustrates the actuating of the reservoir tap 612 by the controller 611 (via the interaction of the actuator 662 and the magnets 661) to a first (inactive) position. In the first position illustrated in FIG. 6A, the ports 655 are occluded by the seal 643. The ports 656 are positioned more proximally along the tap shaft 653 than the ports 655. Thus, the ports 656 are positioned such that they are not capable of receiving the medicament 620.

FIG. 6B illustrates the actuating of the reservoir tap 612 by the controller 611 (via the interaction of the actuator 662 and the magnets 661) to a second (active) position. In the second position illustrated in FIG. 6B, the reservoir tap 612 has been displaced by the controller 611 to a position more distal than illustrated in FIG. 6A. The ports 655 are exposed to receive the medicament 620. The ports 656 are occluded by the cartridge seal 643. Thus, the ports 656 are positioned such that they are not capable of receiving the medicament 620.

FIG. 6C illustrates the actuating of the reservoir tap 612 by the controller 611 (via the interaction of the actuator 662 and the magnets 661) to a third (active) position. In the third position illustrated in FIG. 6C, the reservoir tap 612 has been displaced by the controller 611 to a position more distal than illustrated in FIG. 6B. The ports 655 and 656 are exposed to receive the medicament 620. Accordingly, it should be understood that the controller 611 may dynamically move the reservoir tap 612 in order to allow medicament 620 to flow or not flow through the reservoir tap 612 (and thereby generate an aerosol). The controller 611 may dynamically move the reservoir tap 612 in order to modulate the flow of the medicament 620 through the reservoir tap 612 (and thereby control the mixture of a generated aerosol).

Figure 7:
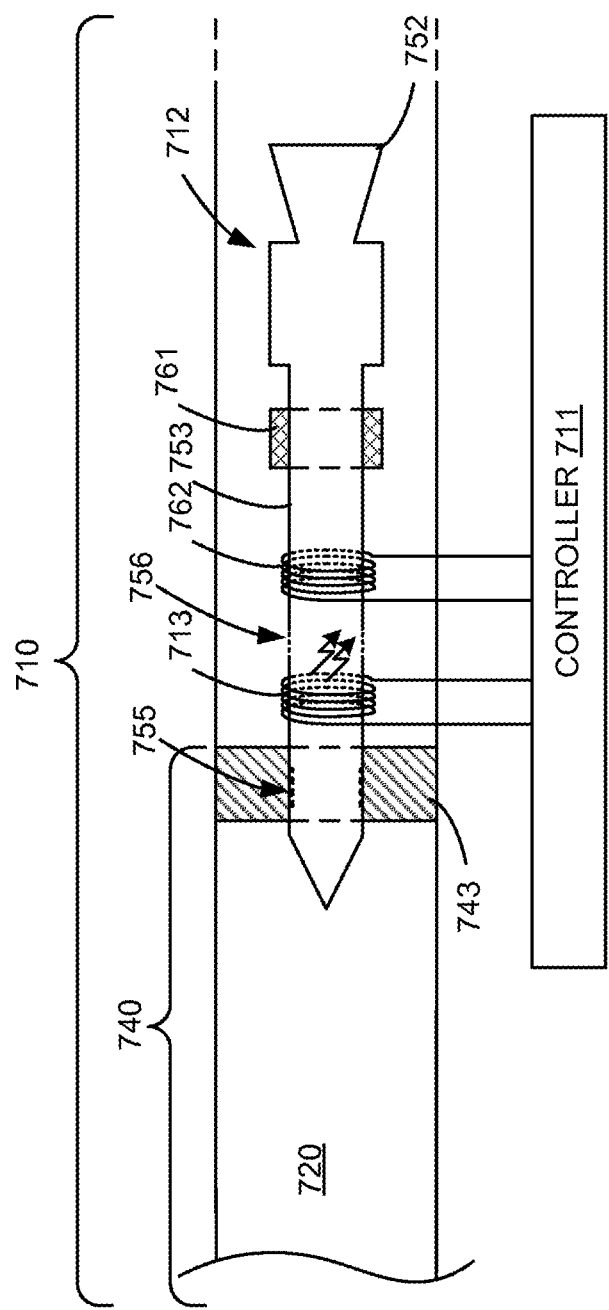
FIG. 7 illustrates controlled thermal heating of a reservoir tap.

FIG. 7 illustrates controlled thermal heating of a reservoir tap. In FIG. 7, an inhaled medicament delivery device 710 comprises a cartridge 740, a controller 711, an actuator 762, a magnet 761, a heater 713, and a reservoir tap 712. The cartridge 740 includes a medicament 720, and a cartridge seal 743. The reservoir tap 712 includes a tap shaft 753 and a nozzle 752. The tap shaft 753 is hollow and includes ports 755 and 756 that allow liquids or gasses to flow from outside the reservoir tap 712, into the tap shaft 753, and out the nozzle 752. The cartridge 740 may be separable and re-attachable from the inhaled medicament delivery device 710.

The actuator 762 is operatively coupled to the controller 711. The heater 713 is operatively coupled to the controller 711. The actuator 762, under the control of the controller 711, selectively attracts or repels the magnet 761. The magnets 761 are attached to the reservoir tap 712 such that as the actuator 762 attracts or repels the magnet 761 to apply a force to the magnets 761, the reservoir tap 712 moves with the magnets 761. The actuator 762 is attached to the inhaled medicament delivery device 710, but not the reservoir tap 712, such that the reservoir tap 712 may slideably move proximally and distally with respect to the cartridge 740. The reservoir tap 712 may, under the control of the controller 711, slideably move proximally and distally with respect to the cartridge 740 in order to position the reservoir tap 712 such that the ports 755 and/or 756 may be controllably positioned to receive the medicament 720.

FIG. 7 illustrates the actuating of the reservoir tap 712 by the controller 711 (via the interaction of the actuator 762 and the magnets 761) to an inactive position. It should be understood, however, that the controller 711 can position the reservoir tap 712 in various active positions as well as dynamically moving the reservoir tap 712 during an activation cycle. In the position illustrated in FIG. 7A, the ports 755 are occluded by the cartridge seal 743. The ports 756 are positioned more proximal along the tap shaft 753 than the ports 755. Thus, in FIG. 7, the ports 756 are positioned such that they are not capable of receiving the medicament 720.

The controller 711 is operatively coupled to the heater 713. The heater 713 may be an inductive heater. In an embodiment, the heater 713 may move with the reservoir tap 712 as the reservoir tap 712 is slideably positioned and/or moved. Thus, the actuation of the reservoir tap 712 does not change the portion(s) of the reservoir tap 712 being heated by the heater 713. In another embodiment, the heater 713 remains stationary with respect to the cartridge 740. Thus, the actuation of the reservoir tap 712 changes the portion(s) of the reservoir tap 712 (and the tap shaft 753, in particular) being heated by the heater 713.

FIG. 8 is a chart illustrating medicament flow rate. In FIG. 8, curve 801 illustrates an exemplary relative airflow rate versus time. Curve 801 may represent the airflow generated during an inhalation cycle of a subject operating an inhalable medicament delivery device. Curve 802 illustrates an exemplary relative displacement (i.e., position) of a reservoir tap. As can be seen in FIG. 8, the reservoir tap starts at a first position with little or no displacement. In other words, the reservoir tap starts in an inactive position. As the airflow shown by curve 801 increases over time, the reservoir tap is repositioned to a first active position. The reservoir tap remains in this first active position for a first period of time during the inhalation cycle. At a second point in the inhalation cycle, the reservoir tap is repositioned to a second active position. The reservoir tap remains in this second active position for a second period of time during the inhalation cycle. At a third point in the inhalation cycle, the reservoir tap is repositioned to a third active position. The reservoir tap remains in this third active position for a third period of time during the inhalation cycle. Finally, the reservoir tap is repositioned to an inactive position.

Curve 803 illustrates an exemplary medicament flow rate through a reservoir tap. As can be seen in FIG. 8, the inhalation cycle starts with little or no medicament flow. This may be the result of the reservoir tap starting in an inactive position. As the airflow shown by curve 801 increases over time, the medicament flow is set to a first amount by the repositioning of the reservoir tap to the first active position. The medicament flow remains set to the first amount for a first period of time during the inhalation cycle. At a second point in the inhalation cycle, the reservoir tap is repositioned to a second active position. This sets the medicament flow to a second amount for a second period of time during the inhalation cycle. When the reservoir tap is repositioned to the third position at the third point in the inhalation cycle, the medicament flow is reduced to little or none. Thus, during the third period of time during the inhalation cycle, only air is flowing to a subject.

Figure 9A:
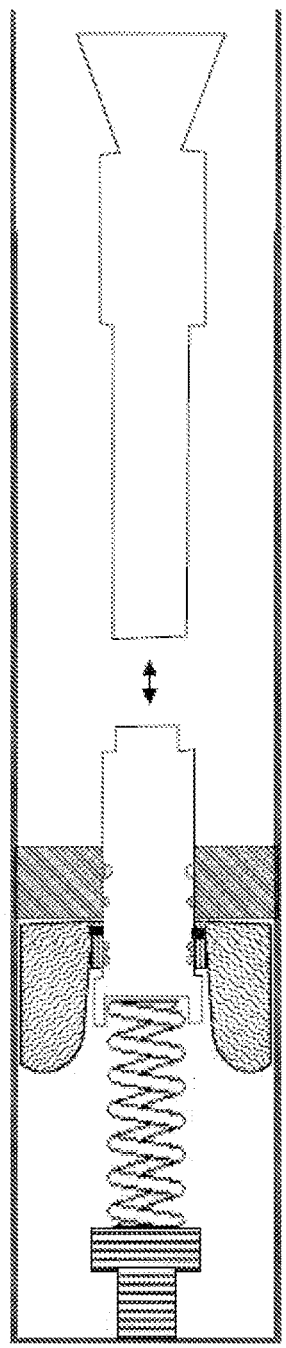
FIG. 9A is an illustration of a medicament cartridge with a reservoir and propellant tap for an inhaled medicament delivery device.

FIG. 9A is an illustration of an embodiment comprising a medicament cartridge with a reservoir and propellant tap for an inhaled medicament delivery device. In FIG. 9A, a cartridge valve assembly that mates to the tap shaft is used instead of a tap shaft that penetrates a seal, wherein the tap shaft is, for example, a component of a cartridge that acts as a valve.

Figure 9B:
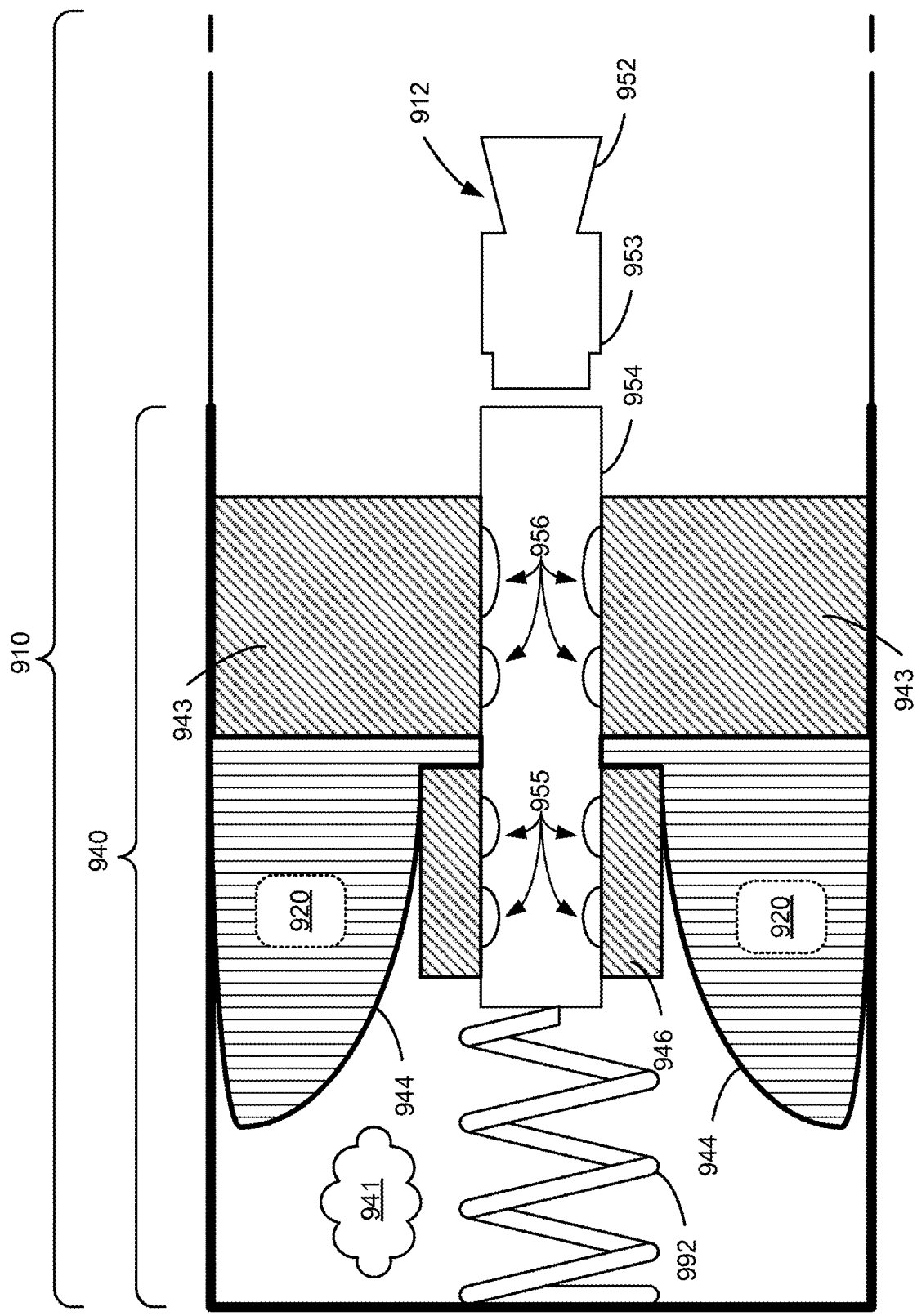
FIG. 9B is an enlarged illustration of a medicament cartridge with reservoir and propellant tap for an inhaled medicament delivery device.

FIG. 9B shows an enlarged illustration of an embodiment of a medicament cartridge with a valve assembly. In FIG. 9B, an inhaled medicament delivery device 910 comprises a cartridge 940 and a nozzle assembly 912. The cartridge 940 includes a bladder 944, a medicament 920, a seal 943, a seal 946, a valve shaft 954, a propellant 941, and a return spring 992. The nozzle assembly 912 includes a shaft 953 and a nozzle 952. The shaft 953 is hollow and is configured to mate with the valve shaft 954. The bladder 944 holds the medicament 920.

The valve shaft 954 includes ports 955 and ports 956 that allow liquids or gasses to flow from the cartridge 940, into the valve shaft 954, into the shaft 953, and out the nozzle 952. In particular, when the valve shaft 954 is moved by the shaft 953 in an active position (i.e., is activated), the propellant 941 gas may flow into one of more of the ports 955, through the valve shaft 954 into the shaft 953, and then out the nozzle 952. Likewise, when the valve shaft 954 is moved by the shaft 953 in an active position (i.e., is activated), the medicament 920 may flow out of the bladder 944 into one or more of the ports 956, through the valve shaft 954 into the shaft 953, and then out the nozzle 952.

In an embodiment, the bladder 920 has an opening that is occluded by the valve shaft 954 when the valve shaft 954 is in the non-activated position. When, the valve shaft 954 is in the activated position, the opening in the bladder 944 aligns with the ports 956 on the valve shaft 954 so that the contents of the bladder 944 may flow into the ports 956.

When activated, the shaft 953 pushes the valve shaft 954 into an activated position within the cartridge 940. When deactivated, the return spring 992 pushes the valve shaft 954 back to an inactive position. When deactivated, the valve shaft 954 is positioned such that the seal 943 occludes the ports 956 and the seal 946 occludes the ports 955, thereby preventing the propellant 941 and the medicament 920 from entering the valve shaft 954. When activated, the shaft 953 pushes the valve shaft 954 into an activated position. In an activated position, one or more of the ports 955 and/or 956 are not occluded.

For example, the valve shaft 954 can be pushed into a position whereby one or more of the ports 955 are exposed to the propellant 941, but the ports 956 are occluded. In this position, only the propellant 941 would be ejected from the nozzle 952. In another example, the valve shaft 954 is pushed into a position whereby the ports 955 are occluded, but the ports 956 are receiving the medicament 920 from the bladder 944. In this position, only the medicament 920 would be provided to the nozzle 952. In another example, the valve shaft 954 is pushed into a position whereby one or more of the ports 955 are exposed to the propellant 941, and the ports 956 are position to receive the medicament 920 from the bladder 944. In this position, both the medicament 920 and the propellant 941 are provided to the nozzle 952.

The cartridge 940 may be separable and re-attachable from the inhaled medicament delivery device 910. The compressible bladder 944 is preferably positioned proximally to the cartridge 940 comprising the pressurized gaseous propellant 941. In an embodiment, the bladder 944 may be distensible and exert a pressure on the liquid wholly or partially (in conjunction with the pressurized gas) to drive the liquid into the nozzle 952.

In an embodiment, the bladder 944 may comprise a plurality of layers, such that between the inner bladder 944 which contains the liquid medicament 920 and the outer bladder 944 there is a space that could contain dry neutralizing agent or absorbent material to render the active excipient inactive or to otherwise absorb and capture the active excipient, a liquid neutralizing agent could also be contained in the space between the outer surface of the inner bladder 944 and the inner surface of the outer bladder 944. The bladder 944 allows for the device to be activated in a fashion that is independent of the orientation in space of the inhaled medicament delivery device 910.

Figure 9C:
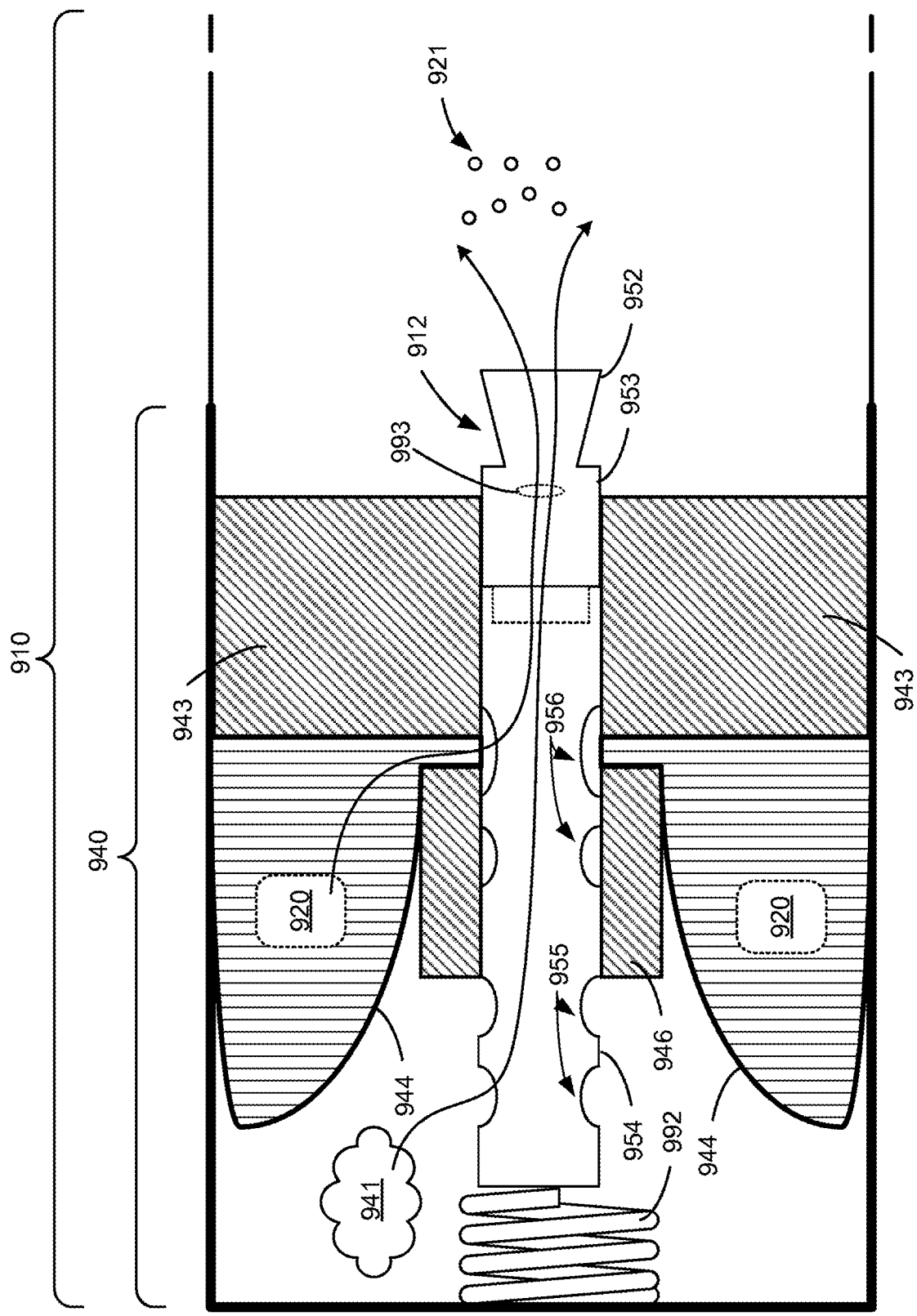
FIG. 9C is an illustration of the activation of a medicament cartridge with reservoir and propellant tap.

FIG. 9C is an illustration of the activation of a medicament cartridge 940 with a reservoir and a propellant tap. As illustrated in FIG. 9C, the valve shaft 954 is positioned such that the ports 955 are exposed to the propellant 941 and one or more ports 956 are positioned to receive the medicament 920 from the bladder 944. As shown by arrows 993, the propellant 941 enters at least one of the ports 955 and the medicament 920 enters at least one of the ports 956. The propellant 941 and the medicament 920 then flow through the valve shaft 954, the shaft 953, and exit the nozzle 952 as an aerosol mixture 921.

In an embodiment, a flow rate is determined by an inhalable medicament delivery device. In an embodiment, the type of port that is positioned within the cartridge is selected to control or determine the flow rate of the medicament through the device. In an embodiment, airflow amplifying features that utilize the Coanda and/or Venturi effects are utilized selectively to generate increases in flow rate and/or amounts. In an embodiment, a valve system is configured to selectively cover and expose the openings on various ports of different sizes in order to control the flow of medicament through the device. In an embodiment, a flow rate of a medicament delivered by a medicament delivery device comprises about the same flow rate as a flow rate of a medicament delivered by a jet nebulizer. In an embodiment, a flow rate of a medicament delivered by a medicament delivery device comprises about the same flow rate as a flow rate of a medicament delivered by a standard inhaler or metered dose inhaler. In an embodiment, a flow rate of a medicament delivered by a medicament delivery device comprises about the same flow rate as the flow of smoke or aerosol delivered by a cigarette.

Figure 10A:
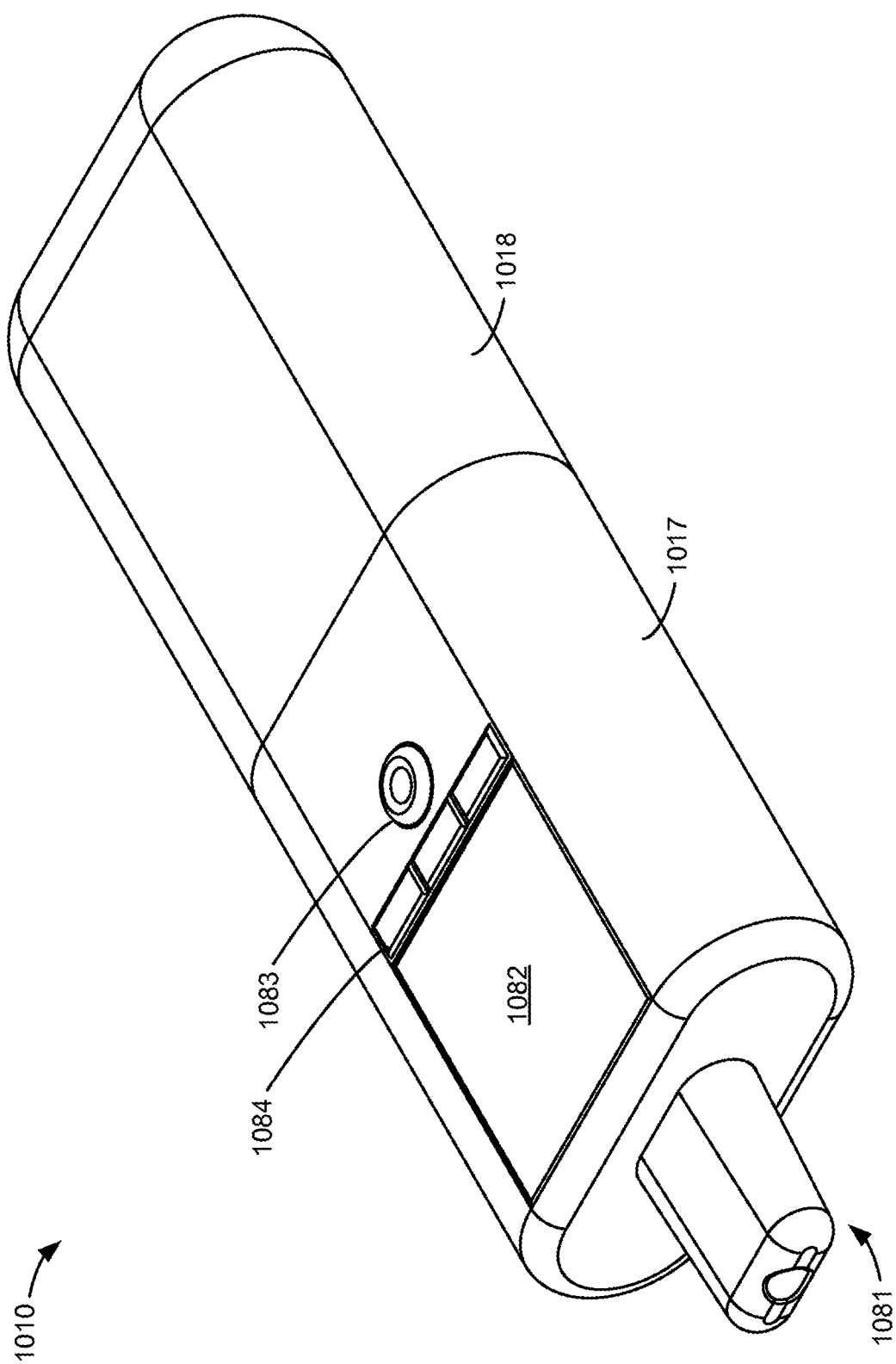
FIG. 10A is an isometric exterior view of an inhalable medicament delivery device.

FIG. 10A is an exterior view of an embodiment of an inhaled medicament delivery device. In FIG. 10A, the inhaled medicament delivery device 1010 comprises a main body 1017, a cartridge cover 1018, a mouthpiece cover 1081, a display 1082, a primary button 1083, and secondary buttons 1084. The main body 1017 and the cartridge cover 1018 may be comprised of different material such as metals, alloys, plastics, polymers, ceramics, or a combination of such materials. The main body 1017 and the cartridge cover 1018 are illustrated as having a cubic or square or rectangular shape, however, other shapes for are possible such as cylindrical, elliptical, ovoid, or the like. The mouthpiece cover 1081 is located on the most proximal aspect of the inhaled medicament delivery device 1010 for engaging a subject's lips to form a seal such that the subject may inhale a vaporized aerosol from the inhaled medicament delivery device 1010 into the mouth, airways, and lungs. The mouthpiece cover 1081 may be comprised of silicon, rubber, plastic, polymer, ceramic, metal, or other materials. The mouthpiece cover 1081 may be comprised of materials that resist or impede the growth of bacteria, such as materials comprised of or containing antimicrobial agents. The mouthpiece cover 1081 may be configured to be easily removable and replaceable by the subject such that the mouthpiece cover 1081 may be exchanged for a new mouthpiece cover 1081. The mouthpiece cover 1081 may be disposable or reusable. The mouthpiece cover 1081 may be of a material that can be sanitized with sanitizing agents such as alcohol or similar agents. The mouthpiece cover 1081 may be cleaned by heat sanitization such as boiling in water or through the application of steam.

The inhaled medicament delivery device 1010 is intended to be operated by the subject using a single hand. The inhaled medicament delivery device 1010 can be operated by bringing the mouthpiece cover 1081 to the lips and activating the inhaled medicament delivery device 1010 through the use of the primary button 1083 (illustrated), a switch, sensor, and/or a combination. The cartridge cover 1018 serves as a cover housing a cartridge. The cartridge cover 1018 and the main body 1017 comprise the majority of the outer surface of the inhaled medicament delivery device 1010.

Figure 10B:
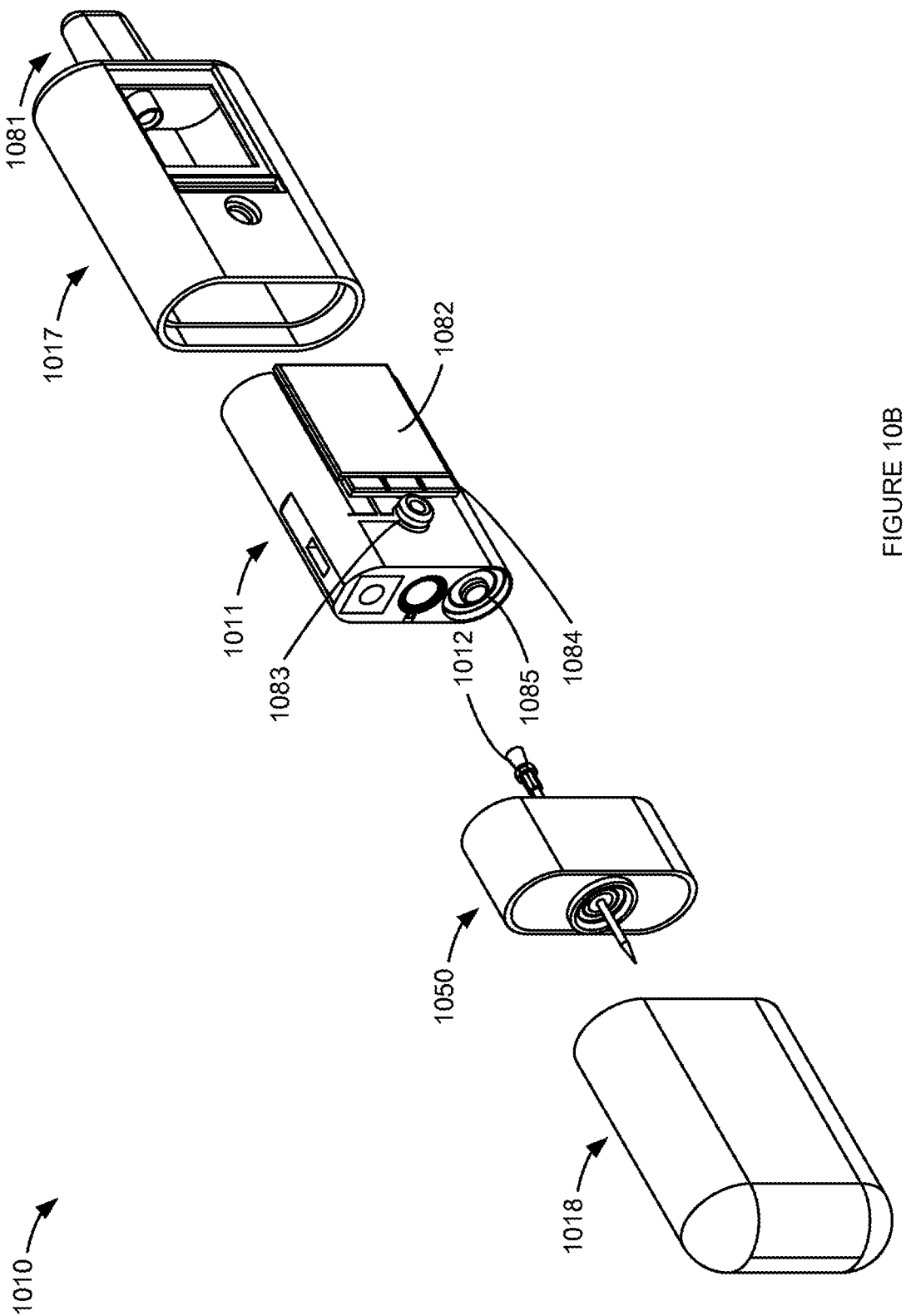
FIG. 10B illustrates an isometric exploded view of an inhalable medicament delivery device.

FIG. 10B illustrates an exploded view of an embodiment of an inhaled medicament delivery device 1010. In FIG. 10B the parts of inhaled medicament delivery device 1010 illustrated include the reservoir tap 1012, the cartridge cover 1018, a valve assembly 1050, a battery and electronics assembly 1011, a main body 1017, and a mouthpiece cover 1081.

FIG. 10C illustrates an exploded view of an embodiment of a cartridge cover 1018 and a cartridge 1040 for an inhaled medicament delivery device 1010. In FIG. 10C, the parts of the inhaled medicament delivery device 1010 illustrated include the cartridge cover 1018 and the cartridge 1040. The cartridge 1040 includes a cartridge filling plug 1041. The cartridge filling plug 1041 allows the cartridge 1040 to be refilled with medicament, propellant, or both. In an embodiment, there may be more than one cartridge filling plug 1041.

Figure 10D:
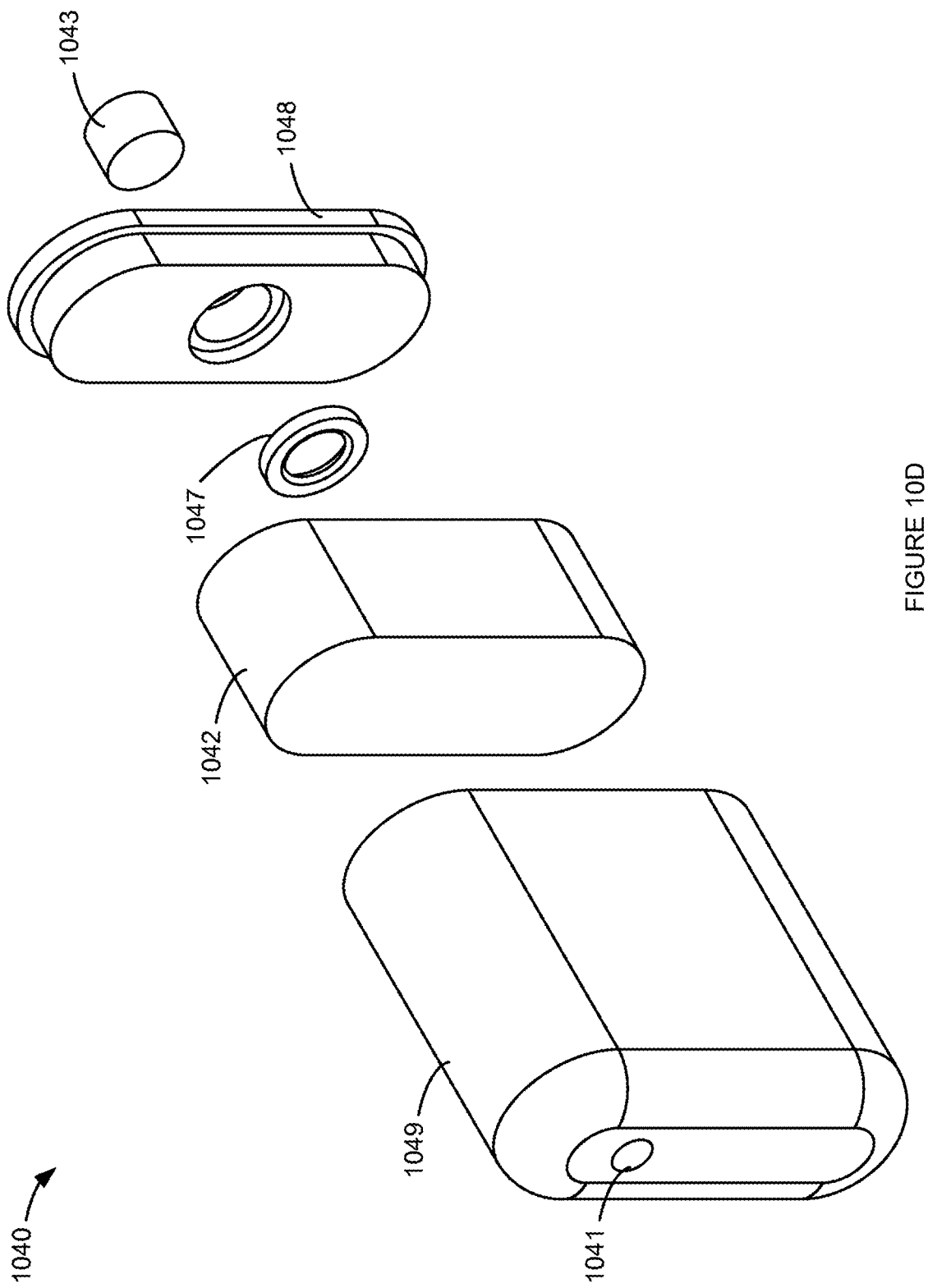
FIG. 10D illustrates an isometric exploded view of a cartridge for an inhalable medicament delivery device.

FIG. 10D illustrates an exploded view of an embodiment of a cartridge 1040 for an inhaled medicament delivery device 1010. In FIG. 10D, the parts of the cartridge 1040 illustrated include a cartridge filling plug 1041, a gas cartridge 1049, a porous reservoir 1042, a septum retainer 1047, a septum 1043, and a cartridge septum housing 1048.

The gas cartridge 1049 may hold a gas propellant such as carbon dioxide ($CO_2$). The gas is held in the cartridge 1040 under pressure such as to provide a positive pressure that drives a liquid formulation in the cartridge 1040 out of the cartridge 1040 through a nozzle to generate an aerosol. Interior to the gas cartridge 1049 is the porous reservoir 1042 that occupies the distal area of the cartridge 1040. The porous reservoir 1042 serves to hold, retain, or otherwise trap a liquid formulation in such a manner that the gas held in the cartridge 1040 is forced through the porous reservoir 1042, and as a result, displaces the liquid out of the porous reservoir 1042 for delivery to a hollow nozzle shaft and then to a nozzle.

The porous reservoir 1042 could be comprised of porous or matrix materials that are hydrophobic and have the capability of retaining the liquid formulation through capillary action or similar means in void spaces in the matrix or pores in the porous material. Materials such as ceramics, glasses, polymers, or plastics may be suitable for the application. The porous reservoir 1042 may allow for the inhaled medicament delivery device 1010 to be operated regardless of orientation as the porous reservoir 1042 containing the liquid formulation maintains the liquid formulation in a proximal orientation to an outlet port. The porous reservoir 1042 may be omitted in some embodiments where the liquid formulation is brought into a miscible solution with a gaseous propellant.

The porous reservoir 1042 may contain encapsulated absorbents or neutralizing agents (not illustrated in FIGS. 10A-10L) such as to prevent intentional or unintentional access or contact with a liquid formulation. An encapsulated absorbent such as charcoal can be encased in a hydrophobic casing such as a plastic, polymer, ceramic, or glass such that if the cartridge 1040 was accessed and the porous reservoir 1042 was removed, the encapsulation would rupture or otherwise allow the absorbent or neutralizing agent to come into contact with the liquid formulation and render the liquid formulation inaccessible or functionally neutralized.

The cartridge 1040 may be sealed at the proximal aspect by the cartridge septum housing 1048 that also engages with the septum 1043. The septum 1043 is comprised of a malleable material such as a silicon rubber or similar. In an embodiment, the septum 1043 is comprised of a self-healing material such as a silicon plug. The self-healing material allows for a nozzle shaft to slide in the proximal to distal respect and enter the cartridge 1040. When the inhaled medicament delivery device 1010 is not in use, a port or ports present on the lateral aspect of the nozzle shaft are occluded or otherwise blocked by the septum 1043. This orientation functionally seals the cartridge 1040 such that the liquid formulation cannot escape the cartridge 1040.

Figure 10E:
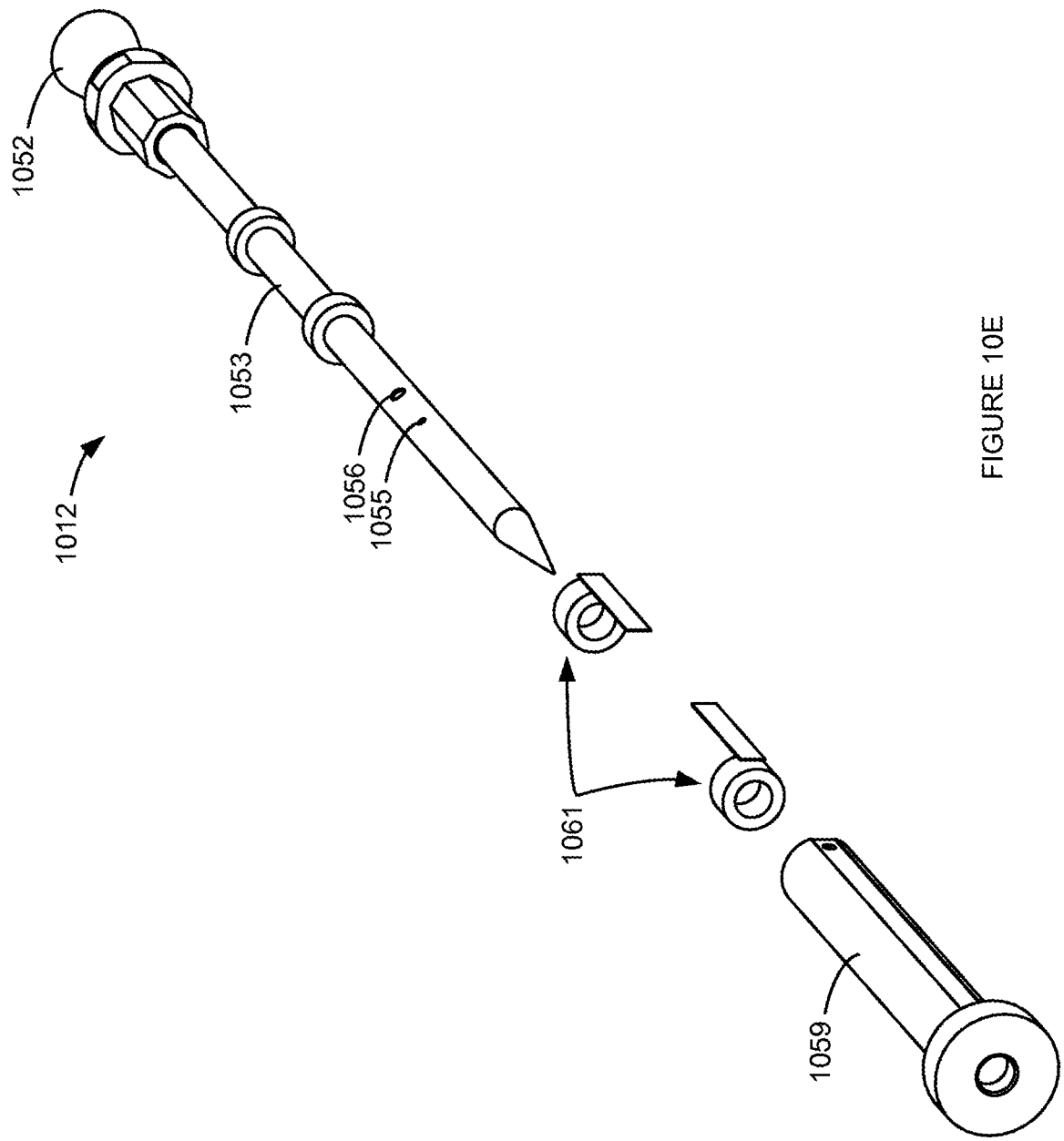
FIGS. 10E and 10F illustrate an exploded view of an embodiment of a reservoir tap assembly for an inhalable medicament delivery device.
Figure 10F:
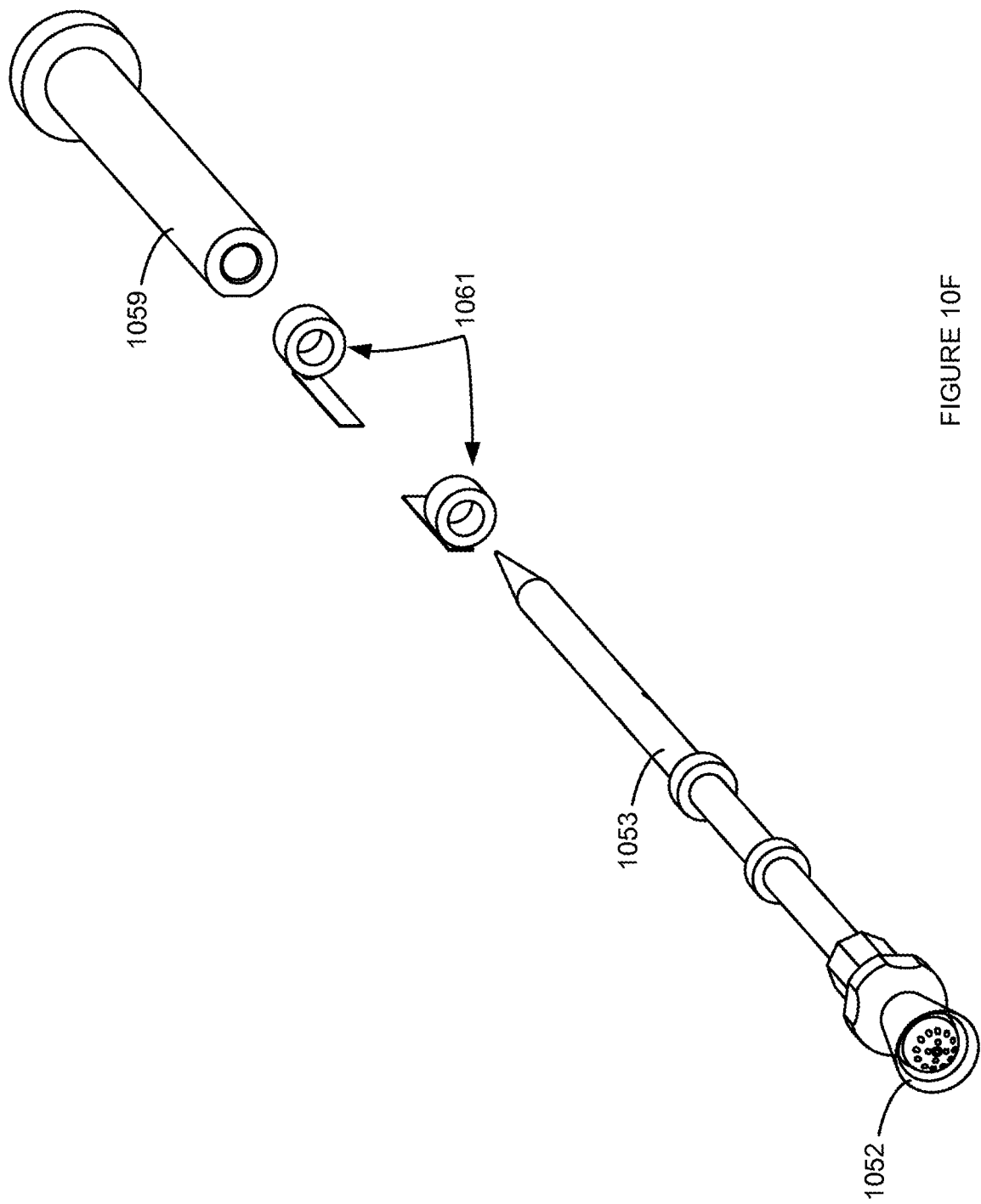

FIGS. 10E and 10F illustrate exploded views of an embodiment of a reservoir tap 1012 assembly for an inhaled medicament delivery device 1010. The parts of the reservoir tap 1012 illustrated include a nozzle 1052, a tap shaft 1053, ports 1055, ports 1056, and magnets 1061. The reservoir tap 1012 may be disposed in a sleeve 1059 to allow slideable movement in the proximal and distal directions. The tap shaft 1053 includes a hollow cavity that allows fluid to flow from the ports 1055 and/or 1056 to the nozzle 1052. The magnets 1061 may interact with an actuator in order to move or position the reservoir tap 1012 relative to the septum 1043 and the cartridge 1040.

Figure 10G:
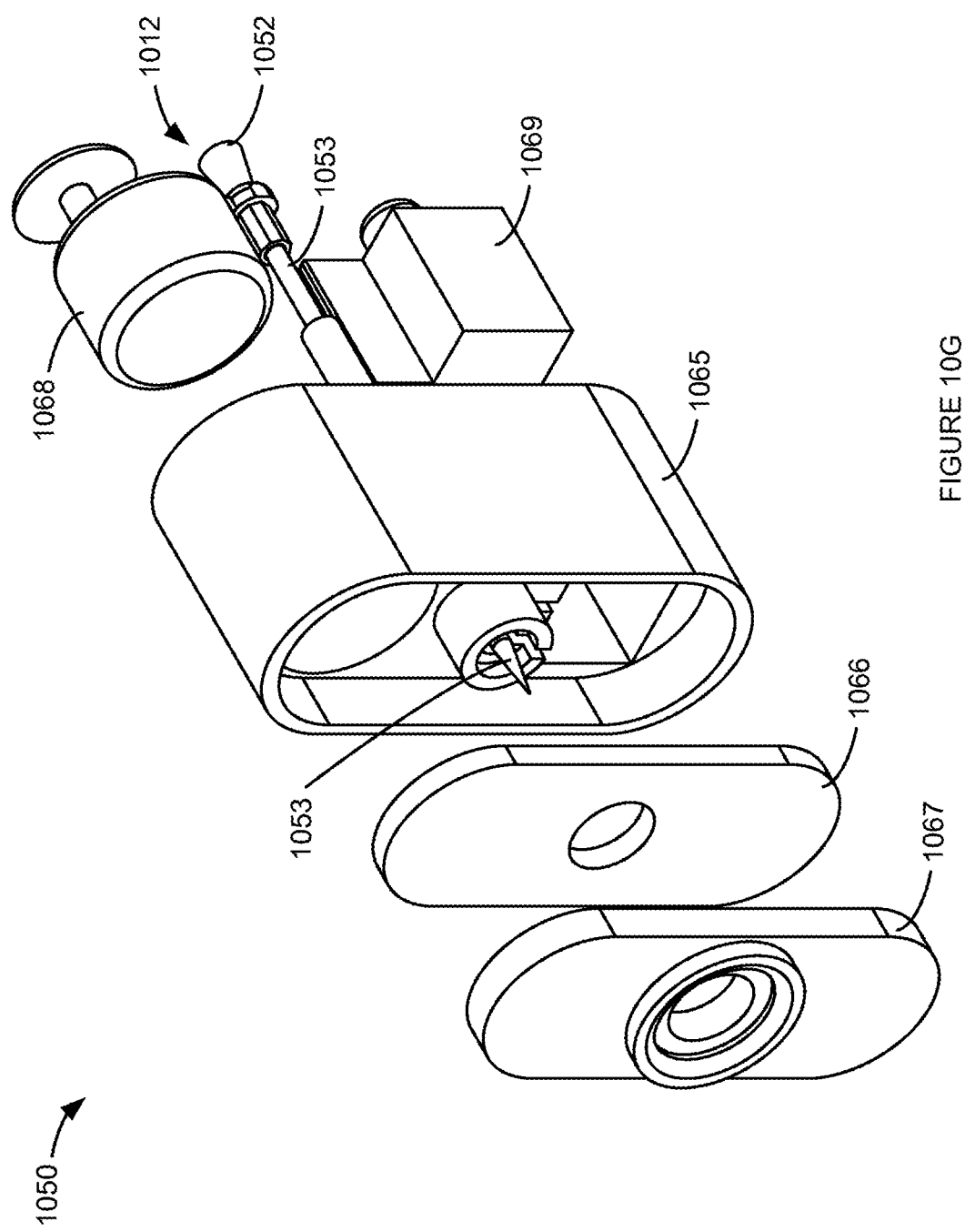
FIG. 10G illustrates an exploded view of an embodiment of a valve assembly for an inhalable medicament delivery device.

FIG. 10G illustrates an exploded view of an embodiment of a valve assembly 1050 for an inhaled medicament delivery device 1010. In FIG. 10G, the parts of the valve assembly 1050 illustrated include a valve housing lid 1067, a printed circuit board (PCB) 1066, a valve housing 1065, an electronic module 1069, and a capacitor 1068. In an embodiment, the capacitor 1068 is a supercapacitor.

Figure 10H:
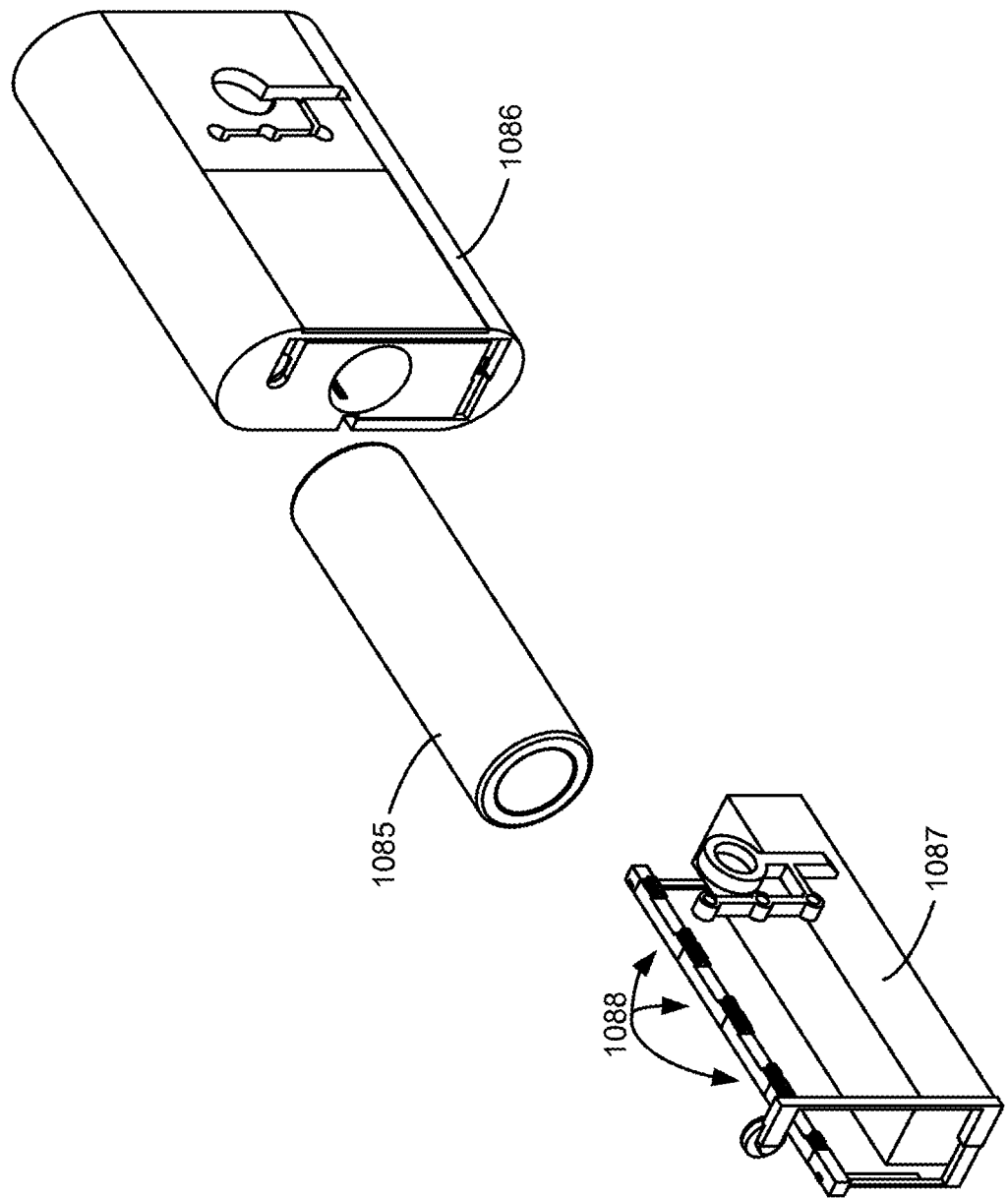
FIG. 10H illustrates an exploded view of an embodiment of a battery and electronics assembly for an inhalable medicament delivery device.

FIG. 10H illustrates an exploded view of an embodiment of a battery and electronics assembly 1011 for an inhaled medicament delivery device 1010. In FIG. 10G, the parts of the battery and electronics assembly 1011 illustrated include a controller 1087, heater contacts 1088, a battery 1085, and a housing 1086. The heater contacts 1088 are electrically coupled to the controller 1087. In an embodiment, the heater contacts 1088 include a plurality of heater contacts 1088 that allow for the selective activation of separate heating elements by the controller 1087.

Figure 11:
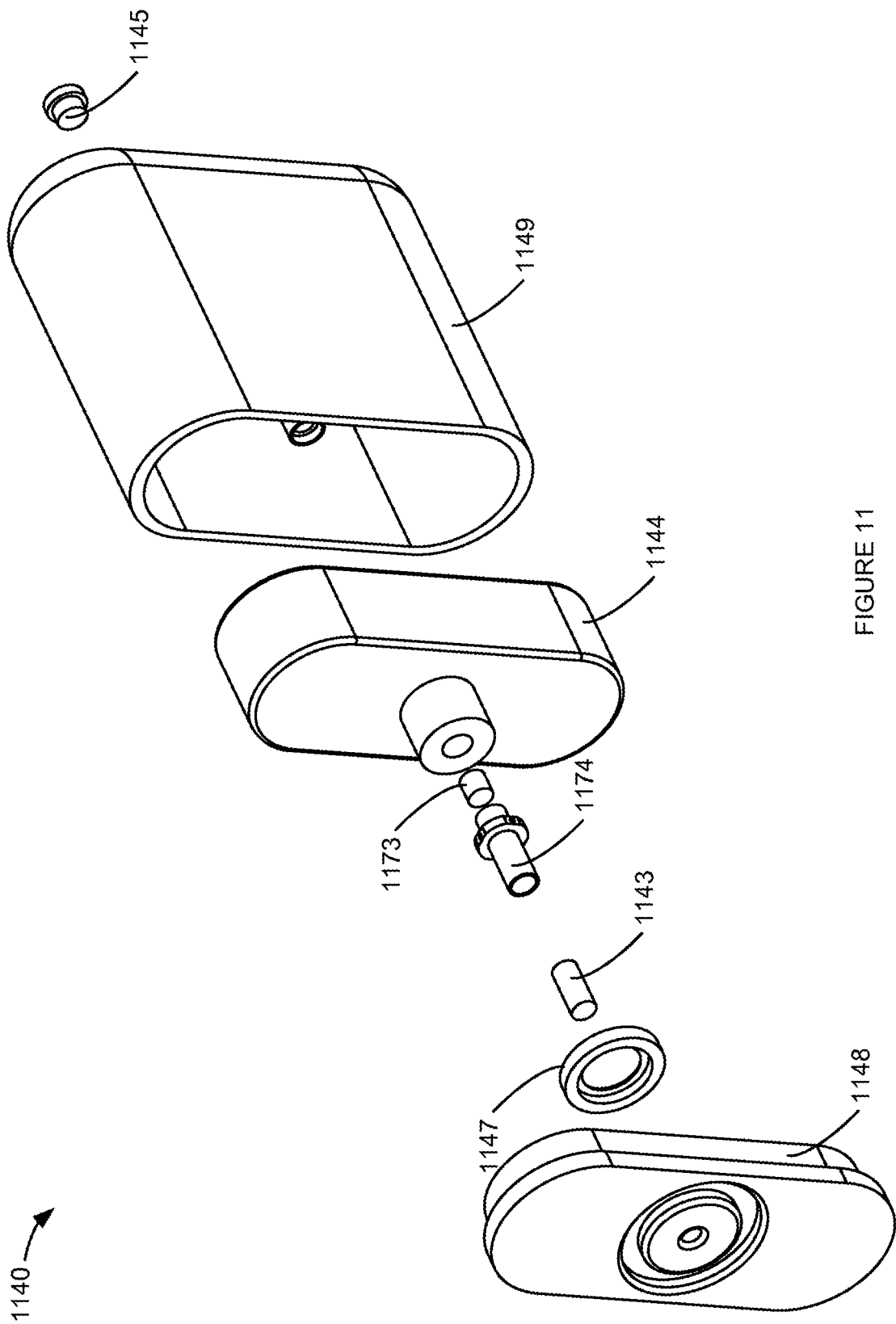
FIG. 11 illustrates an isometric exploded view of a cartridge for an inhalable medicament delivery device.

FIG. 11 illustrates an exploded view of an embodiment of a cartridge for an inhaled medicament delivery device. In FIG. 11, the parts of a cartridge 1140 illustrated include a cartridge filling plug 1145, a gas cartridge 1149, a bladder 1144, a septum retainer 1147, an outer septum 1143, an inner septum 1173, a septum separator 1174, and a cartridge lid 1148.

Figure 12:
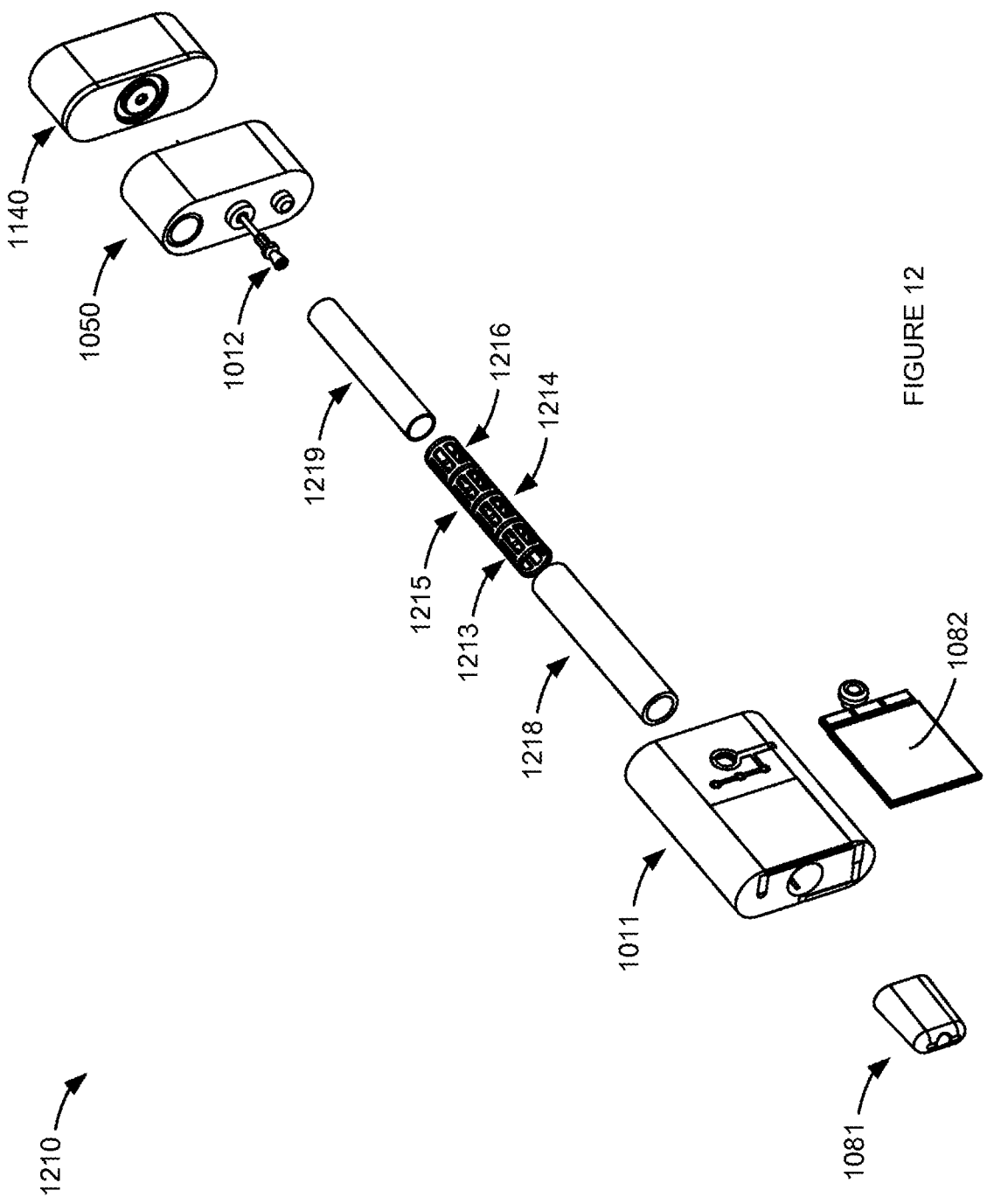
FIG. 12 illustrates an isometric exploded view of an inhalable medicament delivery device.

FIG. 12 illustrates an exploded view of an embodiment of an inhaled medicament delivery device 1210. In FIG. 12 the parts of the inhaled medicament delivery device 1210 illustrated include a cartridge 1140, a valve assembly 1050, a reservoir tap 1012, an aspiration tube 1219, a heat reflector 1218, heater segments 1213, 1214, 1215, and 1216, a battery and electronics assembly 1011, a display 1082, and a mouthpiece cover 1081.

In an embodiment, an aerosol generated by the nozzle of the reservoir tap 1012 enters the aspiration tube 1219, which is circumferential to the nozzle. The aspiration tube 1219 conducts the generated aerosol to the mouthpiece. The aspiration tube 1219 may be heated partially or throughout the length of the aspiration tube 1219 by heater segments 1213-1216. The degree of heating along the length of the aspiration tube 1219 may be modulated as to optimize the vaporization or thermal modulation of the aerosol to achieve the desired particle size for delivery of the medicament to the lungs or other desired airway region. In an embodiment, the aspiration tube 1219 is heated from the outer surface of the tube by one or more of heater segments 1213-1216 such that the aerosol does not come into contact directly with the heating element or elements. The heat reflector 1218 help focus thermal energy into the aspiration tube 1219.

The aspiration tube 1219 may be comprised of ceramic, glass, metals, alloys or other suitable materials. The aspiration tube 1219 may be heated by a separate tube containing heater segments or otherwise radiating heat and/or infrared radiation. Thus, the aspiration tube 1219 may be considered to be a black body absorber of heat and/or infrared radiation.

The heater segments 1213-1216 may be comprised of a coil, or be printed, plated, or otherwise directly applied or affixed to the inner or outer surface of the aspiration tube 1219, or be contained within the wall of aspiration tube 1219. The heater segments 1213-1216 may be isolated from the aspiration tube by a thin covering or coating of material that may be the same material composition of the aspiration tube 1219 or another suitable material such as a glass or ceramic coating, such that the aerosol does not directly contact the heater element material, or such that the heater element material is encased by the coating material such that the heater material cannot be released into the aerosol or react with the aerosol. The heater segments 1213-1216 may generate heat through a variety of methods. In an embodiment, the heat is generated through the emission or generation of infrared energy. In an embodiment, the aspiration tube 1219 is comprised of a material that reduces thermal loss from the heating element or elements by reflecting or otherwise reducing the loss of thermal energy, such as infrared energy, through the selection of materials that reflect the infrared energy into the aspiration tube 1219. In an the reflector 1218 is comprised of a material that reduces thermal loss from the heating element or elements by reflecting or otherwise reducing the loss of thermal energy, such as infrared energy, through the selection of materials that reflect the infrared energy into the aspiration tube 1219.

Figure 13:
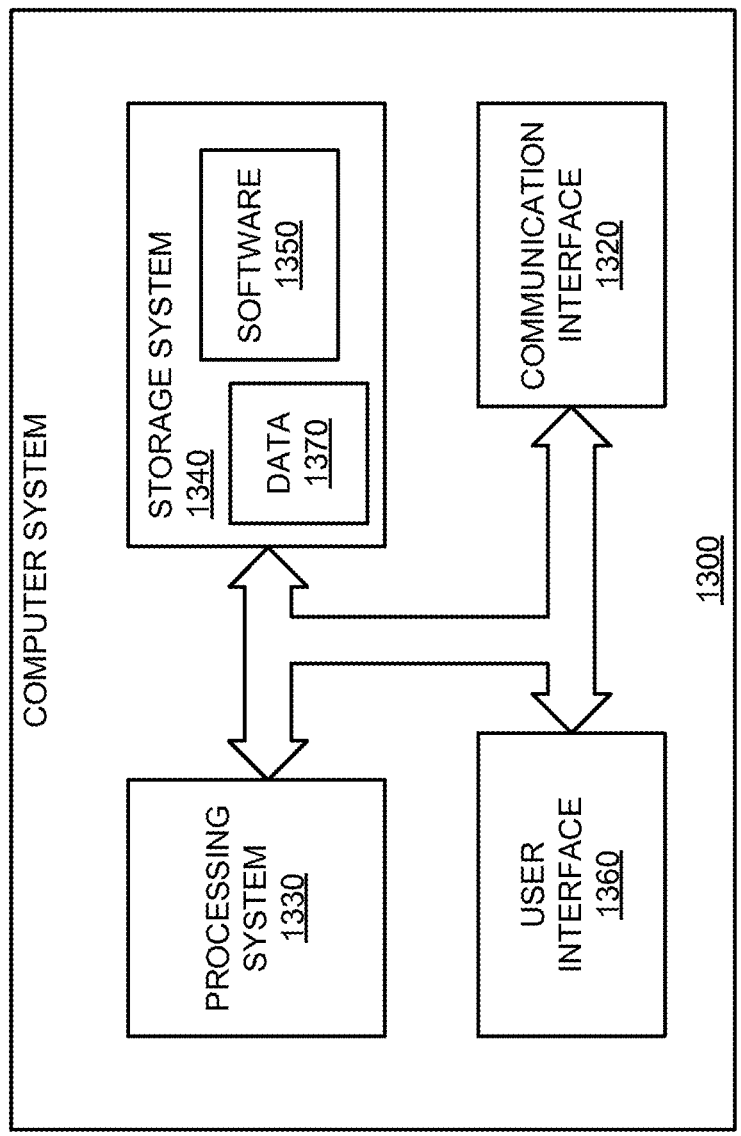
FIG. 13 is a block diagram of a computer system.

FIG. 13 illustrates a block diagram of an embodiment of a computer system. The controllers 211, 611, and/or 711 may be or include a computer system. Computer software may implement one or more of the control functions and/or display functions described herein. A computer system 1300 includes a communication interface 1320, a processing system 1330, a storage system 1340, and a user interface 1360. The processing system 1330 is operatively coupled to the storage system 1340. The storage system 1340 stores software 1350 and data 1370. The processing system 1330 is operatively coupled to the communication interface 1320 and the user interface 1360. The computer system 1300 may comprise a programmed general-purpose computer. The computer system 1300 may include a microprocessor. The computer system 1300 may comprise programmable or special purpose circuitry. The computer system 1300 may be distributed among multiple devices, processors, storage, and/or interfaces that together comprise elements 1320-1370.

The communication interface 1320 may comprise a network interface, modem, port, bus, link, transceiver, or other communication device. The communication interface 1320 may be distributed among multiple communication devices. The processing system 1330 may comprise a microprocessor, microcontroller, logic circuit, or other processing device. The processing system 1330 may be distributed among multiple processing devices. The user interface 1360 may comprise a keyboard, mouse, voice recognition interface, microphone and speakers, graphical display, touch screen, or other type of user interface device. The user interface 1360 may be distributed among multiple interface devices. The storage system 1340 may comprise a disk, tape, integrated circuit, RAM, ROM, EEPROM, flash memory, network storage, server, or other memory function. The storage system 1340 may include computer readable medium. The storage system 1340 may be distributed among multiple memory devices.

The processing system 1330 retrieves and executes the software 1350 from the storage system 1340. Processing system 1330 may retrieve and store data 1370. The processing system 1330 may also retrieve and store data 1370 via the communication interface 1320. The processing system 1330 may create or modify software 1350 or data 1370 to achieve a tangible result. The processing system 1330 may control communication interface 1320 or user interface 1360 to achieve a tangible result. The processing system 1330 may retrieve and execute remotely stored software via the communication interface 1320.

The software 1350 and remotely stored software may comprise an operating system, utilities, drivers, networking software, and other software typically executed by a computer system. The software 1350 may comprise an application program, applet, firmware, or other form of machine-readable processing instructions typically executed by a computer system. When executed by the processing system 1330, the software 1350 or remotely stored software may direct the computer system 1300 to operate.

In an embodiment, an inhalable medicament delivery device comprises a power module. In an embodiment, a power module comprises a CPU, a processor, and at least one sensor.

In an embodiment, an inhalable medicament delivery device comprises one or more temperature sensors. In an embodiment, one or more temperature sensors are coupled to a processor that is configured to receive temperature data form the one or more sensors. In an embodiment, the processor is further configured to modify a temperature of one or more heaters in response to temperature data received from one or more thermal sensors.

In an embodiment, an inhalable medicament delivery device comprises one or more sensors configured to sense ambient data. In an embodiment, a sensor is configured to sense ambient temperature. In an embodiment, a sensor is configured to sense an ambient pressure. In an embodiment, a sensor is configured to sense an oral temperature of a subject. In an embodiment, one or more sensors configured to sense ambient data are coupled to a processor. In an embodiment, a processor is further configured to modify a temperature of one or more heaters in response to temperature or pressure data received from one or more ambient sensors. In an embodiment, a processor is configured to calibrate and adjust the device in response to environmental factors that may be measured by one or more ambient sensors.

In an embodiment, an inhalable medicament delivery device comprises one or more flow sensors. In an embodiment, one or more flow sensors sense a flow rate of a medicament as the medicament travels through the inhalable medicament delivery device. In an embodiment, one or more sensors configured to sense flow rate data are coupled to a processor. In an embodiment, a processor is further configured to modify a temperature of one or more heaters in response to flow rate data received from one or more flow sensors. In an embodiment, a processor is further configured to modify a flow rate in response to flow rate data received from a flow rate sensor. For example, in response to flow rate data received from a flow sensor, a processor may cause a second port to be advanced into the cartridge, thus increasing the medicament flow rate through the nozzle and aspiration tube as described herein. For example, in response to flow rate data received from a flow sensor, a processor may cause a second port to be withdrawn out of the cartridge, thus decreasing the medicament flow rate through the nozzle and aspiration tube as described herein.

In an embodiment, an inhalable medicament delivery device comprises one or more biometric sensors. In an embodiment, one or more biometric sensors are configured to identify a subject. In an embodiment, one or more biometric sensors are coupled with a processor. In an embodiment, a processor is further configured to activate an inhalable medicament device only if a biometric sensor provides a signal comprising a confirmation of an identity of a subject.

In an embodiment, use of the inhalable medicament delivery device comprises one or more of the following steps: A subject obtains an inhalable medicament device. In a variation, the inhalable medicament device is configured, ahead of use, to provide a particular medicament to a subject in a particular fashion. In a variation, the inhalable medicament delivery device is configured so that one or more of a flow rate, temperature, and aerosol particle size of a medicament to be delivered to a patient is set before the device is used. In a variation, one or more biometric sensors confirm an identity of a subject, and allow the inhalable medicament delivery device to be activated in response to confirming the identity of a subject through the biometric sensor. In a variation, comprising of an embodiment wherein the cartridge and housing are separate components, a subject couples a cartridge containing a medicament to a housing of the inhalable medicament delivery device. In a variation, a subject places the mouthpiece of the device either against his lips or close to his mouth. In a variation, a subject presses a button or touches a touch screen that causes the ejection of the medicament from the cartridge and delivery of the medicament of the subject through the aspiration tube. In a variation, a subject controls the flow rate of the delivered medicament through a user interface. In a variation, after use the device is configured to self-sterilize, by, for example, heating the aspiration tube.

Compositions

In an embodiment, an aerosolized medicament generated by an inhaled medicament delivery device may comprise droplets or may be mixed with vapor forming an aerosol and vapor mixture. Alternatively, the aerosolized medicament may be entirely vaporized within the device.

An aerosol typically comprises liquid droplets suspended in a gas. The liquid droplets within the aerosol generated by the inhaled medicament delivery device, as described herein, comprises medicament particles and may further comprise an excipient. The aerosol generated by the device may be further converted to a vapor by, for example, heating the aerosol. The term "vapor" may be understood to mean the gaseous form of the aerosol. An aerosol may be, for example, heated to a degree wherein the aerosol is partially converted to a vapor, and partially remains an aerosol, thus forming an aerosol and vapor mixture. The droplets within the aerosol will typically comprise larger medicament particles than the particles of medicament found within the vapor. The aerosol droplet or particle size, as well as the degree of vaporization, affects the delivery of the medicament.

The droplet sizes within an aerosol or partial vapor may be modified to affect medicament delivery in a predictable way. That is, droplet size can be increased or decreased by modulating the temperature within the aerosol-generating device. Large and small aerosol droplets travel differently, which allows control over medicament delivery through the modulation of aerosol droplet size. For example, larger particles tend not to travel as deeply into the airway and lung as smaller particles. Also, larger particles, when too large, may be expelled. Thus, for example, if delivery of medicament primarily to the upper airways and upper lung lobes were desired, a larger droplet size would be optimal. Alternatively, smaller particles tend to travel deeper in the lungs, and so a smaller droplet or vapor would be optimal for delivery to the lower lung lobes. However, very small droplets travel deep into the lung and are then subsequently exhaled without being absorbed.

One useful way to describe the size of particles within an aerosol is using the Mass Median Aerodynamic Diameter (MMAD) of the particles. The MMAD is equal to the diameter of a particle of average mass of a population. Meaning, the MMAD is the diameter of a particle for which 50% of the aerosol mass is greater in mass than the mass of that particle and the 50% is smaller in mass than the mass of that particle. Three different mechanisms can be used to describe aerosol deposition. The three mechanisms are impaction, sedimentation, and suspension. In impaction, particles of an aerosol tend to continue on a trajectory when they travel through the airway, instead of conforming to the curves of the respiratory tract. Particles with enough momentum are affected by centrifugal force at the points where the airflow suddenly changes directions, colliding with the airway wall. Impaction mainly affects particles larger than 10 µm. Particles larger than 10 µm may tend to deposit in the oropharynx. In sedimentation, particles with sufficient mass are deposited due to gravity when they remain the airway for a sufficient length of time. Lastly, in suspension, the particles of an aerosol move erratically from one place to another in the airways, as a consequence of Brownian diffusion. Suspension tends to affect particles with a smaller MMAD than 0.5 µm in the alveolar spaces wherein airspeed is practically zero. Particles with a smaller MMAD than 0.5 µm are typically not deposited and are expelled upon exhalation.

Particles with, for example, a MMAD between 10-15 µm may tend to be deposited in the oropharynx. Particles with, for example, a MMAD measuring between 5 and 10 µm may tend to be deposited in the upper airways. Particles with, for example, a MMAD from 0.5 to 5 µm may tend to be deposited in the lower airways and alveoli. Respiratory treatment to be delivered to the alveoli may thus be achieved using particles with an MMAD between 0.5 and 5 µm. The range of 0.5 and 5 µm is known as the breathable fraction of an aerosol. (Tena, F., Casan Clara, P. Deposition of Inhaled Particles Within the Lungs. Arch Bronconeumol. 2012; 48(7):240-246).

An inhaled medicine intended to penetrate deeply into the lung may, for example, be designed to deliver aerodynamic particle sizes between 0.1 and 5 µm. As above, particle sizes that are too small, for example, <0.1 µm, may result in low deposition due to a high amount exhaled, whereas larger particles may be deposited to an increasing extent in the upper and central airways. A larger particle size may, however, be optimal for an inhaled medicine targeting, for example, the tracheobronchial region.

In terms of deep penetration of a delivered medicament into the lung, hygroscopic effect may also be a consideration. Generally, hygroscopicity is the property of some substances to absorb and exhale humidity depending on the setting in which they are found. This means that a hygroscopic particle can grow larger or smaller in size upon entering into a moist airway, with the consequent modification in the deposition pattern compared to what was initially expected, due to the increase in particle size from hygroscopic effect. That is, a particle may start within a size range that would predict delivery into the alveoli, and due to hygroscopic effect, grow to a size that would make alveolar delivery unlikely. The particle size of an inhaled medicament tends to increase as the inhaled medicament travels through the mouth, oropharynx, and lower respiratory tract of a subject due to, for example, heating of the inhaled medicament. As mentioned above, different size particles travel more efficiently to different portions of the lung. Thus, a medicament can be delivered in submicron partial or complete vapor form so that it will increase inside the pulmonary tract to an optimal or target size. The growth of the particle to the optimal or target particle size within the respiratory tract ensures optimal delivery of medicament to the portion of the lung that most efficiently receives particles of that size.

Thus, for example, for effective deposition of a particle with the final diameter of 3.5 µm, it may be necessary to compensate for hygroscopic effect by delivering a particle of, for example, 0.5 µm with the expectation that it will grow towards a diameter of 3.5 µm while traveling through the oropharynx and airway. (Zarogouldis, P., et al. Vectors for Inhaled Gene Therapy in Lung Cancer Application for Nano Oncology and Safety of Bio Nanotechnology. Int. J. Mol. Sci. 2012, 13, 10828-10862). In general, it is considered that hygroscopic growth may not have much of an effect on particles with a MMAD of less than 0.1 µm; meanwhile hygroscopic effect may be more noticeable in particles with a MMAD larger than 0.5 µm.

The partial or complete vapor of the inhalable medicament provides advantages in terms of delivery of medicament to the lungs and pulmonary vasculature. Smaller particles as, for example, found in a vapor, tend to travel farther through the respiratory tract as compared to an aerosol, because the vapor is, for example, lighter, and, for example, tends to be absorbed to a lesser degree by the proximal tissue of the oropharynx. Generally, the smaller the particle size the further it will penetrate into the respiratory tract, meaning larger particles tend to be delivered most optimally towards the lung apices, midsized particles tend to be best delivered to the mid-lung, and vapor or small particles tend to be delivered best to the lung bases.

Vaporization of the aerosolized medicament is advantageous because, for example, it increases the degree of drug delivery into the lung by, for example, increasing the degree of medicament penetration into the lung. Furthermore, due to its increased gaseous volume of a vapor relative to an aerosol, a vapor provides for better distribution of the medicament throughout the lung tissue relative to an aerosol. Better distribution of the medicament throughout the lung tissue, for example, leads to more even distribution of the medicament in pulmonary vasculature once the medicament is absorbed. More even distribution of the medicament in the pulmonary vasculature may, for example, lead to more efficient medicament delivery of a vapor or partial vapor as compared to an aerosol.

A further advantage of vaporization is a decrease or elimination of tracheal and oropharyngeal stimulation with inhalation of a medicament. When exposed to foreign material, the trachea and oropharynx may be stimulated in a way that would, for example, induce a cough reflex, cause an unpleasant sensation, or decrease the degree of inhalation. Stimulation of the cough reflex may prevent effective delivery of an inhaled medicament when the subject coughs. Because the particles in a vapor are extremely small, there is decreased or eliminated tracheal and oropharyngeal stimulation with the use of a vapor or partial vapor as compared to larger droplets.

Particle Size Distribution

The devices disclosed herein allow for a controlled and reproducible particle size distribution of the aerosol generated. As mentioned previously, the aerosol particle size distribution is related to the amount of heat applied to the aerosol, or the temperature of which the aerosol is heated at upon generation. Controlling the amount of heat applied to the aerosol, or the temperature at which the aerosol is heated, allows for a tighter particle size distribution of the aerosol generated.

Provided herein is a method of delivering an inhaled medicament to a subject, comprising generating an aerosol from the inhaled medicament and heating an aerosol at specific temperature range of about 100° C. to about 285° C. to provide a particle size distribution of the aerosol generated of about 0.1 µm to about 15 µm, wherein the aerosol is delivered to a specific target site of the subject.

Also provided herein is a method of delivering an inhaled medicament to a subject for nicotine replacement therapy comprising generating an aerosol from the inhaled medicament and heating an aerosol at specific temperature range of about 130° C. to about 200° C. to provide a particle size distribution of the aerosol generated of about 0.1 µm to about 15 µm, wherein the aerosol is delivered to a specific target site of the subject.

In some embodiments, the specific temperature range is about 150° C. to about 175° C. to provide a particle size distribution of the aerosol generated of about 0.1 µm to about 15 µm. In some embodiments, the specific temperature range is about 150° C. to about 185° C. to provide a particle size distribution of the aerosol generated of about 0.1 µm to about 15 µm. In some embodiments, the specific temperature range is about 150° C. to about 175° C. to provide a particle size distribution of the aerosol generated of about 0.35 µm to about 0.45 µm. In some embodiments, the specific temperature range is about 150° C. to about 185° C. to provide a particle size distribution of the aerosol generated of about 0.35 µm to about 0.45 µm. In some embodiments, the specific temperature range is about 150° C. to about 175° C. to provide a particle size distribution of the aerosol generated of about 0.4 µm. In some embodiments, the specific temperature range is about 150° C. to about 185° C. to provide a particle size distribution of the aerosol generated of about 0.4 µm. In some embodiments, the specific temperature range is about 150° C. to about 175° C. to provide a particle size distribution of the aerosol generated of about 0.3 µm to about 5 µm. In some embodiments, the specific temperature range is about 150° C. to about 185° C. to provide a particle size distribution of the aerosol generated of about 0.3 µm. to about 5 µm.

In an embodiment, the particle size of the aerosol generated by the inhalable medicament delivery device, as described herein, is greater than about 0.1 µm. In some embodiments, the particle size of the aerosol generated is about 0.1 µm to about 10 µm. In some embodiments, the particle size of the aerosol generated is about 0.1 µm to about 15 µm. In some embodiments, the particle size of the aerosol generated is about 0.5 µm to about 10 µm. In some embodiments, the particle size of the aerosol generated is about 0.4 µm. In some embodiments, the particle size of the aerosol generated is about 0.1 µm, about 0.2 µm, about 0.3 µm, about 0.4 µm, about 0.5 µm, about 0.6 µm, about 0.7 µm, about 0.8 µm, about 0.9 µm, about 1.0 µm, about 1.5 µm, about 2.0 µm, about 2.5 µm, about 3.0 µm, about 3.5 µm, about 4.0 µm, about 4.5 µm, about 5.0 µm, about 5.5 µm, about 6.0 µm, about 6.5 µm, about 7.0 µm, about 7.5 µm, about 8.0 µm, about 8.5 µm, about 9.0 µm, about 9.5 µm, about 10.0 µm, about 10.5 µm, and about 11.0 µm.

In some embodiments, greater than 50% of the particles delivered have a particle size of about 0.4 µm. In some embodiments, greater than 60% of the particles delivered have a particle size of about 0.4 µm. In some embodiments, greater than 70% of the particles delivered have a particle size of about 0.4 µm. In some embodiments, greater than 80% of the particles delivered have a particle size of about 0.4 µm. In some embodiments, greater than 90% of the particles delivered have a particle size of about 0.4 µm.

Provided herein is a method of delivering an inhaled medicament to a subject, comprising generating an aerosol from the inhaled medicament and heating an aerosol at specific temperature range of about 140° C. to about 200° C. to provide a Mass Median Aerodynamic Diameter (MMAD) of the aerosol generated of about 0.1 µm to about 15 µm, wherein the aerosol is delivered to a specific target site of the subject.

Also provided herein is a method of delivering an inhaled medicament to a subject for the treatment of nicotine replacement therapy comprising generating an aerosol from the inhaled medicament and heating an aerosol at specific temperature range of about 140° C. to about 200° C. to provide a Mass Median Aerodynamic Diameter (MMAD) of the aerosol generated of about 0.1 µm to about 15 µm, wherein the aerosol is delivered to a specific target site of the subject.

In some embodiments, the specific temperature range is about 150° C. to about 175° C. to provide a Mass Median Aerodynamic Diameter (MMAD) of the aerosol generated of about 0.1 µm to about 15 µm. In some embodiments, the specific temperature range is about 150° C. to about 185° C. to provide a particle size distribution of the aerosol generated of about 0.1 µm to about 15 µm.

In some embodiments, the specific temperature range is about 150° C. to about 175° C. to provide a Mass Median Aerodynamic Diameter (MMAD) of the aerosol generated of about 0.35 µm to about 0.45 µm. In some embodiments, the specific temperature range is about 150° C. to about 185° C. to provide a Mass Median Aerodynamic Diameter (MMAD) of the aerosol generated of about 0.35 µm to about 0.45 µm. In some embodiments, the specific temperature range is about 150° C. to about 175° C. to provide a Mass Median Aerodynamic Diameter (MMAD) of the aerosol generated of about 0.4 µm. In some embodiments, the specific temperature range is about 150° C. to about 185° C. to provide a Mass Median Aerodynamic Diameter (MMAD) of the aerosol generated of about 0.4 µm. In some embodiments, the specific temperature range is about 150° C. to about 175° C. to provide a Mass Median Aerodynamic Diameter (MMAD) of the aerosol generated of about 0.3 µm to about 5 µm. In some embodiments, the specific temperature range is about 150° C. to about 185° C. to provide a Mass Median Aerodynamic Diameter (MMAD) of the aerosol generated of about 0.3 µm to about 5 µm.

In an embodiment, the Mass Median Aerodynamic Diameter (MMAD) of the aerosol generated by the inhalable medicament delivery device, as described herein, is greater than about 0.1 µm. In some embodiments, the Mass Median Aerodynamic Diameter (MMAD) of the aerosol generated is about 0.1 µm to about 10 µm. In some embodiments, the Mass Median Aerodynamic Diameter (MMAD) of the aerosol generated is about 0.1 µm to about 15 µm. In some embodiments, the Mass Median Aerodynamic Diameter (MMAD) is about 0.5 µm to about 10 µm. In some embodiments, the Mass Median Aerodynamic Diameter (MMAD) of the aerosol generated is about 0.4 µm. In some embodiments, the a Mass Median Aerodynamic Diameter (MMAD) of the aerosol generated is about 0.1 µm, about 0.2 µm, about 0.3 µm, about 0.4 µm, about 0.5 µm, about 0.6 µm, about 0.7 µm, about 0.8 µm, about 0.9 µm, about 1.0 µm, about 1.5 µm, about 2.0 µm, about 2.5 µm, about 3.0 µm, about 3.5 µm, about 4.0 µm, about 4.5 µm, about 5.0 µm, about 5.5 µm, about 6.0 µm, about 6.5 µm, about 7.0 µm, about 7.5 µm, about 8.0 µm, about 8.5 µm, about 9.0 µm, about 9.5 µm, about 10.0 µm, about 10.5 µm, or about 11.0 µm.

Medicaments

In a variation, the device generates an aerosol comprising an inhalable medicament. An aerosol may comprise a colloidal suspension of particles or liquid droplets suspended in for example a liquid or gas. A medicament may comprise any substance used to treat a subject. A medicament may, for example, comprise a pharmaceutical, a biological agent, or any other therapeutic compound. An inhalable medicament may comprise a formulation that is inhaled by a subject for the purpose of treating a medical condition or symptom. An inhalable medicament may comprise a formulation that is inhaled by a subject for the purpose of smoking cessation or nicotine replacement therapy. A subject capable of using the described device may comprise a human or animal.

Nicotine Replacement Therapy

The medicament may comprise, for example, nicotine for use in, for example, nicotine replacement therapy.

Anxiolytics

The medicament may comprise, for example, an anxiolytic. Non-limiting examples of anxiolytics suitable for delivery with the device described herein comprise alprazolam, bromazepam, chlordiazepoxide, clonazepam, clorazepate, diazepam, flurazepam, lorazepam, oxazepam, temazepam, and triazolam.

Non-Opioids

The medicament may comprise, for example, a non-opioid based pain medication. Non-limiting examples of non-opioid based pain medications suitable for delivery with the device described herein comprise acetylsalicylic acid, acetaminophen, and ketorolac tromethamine.

Opioids

Opioids may, for example, be delivered by the inhalable medicament delivery device described herein with similar or improved bioavailability. Non-limiting examples of opioids suitable for delivery with the described device include Fentanyl/Fentanyl citrate, Morphine sulfate (MS Contin), Codeine, Tramadol (Ultram), Meperidine (Demerol), Hydromorphone (Dilaudid), Methadone (Dolophine), Oxycodone (Roxicodone), Oxycodone/Acetaminophen (Percocet), Oxycodone/Aspirin (Percodan), Hydrocodone/Acetaminophen (Lortab, Norco, Hycet), and Tramadol/Acetaminophen (Ultracet). The bioavailabilities of Codeine, Methadone (Dolophine), Oxycodone (Roxicodone), Oxycodone/Acetaminophen (Percocet), Oxycodone/Aspirin (Percodan), Hydrocodone/Acetaminophen (Lortab, Norco, Hycet), and Tramadol/Acetaminophen (Ultracet) are similar when administered PO, and when administered with the inhalable medicament delivery device described herein. The bioavailability of Fentanyl/Fentanyl citrate is typically around 47-71% when administered PO, and when delivered as an inhalable medicament with the device described herein, the bioavailability is greater than 47%. The bioavailability of Morphine sulfate (MS Contin) is typically around 20-40% when administered PO, and when delivered as an inhalable medicament with the device described herein, the bioavailability is greater than 40%. The bioavailability of Tramadol (Ultram) is typically around 75-95% when administered PO, and when delivered as an inhalable medicament with the device described herein, the bioavailability is greater than 75%. The bioavailability of Meperidine (Demerol) is typically around 57% when administered IM, and when delivered as an inhalable medicament with the device described herein, the bioavailability is greater than 57%. The bioavailability of Hydromorphone (Dilaudid) is typically around 24% when administered PO, and when delivered as an inhalable medicament with the device described herein, the bioavailability is greater than 24%.

Cannabinoids

Cannabinoids may, for example, be delivered by the inhalable medicament delivery device described herein with similar or improved bioavailability. Non-limiting examples of cannabinoids suitable for delivery with the described device include tetrahydrocannabinol (THC), as well as synthetic cannabinoids including the 1,5-diarylpyrazoles, quinolines, arylsulfonamides, and eicosanoids related to the endocannabinoids.

Bronchodilators

The medicament may comprise, for example, a bronchodilator. Non-limiting examples of bronchodilators suitable for delivery with the device described herein comprise salbutamol/albuterol, levosalbutamol/levalbuterol, pirbuterol, epinephrine, ephedrine, terbutalin, salmeterol, clenbuterol, formoterol, bambuterol, and indacaterol. The medicament may comprise, for example, a steroid. Non-limiting examples of bronchodilators suitable for delivery with the device described herein comprise beclomethasone dipropionate, budesonide, flunisolide, fluticasone propionate, mometasone furoate, and triamcinolone acetonide.

Vasodilators

The medicament may comprise a vasodilator, which may be used to treat a variety of conditions, including without limitation, erectile dysfunction. Such a medicament may comprise a phosphodiesterase (PDE) inhibitor or a prostoglandin. Some non-limiting examples of phosphodiesterase (PDE) inhibitors that may be delivered using a device according to this disclosure include Sildenafil (VIAGRA®), Tadalafil (ADCIRCA®, CIALIS®)), Vardenafil (LEVITRA®, STAXYN®), and Avanafil (STENDRA®). Prostoglandins that may be delivered with a device according to this disclosure include, but are not limited to Alprostadil (CAVERJECT®, MUSE®, EDEX®).

Biologics

The medicament may comprise a biological therapeutic. Non-limiting examples of biological therapeutics suitable for delivery with the device described herein may, for example, comprise DNA, RNA, and proteins. Biologics may be delivered using viral vectors and similar that would be suitable for use in the formulation. The fluid may further comprise an excipient.

Biosimilars

The medicament may comprise a biosimilar therapeutic. Non-limiting examples of biosimilar therapeutics suitable for delivery with the device described herein may, for example, comprise insulin, human growth hormone, various interferons, erythropoietin, and various monoclonal antibodies.

Antivirals

Antivirals may, for example, be delivered by the inhalable medicament delivery device described herein with similar or improved bioavailability. Non-limiting examples of antivirals suitable for delivery with the described device include Oseltamivir (Tamiflu), Zanamivir (Relenza), Amantadine (Symmetrel), and Rimantidine (Flumadine). The bioavailability of Oseltamivir (Tamiflu) is typically around 75% when administered PO, and when delivered as an inhalable medicament with the device described herein, the bioavailability is greater than 75%. The bioavailability of Zanamivir (Relenza) is typically around 4-17%, and when delivered as an inhalable medicament with the device described herein the bioavailability is equal to or greater than 4-17%. The bioavailability of Amantadine (Symmetrel) is typically around 86% when administered PO, and when delivered as an inhalable medicament with the device described herein, the bioavailability is greater than 90%.

Analgesics/Antihistamines

Combination analgesic/antihistamines may, for example, be delivered by the inhalable medicament delivery device described herein with similar or improved bioavailability. Non-limiting examples of antivirals suitable for delivery with the described device include Acetaminophen/Diphenhydramine (Tylenol PM) and Ibuprofen/Diphenhydramine (Advil PM). The bioavailability of Acetaminophen/Diphenhydramine (Tylenol PM) is typically around 65-100% when administered PO, and when delivered as an inhalable medicament with the device described herein, the bioavailability is around 100%. The bioavailability of Ibuprofen/Diphenhydramine (Advil PM) is typically around 65-100% when administered PO, and when delivered as an inhalable medicament with the device described herein, the bioavailability is around 100%.

Antitussives

Antitussives may, for example, be delivered by the inhalable medicament delivery device described herein with similar or improved bioavailability. Non-limiting examples of antitussives suitable for delivery with the described device include Dextromethorphan (Delsym), and Benzocaine/menthol or dextromethorphan. The bioavailability of Dextromethorphan (Delsym), and Benzocaine/menthol or dextromethorphan are similar when administered PO and when administered with the inhalable medicament delivery device described herein.

Decongestants

Decongestants may, for example, be delivered by the inhalable medicament delivery device described herein with similar or improved bioavailability. Non-limiting examples of decongestants suitable for delivery with the described device include Pseudoephedrine (Sudafed) and Phenylephrine. The bioavailability of Phenylephrine is typically around 38% when administered PO, and when delivered as an inhalable medicament with the device described herein, the bioavailability is greater than 38%.

Antihistamines

Antihistamines may, for example, be delivered by the inhalable medicament delivery device described herein with similar or improved bioavailability. Non-limiting examples of antihistamines suitable for delivery with the described device include Diphenhydramine (Benadryl), Hydroxyzine (Atarax), Cetirizine (Zyrtec), Loratadine (Claritin), and Fexofenadine (Allegra). The bioavailability of Diphenhydramine (Benadryl) is typically around 65-100% when administered PO, and when delivered as an inhalable medicament with the device described herein, the bioavailability is greater than 65%. The bioavailability of Cetirizine (Zyrtec) is typically around 70% when administered PO, and when delivered as an inhalable medicament with the device described herein, the bioavailability is greater than 70%. The bioavailabilities of Hydroxyzine (Atarax), Loratadine (Claritin), and Fexofenadine (Allegra) are similar when administered PO and when administered with the inhalable medicament delivery device described herein.

Expectorants

Expectorants may, for example, be delivered by the inhalable medicament delivery device described herein with similar or improved bioavailability. Non-limiting examples of expectorants suitable for delivery with the described device include Guaifenasin (Mucinex). The bioavailability of Guaifenasin (Mucinex) is similar when administered PO and when administered with the inhalable medicament delivery device described herein.

Nasal Sprays

Nasal sprays may, for example, be delivered by the inhalable medicament delivery device described herein with similar or improved bioavailability. Non-limiting examples of nasal sprays suitable for delivery with the described device include Azelastine (Astelin), Beclomethasone (Beconase, Qnasl), Mometasone (Nasonex), and Oxymetazoline (Afrin). The bioavailability of Azelastine (Astelin) is typically around 40% when administered as a nasal spray, and when delivered as an inhalable medicament with the device described herein, the bioavailability is greater than 40%. The bioavailability of Beclomethasone (Beconase, Qnasl) is typically around 41-43% when administered as a nasal spray, and when delivered as an inhalable medicament with the device described herein, the bioavailability is around 25-60%. The bioavailability of Mometasone (Nasonex) is typically around 1% when administered as an inhalable spray, and when delivered as an inhalable medicament with the device described herein, the bioavailability is greater than 1%. The bioavailability of Oxymetazoline (Afrin) is similar when administered PO and when administered with the inhalable medicament delivery device described herein.

Motion Sickness Medications

Motion sickness medications may, for example, be delivered by the inhalable medicament delivery device described herein with similar or improved bioavailability. Non-limiting examples of motion sickness medications suitable for delivery with the described device include Dimenhydrinate (Dramamine), Scopolamine (Transderm), and Meclizine (Bonine). The bioavailabilities of Dimenhydrinate (Dramamine) Scopolamine (Transderm), and Meclizine (Bonine) are similar when administered PO and when administered with the inhalable medicament delivery device described herein.

Analgesics

Analgesics may, for example, be delivered by the inhalable medicament delivery device described herein with similar or improved bioavailability. Non-limiting examples of analgesics suitable for delivery with the described device include Phenol (Chloraseptic spray), Menthol (Vicks VapoDrops), Duloxetine (Cymbalta), Pregabalin (Lyrica), Ibuprofen (Advil), Butalbital/Acetaminophen/Caffeine (Fioricet), Sumatriptan (Imitrex), Topiramate (Topamax), Carisoprodol (Soma), Tizanidine (Zanaflex), Naproxen sodium (Aleve), Ketorolac (Toradol), Celecoxib (Celebrex), Aspirin (Bayer), Acetaminophen (Tylenol, Ofirmev), and Acetaminophen/Caffeine/Pyrilamine (Midol Complete). The bioavailabilities of Phenol (Chloraseptic spray), Menthol (Vicks VapoDrops), Pregabalin (Lyrica), Butalbital/Acetaminophen/Caffeine (Fioricet), Carisoprodol (Soma), and Acetaminophen/Caffeine/Pyrilamine (Midol Complete) are similar when administered PO, and when administered with the inhalable medicament delivery device described herein. The bioavailability of Duloxetine (Cymbalta) is typically around 30-80% when administered PO, and when delivered as an inhalable medicament with the device described herein, the bioavailability is greater than 30%. The bioavailability of Ibuprofen (Advil) is typically around 58-98% when administered PO, and when delivered as an inhalable medicament with the device described herein, the bioavailability is greater than 58%. The bioavailability of Sumatriptan (Imitrex) is typically around 25% when administered through a nasal spray, and when delivered as an inhalable medicament with the device described herein, the bioavailability is greater than 15-25%. The bioavailability of Aspirin (Bayer) is typically around 61-80% when administered PO, and when delivered as an inhalable medicament with the device described herein, the bioavailability is greater than 61%. The bioavailability of Acetaminophen (Tylenol, Ofirmev) is typically around 85-100% when administered PO, and when delivered as an inhalable medicament with the device described herein, the bioavailability is greater than 85%.

Anesthetics

Anesthetics may, for example, be delivered by the inhalable medicament delivery device described herein with similar or improved bioavailability. Non-limiting examples of anesthetics suitable for delivery with the described device include Neostigmine (Prostigmin), Glycopyrrolate (Glycate), Isoflurane (Forane), Sevoflurane (Ultane), Desflurane (Suprane), Etomidate (Amidate), Propofol (Diprivan), Lidocaine (Xylocaine), Bupivicaine (Marcaine), Rocuronium (Zemuron), Vecuronium (Norcuron), Cisatracurium (Nimbex), Succinylcholine, Dexmedetomidine (Precedex), and Midazolam (Versed). The bioavailability of Isoflurane (Forane), Sevoflurane (Ultane), Desflurane (Suprane), Etomidate (Amidate), Propofol (Diprivan), Bupivicaine (Marcaine), Rocuronium (Zemuron), Vecuronium (Norcuron), Cisatracurium (Nimbex), Succinylcholine, and Dexmedetomidine (Precedex) are similar when administered PO, and when administered with the inhalable medicament delivery device described herein. The bioavailability of Neostigmine (Prostigmin) is typically around 1-2% when administered PO, and when delivered as an inhalable medicament with the device described herein, the bioavailability is greater than 1%. The bioavailability of Lidocaine (Xylocaine) is typically around 35% when administered PO, and when delivered as an inhalable medicament with the device described herein, the bioavailability is greater than 35%. The bioavailability of Midazolam (Versed) is typically around 36% when administered PO, and when delivered as an inhalable medicament with the device described herein, the bioavailability is greater than 36%.

Antimicrobials

Antimicrobials may, for example, be delivered by the inhalable medicament delivery device described herein with similar or improved bioavailability. Non-limiting examples of antimicrobials suitable for delivery with the described device include Gentamicin, Tobramycin (Tobi), Bacitracin (BACiiM), Chlorhexidine (Betasept), Fluconazole (Diflucan), Micafungin (Mycamine), Permethrin (Eimite), Ivermectin (Stromectol), Meropenem (Merrem), Ertapenem (Invanz), Cefazolin (Ancef), Cephalexin (Keflex), Cefoxitin (Mefoxin), Cefuroxime (Zinacef), Ceftriaxone (Rocephin), Ceftazidime (Fortaz), Cefepime (Maxipime), Ceftaroline (Teflaro), Ciprofloxacin (Cipro), Levofloxacin (Levaquin), Vancomycin (Vancocin), Azithromycin (Zithromax), Clarithromycin (Biaxin), Pencillin G, V, Amoxicillin (Amoxil), Amoxicillin/clavulanate (Augmentin), Piperacillin/tazobactam (Zosyn), Nafcillin, Trimethoprim/sulfamethoxazole (Bactrim), Minocycline (Minocin), Tetracycline, Doxycycline (Adoxa), Atovaquone/Proguanil (Malarone), Isoniazid, Rifampin, Ganciclovir (Cytovene), Valganciclovir (Valcyte), Acyclovir (Zovirax), Entecavir (Baraclude), Ribavirin (Copegus, Rebetol), Abacavir (Ziagen), Zidovudine (Retrovir), Efavirenz (Sustiva), Nevirapine (Viramune), Nelfinavir (Viracept), Ritonavir (Norvir), and Raltegravir (Isentress). The bioavailabilities of Bacitracin (BACiiM), Micafungin (Mycamine), Permethrin (Eimite), Ivermectin (Stromectol), Meropenem (Merrem), Cephalexin (Keflex), Cefuroxime (Zinacef), Ceftriaxone (Rocephin), Ceftaroline (Teflaro), Amoxicillin (Amoxil), Amoxicillin/clavulanate (Augmentin), Fluconazole (Diflucan), Tetracycline, Doxycycline (Adoxa), Valganciclovir (Valcyte), Entecavir (Baraclude), Efavirenz (Sustiva), Nelfinavir (Viracept), and Ritonavir (Norvir) are similar when administered PO, and when administered with the inhalable medicament delivery device described herein. The bioavailability of Gentamicin is typically negligible when administered PO and around 100% when administered IV, and when delivered as an inhalable medicament with the device described herein, the bioavailability is greater than 76%. The bioavailability of Tobramycin (Tobi) is typically around 1-16.6% when administered as an inhalable, and when delivered as an inhalable medicament with the device described herein, the bioavailability is greater than 1%. The bioavailability of Chlorhexidine (Betasept) is typically around 4% when administered PO, and when delivered as an inhalable medicament with the device described herein, the bioavailability is greater than 4%. The bioavailability of Ertapenem (Invanz) is typically around 90% when administered IV, and when delivered as an inhalable medicament with the device described herein, the bioavailability is greater than 90%. The bioavailability of Cefazolin (Ancef) is typically around 78% when administered IV, and when delivered as an inhalable medicament with the device described herein, the bioavailability is greater than 78%. The bioavailability of Cefoxitin (Mefoxin) is typically around 7-17% when administered PR, and when delivered as an inhalable medicament with the device described herein, the bioavailability is greater than 7%. The bioavailability of Cefepime (Maxipime) is typically around 82% when administered IM, and when delivered as an inhalable medicament with the device described herein, the bioavailability is greater than 82%. The bioavailability of Ciprofloxacin (Cipro) is typically around 60-80% when administered PO, and when delivered as an inhalable medicament with the device described herein, the bioavailability is greater than 60%. The bioavailability of Levofloxacin (Levaquin) is typically around 99% when administered PO, and when delivered as an inhalable medicament with the device described herein, the bioavailability is greater than 99%. The bioavailability of Vancomycin (Vancocin) is typically negligible when administered PO, and when delivered as an inhalable medicament with the device described herein, the bioavailability is greater than 38%. The bioavailability of Azithromycin (Zithromax) is typically around 38% when administered PO, and when delivered as an inhalable medicament with the device described herein, the bioavailability is greater than 38%. The bioavailability of Clarithromycin (Biaxin) is typically around 55% when administered PO, and when delivered as an inhalable medicament with the device described herein, the bioavailability is greater than 50%. The bioavailability of Penicillin G, V is typically around 30-80% when administered PO, and when delivered as an inhalable medicament with the device described herein, the bioavailability is greater than 30%. The bioavailability of Piperacillin/tazobactam (Zosyn) is typically around 71% when administered IM, and when delivered as an inhalable medicament with the device described herein, the bioavailability is greater than 71%. The bioavailability of Nafcillin is typically around 50% when administered PO, and when delivered as an inhalable medicament with the device described herein, the bioavailability is greater than 50%. The bioavailability of Trimethoprim/sulfamethoxazole (Bactrim) is typically around 90-100% when administered PO, and when delivered as an inhalable medicament with the device described herein, the bioavailability is greater than 90%. The bioavailability of Minocycline (Minocin) is typically around 90% when administered PO, and when delivered as an inhalable medicament with the device described herein, the bioavailability is greater than 90%. The bioavailability of Atovaquone/Proguanil (Malarone) is typically around 23% when administered PO, and when delivered as an inhalable medicament with the device described herein, the bioavailability is greater than 23%. The bioavailability of Isoniazid is typically around 90% when administered PO, and when delivered as an inhalable medicament with the device described herein, the bioavailability is greater than 90%. The bioavailability of Rifampin is typically around 90-95% when administered PO, and when delivered as an inhalable medicament with the device described herein, the bioavailability is greater than 90%. The bioavailability of Ganciclovir (Cytovene) is typically around 5% when administered PO, and when delivered as an inhalable medicament with the device described herein, the bioavailability is greater than 5%. The bioavailability of Acyclovir (Zovirax) is typically around 10-20% when administered PO, and when delivered as an inhalable medicament with the device described herein, the bioavailability is greater than 10%. The bioavailability of Ribavirin (Copegus, Rebetol) is typically around 64% when administered PO, and when delivered as an inhalable medicament with the device described herein, the bioavailability is greater than 64%. The bioavailability of Abacavir (Ziagen) is typically around 83% when administered PO, and when delivered as an inhalable medicament with the device described herein, the bioavailability is greater than 83%. The bioavailability of Abacavir (Ziagen) is typically around 61-89% when administered IV, and when delivered as an inhalable medicament with the device described herein, the bioavailability is greater than 61%. The bioavailability of Nevirapine (Viramune) is typically around 80-94% when administered PO, and when delivered as an inhalable medicament with the device described herein, the bioavailability is greater than 84%. The bioavailability of Raltegravir (Isentress) is typically around 20-43% when administered PO, and when delivered as an inhalable medicament with the device described herein, the bioavailability is greater than 20%. The bioavailability of Raltegravir (Isentress) is typically around 20-43% when administered PO, and when delivered as an inhalable medicament with the device described herein, the bioavailability is greater than 20%.

Biosimilar Molecules

Biosimilar molecules may, for example, be delivered by the inhalable medicament delivery device described herein with similar or improved bioavailability. Non-limiting examples of bisimilar molecules suitable for delivery with the described device include Interferon alfa 2b (Pegasys), Adenovirus 4, Albumin, human (Plasbumin, AlbuRx, Albutein, Albuminar), Alpha-1-proteinase inhibitor, human (Prolastin, Aralast, Zemaira, Glassia), Anthrax vaccine adsorbed (BioThrax), Antihemophlic factor, human (Koate, Hemofil, Monoclate), Antihemophlic factor, recombinant (Kogenate, Helixate, Refacto, Novoeight), Antihemophlic factor, recombinant, Fc fusion protein (Eloctate), Antihemophlic factor, recombinant, plasma/albumin free (Advate, xyntha), Antihemophlic factor, von Willebrand factor complex, human (Alphanate, Humate), Anti-Inhibitor coagulant complex (Autoplex, Feiba), Antithrombin, recombinant (ATryn), Antithrombin III, human (Thrombate III), Antithymocyte globulin, rabbit (Thymoglobulin), Antivenin polyvalent, crotalidae, Antivenin, *Lactrodectus mactans*, Antivenin, Micrurus Fulvius, Autologous cultured chondrocytes (Carticel), Azficel-T (LaViv), BCG Live (Tice, TheraCys), BCG Vaccine, Botulism antitoxin heptavalent, equine (BAT), Botulism immune globulin intravenous, human (Baby BIG), C1 esterase inhibitor, human (Cinryze, Berinert), C1 esterase inhibitor, recombinant (Ruconest), *Candida albicans* skin test antigen (Candin), Centruroides (scorpion) immune F (ab')2 (equine) injection (Anascorp), Coagulation factor IX, human (AlphaNine, Mononine), Coagulation factor IX, recombinant (BeneFIX, RIXUBIS), Coagulation factor IX, recombinant, Fc fusion protein (Alprolix), Coagulation factor VIIa, recombinant (NovoSeven), Coagulation factor XIII A subunit, recombinant (Tretten), *Coccidioides immitis* spherule-derived skin test antigen (Spherusol), Crotalidae polyvalent immune fab, ovine (CroFab), CMV immune globulin intravenous, human (CytoGam), Digoxin immune fab, ovine (Digibind, digiFab), DTaP toxoids adsorbed (Infanrix, Daptacel, Tripedia), DTaP toxoids adsorbed and inactivated poliovirus vaccine (Kinrix), DTaP/Hepatitis B (recombinant) and inactivated poliovirus vaccine (Pediarix), Factor IX complex (Profilnine, Bebulin), Factor XIII concentrate, human (Corifact), Fibrin sealant, human (Crosseal, Evicel, Artiss), Fibrin sealant (Tisseel), Fibrin sealant patch (TachoSil, Evarrest), Fibrinogen concentrate, human (RiaSTAP), *Haemophilus* B conjugate (meningococcal protein)/Hep B (recombinant) vaccine (COMVAX), *Haemophilus* B conjugate, meningococcal protein (PedvaxHIB), *Haemophilus* B conjugate vaccine, tetanus toxoid (ActHIB, OmniHIB, Hiberix), *Haemophilus* B conjugate vaccine, tetanus toxoid, reconstituted with DTaP toxoids (Pentacel), Hematopoietic progenitor cells, cord: HPC-C (Hemacord), Hemin for injection (Panhematin), Hepatitis A inactived/Hep B recombinant vaccine (Twinrix), Hepatitis A inactived (Havrix/VAQTA), Hepatitis B IG, human (BayHep, HyperHep, Nabi-HB, HepaGam B), Hepatitis B IG intravenous, human (HepaGam BT), Hepatitis B vaccine, recombinant (Recombivax/HB), Engerix-B), HPC, cord blood (DuCord, Allocord), HPV bivalent (16/18) vaccine, recombinant (Cervarix), HPV quad (6/11/16.18) vaccine, recombinant (Gardisil), Immune globulin, human (Gammastan, BayGam, IG infusion, human (Polygam, Kiovig, Gammagard, IG injection, human 10% caprylate/chromatography purified (Gamunex-C, Gammaked), IG intravenous, human (Sandoglobulin, Gammagard, Octagam, Flebogamma, Bivigam), IG intravenous, human 10% liquid (Privigen), IG intravenous, human 5% liquid (Gammaplex), IG SQ, human 20% liquid (Hizentra), Influenza A (H5N1) virus monovalent vaccine, adjuvanted, Influenza vaccine (FluBlok, Agriflu), Influenza vaccine live, intranasal (FluMist), Influenza virus vaccine (FluVirin, Fluzone, Fluarix, FluLaval, Afluria, Flucelvax), Influenza virus vaccine, H5N1, Insects (whole body), mite *Dermatophagoides farinae*, Insects (whole body), mite *Dermatophagoides pteronyssinus*, Japanese encephalitis vaccine, inactivated, adsorbed (Ixiaro), Lymphocyte IG, anti-thymocyte globulin, equine (Atgam), MMR virus vaccine live (M-M-R II), MMR and VZV vaccine live (ProQuad), Meningococcal (A/C/Y/W-135) oligosaccharide diphtheria CRM197 conjugate vaccine (Menveo), Meningococcal (A/C/Y/W-135) polysaccharide diphtheria CRM197 conjugate vaccine (Menactra), Meningococcal (C/Y) and *Haemophilus* B tetanus toxoid conjugate vaccine (Menhibrix), Meningococcal polysaccharide vaccine, group A (Menomune-A), Meningococcal polysaccharide vaccine, group C (Menomune-C), Meningococcal polysaccharide vaccine, groups A/C combined (Menomune-A/C), Meningococcal polysaccharide vaccine, groups A/C/Y/W-135 combined (Menomune), Allergen patch test kit, Non-standardized allergenics, Normal horse serum, Plague vaccine, Plasma protein fraction, human (plasmanate, protenate), Penumococcal 13-valent conjugate vaccine, Dipththeria CRM197 protein (Prevnar 13), Pneumococcal 7-valent conjugate vaccine, Dipththeria CRM197 protein (Prevnar), Pneumococcal vaccine, polyvalent (Pneumovax 23), Poliovirus inactivated (IPOL), Poliovirus inactivated, human diploid cell (Poliovax), Pollens—grasses, bermuda grass *Cynodon dactylon*, Pollens—grasses, bluegrass, kentucky (June) *Poa pratensis*, Pollens—grasses, fescue, meadow *Festuca elatior*, Pollens—grasses, orchard grass *Dactylis glomerata*, Pollens—grasses, redtop *Agrostis alba*, Pollens—grasses, ryegrass, perennial *Iolium perenne*, Pollens—grasses, sweet vernal grass *Anthoxanthum odoratum*, Pollens—grasses, timothy *Phleum pratense*, Pollens—weeds and garden plants, ragweed, short *Ambrosia artemisiifolia*, Pollens—weeds and garden plants, ragweed, short ambrosia eliator, Pooled plasma (human), solvent/detergent treated (Octaplas), Positive skin test control—histamine (Histatrol), Protein C concentrate, human (Ceprotin), Prothrombin complex concentrate, human (Kcentra), Rabies vaccine (RabAvert), Rabies IG, human (BayRab, HyperRab, Imogam), Rabies vaccine adsorbed (BioRab), Rho(D) IG, human (BayRho-D, RhoGam), Rho (D) IG, human intravenous (WinRho SDF, Rhophylac), Rotavirus vaccine, live, oral (Rotarix), Rotavirus vaccine, live, oral, pentavalent (RotaTeq), Short ragweed extract (Ragwitek), Sipuleucel-T (Provenge), Smallpox (vaccinia) vaccine, live (ACAM2000), Sweet vernal, orchard, perennial rye, timothy and kentucky blue grass mixed pollens allergen extract (Oralair), TDap adsorbed (Tenivac, Decavac), Tetatuns IG, human (BayTet), Tetanus toxoid adsorbed, Tetanus toxoid, reduced diphtheria toxoid and acellular pertussis vaccine, adsorbed (Boostrix, Adacel), Timothy grass pollen allergen extract (Grastek), Tuberculin, purified protein derivative (Aplisol, Tubersol), Typhoid vaccine live oral Ty21a (Vivotif), Typhoid Vi polysaccharide vaccine (Typhim Vi), Vaccinia IG Intravenous, human (CNJ-016), Varicella virus vaccine, live (Varivax), VZV IG, human (VariZIG), Venoms, honey bee venom (Pharmalgen), Venoms, wasp venom protein, Venoms, white faced hornet venom protein, Venoms, yellow hornet venom protein, Venoms, yellow jacet venom protein, von Willebrand factor/coagulation F VIII complex, human (Wilate), Yellow fever vaccine (YF-Vax), Zoster vaccine live (Zostavax), Abatacept (Orencia), Abciximab (ReoPro), AbobotulinumtoxinA (Dysport), Adalimumab (Humira), Ado-trastuzumab emantansine (Kadcyla), Afibercept (Eylea), Agalsidase beta (Fabrazyme), Albiglutide (Tanzeum), Aldesleukin (Proleukin), Alefacept (Amevive), and Alemtuzumab. The bioavailabilities of Adenovirus 4, Albumin, human (Plasbumin, AlbuRx, Albutein, Albuminar), Alpha-1-proteinase inhibitor, human (Prolastin, Aralast, Zemaira, Glassia), Anthrax vaccine adsorbed (BioThrax), Antihemophlic factor, and Anti-Inhibitor coagulant complex (Autoplex, Feiba) are similar when administered PO and when administered with the inhalable medicament delivery device described herein. The bioavailability of Interferon alfa 2b is typically around 80-90% when administered IM, and when delivered as an inhalable medicament with the device described herein, the bioavailability is greater than 80%. In general, the disclosed delivery will be improved when compared to other delivery methods except for intravenous injection, which is by definition 100% BA.

Additives

In an embodiment, a medicament comprises an excipient that, for example, increases the volume of the medicament. An excipient may also, for example, aid in the effective delivery of the medicament to a target.

In an embodiment, the medicament is stored as a liquid formulation. This liquid formulation of the medicament may be comprised primarily of glycerol acting as an excipient. The medicament may be pressurized by the use of carbon dioxide. For example, the medicament may be composed of a miscible solution of carbon dioxide and glycerol.

Glycerol has numerous advantageous properties. Glycerol is deemed safe for human inhalation. Glycerol has bacteriostatic properties. Glycerol may facilitate delivery of fragile biological therapeutics. Other primary liquid formulation components are also possible—such as water based or propylene glycol based. The medicament may also comprise other liquids similar to glycerol that are suitable for inhalation in aerosolized or vaporized form—such as sugar alcohols or diols. The hygroscopic properties of glycerol may be used to control for particle growth as the aerosol travels through the airways. The hygroscopic nature of glycerol is such that the MMAD of the particle will increase as the particle uptakes water in the humid human airway. This property is important as the initially generated aerosol can be biased to be small enough to mitigate losses through impaction, but evolve through hygroscopic enlargement to reach the target size for alveolar delivery of the excipient.

Examples of suitable excipients other than glycerol include, but are not limited to, the following: alcohols and polyols, such as ethanol, isopropanol, butanol, benzyl alcohol, ethylene glycol, propylene glycol, butanediols and isomers thereof, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

An acid, such as ascorbic acid, may be employed to acidify the medicament (e.g., to a low pH of around 4-5 in order to mitigate and reduce the absorption of the liquid formulation through the skin (transdermal absorption). Acidifying the medicament can also be used to mitigate or otherwise reduce the mucosal absorption of the medicament mixture. The acidification may be achieved by using other acids as well. The acidification of the medicament may also help decrease the risk of exposure to the unintended exposure to the active ingredients of the medicament by reducing transdermal and or mucosal absorption. Acidification may also, for example, pH buffer the basic pulmonary tissue, facilitating efficient diffusion of the medicament. In addition, the acidification of the medicament may serve as a deterrent to injection of the active ingredients of the medicament as a form of abuse of one or more active ingredients of the medicament. Acidification using ascorbic or citric acid (or others) may be used to increase tracheal stimulation, such as would be desirable when replicating the sensory cues and organoleptic experience of smoking a tobacco cigarette or other combustible material.

In some embodiments, the formulation comprises the medicament and ascorbic acid. In some embodiments, the amount of ascorbic acid provides the formulation a pH of about 4 to about 5. In some embodiments, the amount of ascorbic acid is X % by weight of ascorbic acid.

In some embodiments, an organosulfur compound is used to increase the absorption and diffusion of the medicament. For a non-limiting example, the organosulfur compound is dimethyl sulfoxide (DMSO). In some embodiments the formulation comprises the medicament and an organosulfur compound. The formulation may comprise at most 5% by weight of organosulfur compound. The formulation may comprise at most 5% by weight, about 5% by weight, 0.01% to 5% by weight, about 0.01% to about 5%, 0.05% to 5% by weight, about 0.05% to about 5%, 0.05% to 4% by weight, about 0.05% to about 4%, 0.01% to 3% by weight, about 0.01% to about 3%, 0.01% to 2% by weight, about 0.01% to about 2%, about 1%, about 1.5%, about 2%, about 2.5%, about 3%, about 3.5%, about 4%, about 0.1%, about 0.2%, about 0.3%, about 0.4%, about 0.5%, about 0.6%, about 0.7%, about 0.8%, or about 0.9% by weight of organosulfur compound. The formulation may comprise at most 5% by weight of dimethyl sulfoxide (DMSO). The formulation may comprise at most 5% by weight, about 5% by weight, 0.01% to 5% by weight, about 0.01% to about 5%, 0.05% to 5% by weight, about 0.05% to about 5%, 0.05% to 4% by weight, about 0.05% to about 4%, 0.01% to 3% by weight, about 0.01% to about 3%, 0.01% to 2% by weight, about 0.01% to about 2%, about 1%, about 1.5%, about 2%, about 2.5%, about 3%, about 3.5%, about 4%, about 0.1%, about 0.2%, about 0.3%, about 0.4%, about 0.5%, about 0.6%, about 0.7%, about 0.8%, or about 0.9% by weight of dimethyl sulfoxide (DMSO).

Excipients may also be used to enhance the drug formulation or the performance of the claimed device. For example, excipients include but are not limited to surfactants, preservatives, flavorings, antioxidants, antiaggregating agents, and cosolvents. In some embodiments, the medicament is flavored with an orange or bubble gum flavor to make the medicament more palatable, especially for young children.

Propellants

The medicament may further comprise a propellant in some embodiments. Examples of suitable propellants include but are not limited to inert gases, mixtures of inert gases, chlorofluorocarbons (CFCs), and hydrofluoroalkanes (HFAs). Examples of suitable inert gases include but are not limited to carbon dioxide and nitrogen. Other examples of suitable propellants include CFC-11 ($CCl_3F$), CFC-12 ($CCl_2F_2$), CFC-14 ($CCl_2F_4$), HFA-134a ($C_2H_2F_4$), HFA-227 ($C_3HF_7$), HCFC-22 (difluorochloromethane), and HFA-152 (difluroethane and isobutane).

In some embodiments, the propellant is an inert gas. In some embodiments, the propellant is carbon dioxide. In some embodiments, the propellant is nitrogen. In some embodiments, the propellant is a chlorofluorocarbon. In some embodiments, the propellant is a hydrofluoroalkane.

Methods of Treatment

Targeted Areas

In one aspect, the device may generate particles suitable for deposition in the mouth (e.g., for taste). In another example, the device may generate particles suitable for deposition in the pulmonary region for a fast acting effect. The location of deposition of aerosol particles within the respiratory system strongly determines the effectiveness of the administration of the medicament.

In another aspect, larger droplets or larger particles can be delivered to the trachea to, for example, promote tracheal stimulation. Tracheal stimulation may create a pleasant sensation in a subject. For example, when the device described herein delivers nicotine as a Nicotine Replacement Therapy (NRT), delivery of a droplet that causes tracheal stimulation may be a pleasant stimulation for a subject that, for example, promotes continued use of the therapy. Tracheal stimulation may also mimic the tracheal stimulation that some smokers experience.

In another aspect, a vapor may be useful for the delivery of organoleptic or sensory stimulating factors such as flavor.

The target of the medicament delivery may, for example, comprise the lung or a specific portion or area of the lung. The target of the medicament delivery may, for example, comprise the systemic vasculature. As will be further described herein, a target of medicament delivery, and a dose of medicament delivered to the target may be controlled by, for example, controlling the aerosol composition. That is, by controlling, for example, the droplet size, droplet shape, or the degree of vaporization. In addition, multiple lung targets may be targeted with the same medicament delivery. In an embodiment, a single aerosol mixture of different sized particles is generated. In an embodiment, two or more aerosols comprising different particle sizes are generated and delivered consecutively to the subject. In an embodiment, an aerosol particle size is modulated over time using the methods, devices and systems described herein. In these three embodiments of a single aerosol mixture containing different sized particles and of a plurality of aerosol compositions comprising different particle sizes, larger particles will tend to travel to the upper airway and smaller particles in the aerosol mixture will tend to travel deeper into the lung. In these embodiments, the inhalable medicament delivery device may be, for example, used to deliver a numbing agent comprising of larger aerosol particles together with a medicament comprising smaller particles. The numbing agent will be expected to numb the oropharynx so that there is less resistance to the smaller sized medicament intended to travel further along the airway, thus, improving the efficacy of delivery of the medicament. In an embodiment, three different sized particles are delivered so that each particle targets a different part of the airway. For example, a flavorant particle size may comprise a particle size equal to, for example, about 15 µm, a numbing agent particle size may comprise a particle size equal to, for example, about 10 µm, and particle size may comprise a particle size equal to about 15 µm, and a medicament particle size may comprise a particle size equal to, for example, about 5 µm.

The lungs comprise the alveoli, and pulmonary airways including the trachea, bronchi, and bronchioles. The human right lung comprises three lobes, the right superior lobe, middle lobe, and right inferior lobe. The human left lung comprises the left superior lobe, the lingula of the superior lobe, and left inferior lobe. The respective human lung lobes are generally positioned superiorly to inferiorly in a human standing or sitting in an upright position. The target of the inhalable medicament may for example comprise the superior portion of the lung, for example, comprising the right superior and left superior lobes. Such targeted delivery within the lung may be advantageous, for example, for targeted delivery of a chemotherapeutic agent to a localized lung lesion. Such targeted delivery within the lung may be advantageous, for example, for delivery of an antimicrobial agent to a localized infectious lesion within the lung. Numerous other advantageous examples of targeted pulmonary medicament delivery exist and will be understood by those having skill in the art.

Delivery of medicament to the lungs can also provide a means of rapid delivery of a medicament into the bloodstream through absorption into the alveolar-capillary membrane and the pulmonary vasculature, comprised of pulmonary arteries and veins. Generally, the pulmonary veins return oxygenated blood from the pulmonary circulation to the left atrium of the heart, wherein the blood travels to the left ventricle of the heart and then into systemic circulation, wherein the blood travels through the various tissue of the body. An aerosolized medicament that is capable of crossing the pulmonary blood barrier may enter the pulmonary circulation, travel through a pulmonary vein to the heart, and then into the systemic circulation, so that the medicament can be delivered to tissue in the body beyond the lungs. Systemic delivery of medicament through the pulmonary vasculature system may offer an advantageous alternative to, for example, to intravenous delivery of medicament.

In some embodiments, the aerosol generated is deposited in the mouth of the subject. In further embodiments, the particles of aerosol generated has a particle size of about 0.1 µm to about 15 µm or a MMAD of about 0.1 to about 15 µm. In some embodiments, the aerosol generated is deposited in the trachea of the subject. In further embodiments, the particles of aerosol generated has a particle size of about 0.1 µm to about 15 µm or a MMAD of about 0.1 to about 15 µm. In some embodiments, the aerosol generated is deposited in the lung of the subject. In further embodiments, the particles of aerosol generated has a particle size of about 0.1 µm to about 15 µm or a MMAD of about 0.1 to about 15 µm. In some embodiments, the aerosol generated is deposited in the superior lung lobe of the subject. In further embodiments, the particles of aerosol generated has a particle size of about 0.1 µm to about 15 µm or a MMAD of about 0.1 to about 15 µm. In some embodiments, the aerosol generated is deposited in the middle lung lobe of the subject. In further embodiments, the particles of aerosol generated has a particle size of about 0.1 µm to about 15 µm or a MMAD of about 0.1 to about 15 µm. In some embodiments, the aerosol generated is deposited in the inferior lung lobe of the subject. In further embodiments, the particles of aerosol generated has a particle size of about 0.1 µm to about 15 µm or a MMAD of about 0.1 to about 15 µm.

In some embodiments, the aerosol generated is deposited in the oropharynx. In further embodiments, the particles of aerosol generated has a particle size of about 0.1 µm to about 15 µm or a MMAD of about 0.1 to about 15 µm. In some embodiments, the aerosol generated is deposited in the central airways. In further embodiments, the particles of aerosol generated has a particle size of about 0.1 µm to about 15 µm or a MMAD of about 0.1 to about 15 µm. In some embodiments, the aerosol generated is deposited in the small airways. In further embodiments, the particles of aerosol generated has a particle size of about 0.1 µm to about 15 µm or a MMAD of about 0.1 to about 15 µm. In some embodiments, the aerosol generated is deposited in the alveoli. In further embodiments, the particles of aerosol generated has a particle size of about 0.1 µm to about 15 µm or a MMAD of about 0.1 to about 15 µm. In some embodiments, the aerosol generated is delivered to the pulmonary vasculature of the subject. In further embodiments, the particles of aerosol generated has a particle size of about 0.1 µm to about 15 µm or a MMAD of about 0.1 to about 15 µm.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

EXAMPLES

The following examples are provided for illustrative purposes only and not to limit the scope of the claims provided herein.

Example 1

Using any one of the devices described in this present application, the particle size distribution of the aerosol generated as was measured as a function of the temperature at which the aerosol is heated at. The mass median aerodynamic diameter (MMAD) was measured by using a Spraytec Particle Size Analyzer and a thermally regulated aerosol generator. In the following examples, pressure: 10%=about 8 psi, 50%=about 40-50 psi, 100%=about 80-90 psi of pressure applied to the device. Glycerol with a variable % of water was used the test liquid medicament. Results are shown in Tables 1 to 4.

TABLE 1

Mass Median Aerodynamic Diameter (MMAD) of Glycerol with 0.5% Water

| Temperature (° C.) | Pressure | MMAD (μm) |
|---|---|---|
| 100 | 10% | 0.44 |
| 100 | 50% | 0.49 |
| 100 | 100% | 0.87 |
| 150 | 10% | 1.67 |
| 150 | 50% | 0.50 |
| 150 | 100% | 0.44 |
| 175 | 10% | 3.12 |
| 175 | 50% | 1.06 |
| 175 | 100% | 0.39 |
| 200 | 10% | 4.03 |
| 200 | 50% | 2.48 |
| 200 | 100% | 0.59 |

TABLE 2

Mass Median Aerodynamic Diameter (MMAD) of Glycerol with 1% Water

| Temperature (° C.) | Pressure | MMAD (μm) |
|---|---|---|
| 100 | 10% | 0.55 |
| 100 | 50% | 0.50 |
| 100 | 100% | 0.89 |
| 150 | 10% | 1.80 |
| 150 | 50% | 0.47 |
| 150 | 100% | 0.45 |
| 175 | 10% | 3.27 |
| 175 | 50% | 0.42 |
| 175 | 100% | 0.40 |
| 200 | 10% | 4.36 |
| 200 | 50% | 1.44 |
| 200 | 100% | — |

TABLE 3

Mass Median Aerodynamic Diameter (MMAD) of Glycerol with 2.5% Water

| Temperature (° C.) | Pressure | MMAD (μm) |
|---|---|---|
| 100 | 10% | 0.49 |
| 100 | 50% | 0.49 |
| 100 | 100% | 0.84 |
| 150 | 10% | 2.27 |
| 150 | 50% | 0.45 |
| 150 | 100% | 0.58 |
| 175 | 10% | 3.63 |
| 175 | 50% | 0.43 |
| 175 | 100% | 0.42 |
| 200 | 10% | 4.47 |
| 200 | 50% | 0.49 |
| 200 | 100% | 0.48 |

TABLE 4

Mass Median Aerodynamic Diameter (MMAD) of Glycerol with 5% Water

| Temperature (° C.) | Pressure | MMAD (μm) |
|---|---|---|
| 100 | 10% | 0.48 |
| 100 | 50% | 0.52 |
| 100 | 100% | 0.78 |
| 150 | 10% | 2.31 |
| 150 | 50% | 0.47 |
| 150 | 100% | 0.43 |
| 175 | 10% | 3.61 |
| 175 | 50% | 0.39 |
| 175 | 100% | 0.44 |
| 200 | 10% | 2.37 |
| 200 | 50% | 1.70 |
| 200 | 100% | 0.68 |

Example 2

Using the same experimental setup as described in Example 1, the mass median aerodynamic diameter (MMAD) was determined on a test medicament containing glycerol, nicotine and water. Results are shown in Tables 5 to 8.

TABLE 5

Mass Median Aerodynamic Diameter (MMAD) of Glycerol/Nicotine with 0.5% Water

| Temperature (° C.) | Pressure | MMAD (μm) |
|---|---|---|
| 100 | 50% | 0.65 |
| 100 | 100% | 0.67 |
| 150 | 50% | 0.41 |
| 150 | 100% | 0.48 |
| 175 | 50% | 0.43 |
| 175 | 100% | 0.44 |
| 200 | 50% | 0.39 |
| 200 | 100% | 0.43 |

TABLE 6

Mass Median Aerodynamic Diameter (MMAD) of Glycerol/Nicotine with 1% Water

| Temperature (° C.) | Pressure | MMAD (μm) |
|---|---|---|
| 100 | 50% | 0.65 |
| 100 | 100% | 0.81 |
| 150 | 50% | 0.41 |
| 150 | 100% | 0.50 |
| 175 | 50% | 0.44 |
| 175 | 100% | 0.40 |
| 200 | 50% | 0.51 |
| 200 | 100% | 0.39 |

TABLE 7

Mass Median Aerodynamic Diameter (MMAD) of Glycerol/Nicotine with 2.5% Water

| Temperature (° C.) | Pressure | MMAD (μm) |
|---|---|---|
| 100 | 50% | 0.67 |
| 100 | 100% | 1.03 |

TABLE 7-continued

Mass Median Aerodynamic Diameter (MMAD) of Glycerol/Nicotine with 2.5% Water

| Temperature (° C.) | Pressure | MMAD (μm) |
|---|---|---|
| 150 | 50% | 0.35 |
| 150 | 100% | 0.56 |
| 175 | 50% | 0.46 |
| 175 | 100% | 0.37 |
| 200 | 50% | 0.45 |
| 200 | 100% | 0.46 |

TABLE 8

Mass Median Aerodynamic Diameter (MMAD) of Glycerol/Nicotine with 5% Water

| Temperature (° C.) | Pressure | MMAD (μm) |
|---|---|---|
| 100 | 50% | 0.64 |
| 100 | 100% | 1.17 |
| 150 | 50% | 0.47 |
| 150 | 100% | 0.47 |
| 175 | 50% | 0.40 |
| 175 | 100% | 0.35 |
| 200 | 50% | 0.45 |
| 200 | 100% | 0.44 |

Example 3

Using the same experimental setup as described in Example 1, the mass median aerodynamic diameter (MMAD) is determined on a test medicament containing glycerol and any one of the active therapeutic agents described in this application with varying amounts of water.

What is claimed:

1. A delivery device capable of delivering an inhalable medicament to a subject, comprising:
a housing including a reservoir tap comprising a conduit; and
a cartridge, comprising:
a seal positioned adjacent to the reservoir tap when the cartridge is coupled to the housing; and
an inhalable medicament within the cartridge, the inhalable medicament compressed to a pressure above ambient pressure,
the reservoir tap selectively operable to penetrate the seal, aerosolizing the inhalable medicament and ejecting the inhalable medicament into the housing.

2. The delivery device of claim 1, wherein the seal comprises a self-healing seal.

3. The delivery device of claim 1, wherein the housing further includes an aspiration conduit into which the reservoir tap can eject the inhalable medicament.

4. The delivery device of claim 3, wherein the housing further includes a heater associated with the aspiration conduit.

5. The delivery device of claim 1, wherein the reservoir tap slides between a retracted position and an extended position.

6. The delivery device of claim 5, wherein, when in the extended position and with the cartridge coupled to the housing, the reservoir tap extends through the seal of the cartridge, establishing communication between an interior of the cartridge and the conduit of the reservoir tap.

7. The delivery device of claim 1, wherein the cartridge further comprises a porous matrix within the cartridge, the inhalable medicament residing within pores of the porous matrix.

8. The delivery device of claim 7, wherein the porous matrix is located between the seal and a gaseous propellant.

9. An inhaled medicament delivery device, comprising:

a cartridge including:

a housing coupler;

a reservoir including an opening;

a seal positioned over the opening of the reservoir and sealing the reservoir; and a liquid medicament within the reservoir; and a gaseous propellant compressed to an above-ambient pressure and capable of atomizing and pressurizing the liquid medicament; and a housing including:

a cartridge coupler adapted to releasably engage or to be releasably engaged by the housing coupler of the cartridge;

an aspiration conduit capable of receiving atomized medicament; and a reservoir tap in communication with the aspiration conduit, the reservoir tap slideable between:

a retracted position that, with the cartridge coupled to the housing, is out of contact with the seal of the cartridge; and an extended position that, with the cartridge coupled to the housing, extends through the seal of the cartridge to establish communication between the reservoir and the aspiration conduit.

10. The inhaled medicament delivery device of claim 9, further comprising:

a heater associated with the aspiration conduit.

11. The inhaled medicament delivery device of claim 9, wherein the reservoir tap includes:

a body;

a tip at an end of the body;

a first conduit extending through the body, a first port of the first conduit opening to the tip; and a second conduit extending through the body, a second port of the second conduit opening to a more intermediate location along a length of the body, the reservoir tap having:

the retracted position;

an intermediate position between the retracted position and the extended position, in which:

the first port is positionable within the reservoir of the cartridge with the cartridge coupled to the housing; and the second port is located out of communication with the reservoir with the cartridge coupled to the housing; and the extended position, in which:

the first port is positionable within the reservoir of the cartridge; and the second port is positionable within the reservoir of the cartridge.

12. The inhaled medicament delivery device of claim 11, wherein the second port is larger than the first port.

13. The inhaled medicament delivery device of claim 9, wherein the reservoir of the cartridge comprises a porous matrix, the liquid medicament being located within pores of the porous matrix.

14. The inhaled medicament delivery device of claim 13, wherein the porous matrix is located between the gaseous propellant of the cartridge and the seal of the cartridge.

15. The inhaled medicament delivery device of claim 9, wherein the seal of the cartridge comprises a self-healing seal.

16. A cartridge adapted for use in storing an inhalable medicament and delivering the inhalable medicament to a subject, comprising:
- a reservoir with an opening;
- a seal over the opening of the reservoir;
- a liquid medicament within the reservoir;
- a gaseous propellant compressed to an above-ambient pressure and capable of atomizing and pressurizing the liquid medicament within the reservoir; and
- a housing coupler adapted to releasably engage or to be releasably engaged by a housing of a delivery device.

17. The cartridge of claim 16, comprising a porous matrix within the reservoir, the liquid medicament residing within pores of the porous matrix.

18. The cartridge of claim 17, wherein the porous matrix is located between the seal and the gaseous propellant.

19. The cartridge of claim 16, wherein the gaseous propellant is within the reservoir.

20. The cartridge of claim 16, wherein the seal comprise a self-healing seal.

\* \* \* \* \*